(12) United States Patent
Man et al.

(10) Patent No.: US 9,127,238 B2
(45) Date of Patent: Sep. 8, 2015

(54) FOAM STABILIZATION WITH POLYETHYLENEIMINE ETHOXYLATES

(71) Applicant: Ecolab USA Inc., St. Paul, MN (US)

(72) Inventors: Victor Fuk-Pong Man, St. Paul, MN (US); Yvonne Marie Killeen, South St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 14/263,024

(22) Filed: Apr. 28, 2014

(65) Prior Publication Data

US 2014/0287981 A1 Sep. 25, 2014

Related U.S. Application Data

(63) Continuation of application No. 13/791,054, filed on Mar. 8, 2013, now Pat. No. 8,759,276.

(60) Provisional application No. 61/730,723, filed on Nov. 28, 2012.

(51) Int. Cl.
  *C11D 1/12* (2006.01)
  *C11D 1/75* (2006.01)
  *B08B 3/04* (2006.01)
  (Continued)

(52) U.S. Cl.
  CPC ............. *C11D 3/3723* (2013.01); *C11D 1/94* (2013.01); *C11D 3/0026* (2013.01)

(58) Field of Classification Search
  CPC .......... C11D 1/12; C11D 1/75; C11D 3/3723; B08B 3/04

USPC ................ 510/421, 423, 426, 475, 490, 496; 134/25.2, 25.3, 39, 42
See application file for complete search history.

(56) References Cited

U.S. PATENT DOCUMENTS 3,489,686 A   1/1970 Parran, Jr.
5,576,279 A * 11/1996 Pyles .......................... 510/122

(Continued)

FOREIGN PATENT DOCUMENTS

EP    0911022    4/1999
EP    0916720    5/1999

(Continued)

OTHER PUBLICATIONS

Angelescu, Daniel George, et al., "Adsorption of Branched-Linear Polyethyleneimine-Ethylene Oxide Conjugate on Hydrophilic Silica Investigated by Ellipsometry and Monte Carlo Simulations", Langmuir, ACS Publications 2011, pp. 9961-9971. Dec. 31, 2011.
BASF The Chemical Company, "Care Chemicals & Formulators, Lupasol types", pp. 1-10. Apr. 30, 2010.

(Continued)

*Primary Examiner* — Brian P Mruk
(74) *Attorney, Agent, or Firm* — McKee, Voorhees & Sease, PLC

(57) ABSTRACT

The invention involves foam stabilization compositions that rely upon an electrostatic charge interaction. According to the invention, the positively charged class of polymers such as polyethyleneimine (PEI) polymers are used to provide a long range electrostatic interaction with detersive anionic or amphoteric surfactants present in the same. The interaction must be of sufficient character so that the components do not precipitate out, instead causing longer lasting and increased foam production. The system provides an environmentally friendly alternative for traditional foaming enhancers such as cocamide DEA.

18 Claims, 36 Drawing Sheets

(51) Int. Cl.
*C11D 3/37* (2006.01)
*C11D 1/94* (2006.01)
*C11D 3/00* (2006.01)

(56) References Cited

U.S. PATENT DOCUMENTS

| | | |
|---|---|---|
| 5,700,771 A | 12/1997 | Hardy et al. |
| 6,258,859 B1 | 7/2001 | Dahayanake et al. |
| 6,482,866 B1 | 11/2002 | Dahayanake et al. |
| 6,608,020 B1 | 8/2003 | Durbut et al. |
| 6,703,352 B2 | 3/2004 | Dahayanake et al. |
| 6,831,108 B2 | 12/2004 | Dahanayake et al. |
| 7,025,883 B1 | 4/2006 | Olivier |
| 7,238,648 B2 | 7/2007 | Dahayanake et al. |
| 7,279,446 B2 | 10/2007 | Colaco et al. |
| 7,481,935 B2 | 1/2009 | Olivier |
| 7,999,035 B2 | 8/2011 | Boeckh et al. |
| 8,759,276 B2 * | 6/2014 | Man et al. ............. 510/475 |
| 2002/0069901 A1 | 6/2002 | Evers |
| 2003/0119706 A1 | 6/2003 | Pfeiffer et al. |
| 2007/0004609 A1 | 1/2007 | Hloucha et al. |
| 2009/0111716 A1 | 4/2009 | Hough et al. |
| 2009/0215662 A1 | 8/2009 | Boeckh et al. |
| 2010/0294498 A1 | 11/2010 | Svoboda et al. |
| 2011/0028374 A1 * | 2/2011 | Fossum et al. ........... 510/296 |
| 2011/0092398 A1 | 4/2011 | Dahanayake et al. |
| 2012/0058166 A1 * | 3/2012 | Glenn et al. ............. 424/401 |
| 2012/0122747 A1 * | 5/2012 | Nekmard et al. ......... 510/218 |

FOREIGN PATENT DOCUMENTS

| | | |
|---|---|---|
| WO | 9723546 | 7/1997 |
| WO | 9728207 | 8/1997 |
| WO | 9728208 | 8/1997 |
| WO | 9907815 | 2/1999 |
| WO | 2010025116 | 3/2010 |
| WO | 2011143602 | 11/2011 |

OTHER PUBLICATIONS

Procter & Gamble Professional, "Material Safety Data Sheet—Dawn Heavy Duty Floor Cleaner", Version 5, pp. 1-4. Oct. 28, 2010.
Procter & Gamble Professional, "Material Safety Data Sheet—Dawn Heavy Duty Floor Cleaner—concentrate", Version 3, pp. 1-5. Nov. 1, 2010.
Procter & Gamble Professional, "Material Safety Data Sheet—Dawn Liquid Detergent for Power Wash Sinks—concentrate", Version 5, pp. 1-5. Apr. 5, 2011.
Procter & Gamble Professional, "Material Safety Data Sheet—Dawn Liquid Detergent for Power Wash Sinks", Version 3, pp. 1-4. Nov. 1, 2010.
Procter & Gamble Professional, "Material Safety Data Sheet—Dawn Manual Pot and Pan Detergent—Concentrate", Version 8, pp. 1-5. Nov. 3, 2010.
Procter & Gamble Professional, "Material Safety Data Sheet—Dawn Manual Pot and Pan Detergent", Version 6, pp. 1-4. Nov. 1, 2010.
Procter & Gamble Professional, "Material Safety Data Sheet—Dawn Professional Dish Detergent", Version 1, pp. 1-5. May 2, 2012.
Procter & Gamble Professional, "Material Safety Data Sheet—Dawn Ultra Heavy Duty Degreaser concentrate", Version 3, pp. 1-5. May 4, 2011.
Procter & Gamble Professional, "Material Safety Data Sheet—Mr. Clean Magic Eraser with the Grease Fighting Power of Dawn", pp. 1-5. Jun. 30, 2010.
Ecolab USA Inc., PCT/US2013/029963, filed on Mar. 8, 2013 The International Search Report and the Written Opinion of the International Searching Authority, or the Declaration. Jul. 25, 2013.
PCT/US2013/071550—Ecolab USA Inc. (2866WO01) filed Nov. 23, 2013, "Notification of Transmittal of the International Search Report and the Written Opinion of the International Searching Authority, or the Declaration" Feb. 24, 2014.
PCT/US2013/071549—Ecolab USA Inc. (2990WO01) filed Nov. 23, 2013, "Notification of Transmittal of the International Search Report and the Written Opinion of the International Searching Authority, or the Declaration" Feb. 24, 2014.

* cited by examiner

FOAM STABILIZATION WITH POLYETHYLENEIMINE ETHOXYLATES

This application is a Continuation Application of U.S. Ser. No. 13/791,054 filed Mar. 8, 2013, now U.S. Pat. No. 8,759,276 issued Jun. 24, 2013, which claims priority under 35 U.S.C. §119 to provisional application Ser. No. 61/730,723 filed Nov. 28, 2012, all of which are herein incorporated by reference in their entirety.

FIELD OF THE INVENTION

The present invention relates to novel foam stabilizing compositions which act by the formation of long range intermolecular interactions (electrostatic or ionic) for use in cleaning compositions. Such foam stabilizing compositions can be used as a replacement for traditional foaming agents which are under regulatory pressure in such cleaning compositions as pot and pan soaking compositions, hand soaps, foam fractionation, gas exploration water removal, food and beverage foaming cleaners, vehicle cleaning and the like. The invention further also relates to methods of making these compositions, and to methods employing these compositions.

BACKGROUND OF THE INVENTION

Many cleaning compositions include a foaming agent to increase contact time on surfaces to be cleaned. Such compositions are presently used in many applications, such as retail, industrial and institutional including grease cutters, clinging lime scale removers, shower wall cleaners, bathtub cleaners, hand sanitizing gels, disinfectant gels, hand-soaps, teat dips, coatings, stabilized enzymes, structured liquids, and the like.

The most widely used foaming agent is cocamide DEA, or cocamide diethanolamine, a diethanolamide made by reacting a mixture of fatty acids from coconut oils (cocamide) with diethanolamine. The agent may also been known as lauramide diethanolamine, Coco Diethanolamide, coconut oil amide of diethanolamine, Lauramide DEA, Lauric diethanolamide, Lauroyl diethanolamide, and Lauryl diethanolamide.

It is a viscous liquid and is used as a foaming agent in bath products like shampoos and hand soaps, and in cosmetics as an emulsifying agent. The chemical formula is $CH_3(CH_2)_nC(=O)N(CH_2CH_2OH)_2$, where n can vary depending on the source of fatty acids. Coconut oil contains about 50% of lauric acid, thus the formula of cocamide can be written as $CH_3(CH_2)_{10}CONH_2$, though the number of carbon atoms in the chains varies. Cocamide DEA has come under criticism lately and is under regulatory pressure to have it removed from products. It is an allergen that can cause contact dermatitis in individuals who are susceptible to skin allergies. More recently, cocamide DEA has been linked to cancer.

The International Agency for Research on Cancer (IARC) lists coconut oil diethanolamine condensate (cocamide DEA) as an IARC Group 2B carcinogen, which identifies this chemical as possibly carcinogenic to humans. In June 2012, the California Office of Environmental Health Hazard Assessment added Cocamide DEA to the California Proposition 65 (1986) list of chemicals known to cause cancer.

Accordingly it is an object herein to provide a foam stabilizer that can be used as a replacement for cocamide DEA.

It is yet another object of the invention to provide a foam stabilizer that is safe, environmentally friendly and economically feasible.

Other objects, aspects and advantages of this invention will be apparent to one skilled in the art in view of the following disclosure, the drawings, and the appended claims.

SUMMARY OF THE INVENTION

The invention involves foam stabilization compositions that rely upon an electrostatic charge interaction or an non-ionic/hydrophobic interaction. The invention contemplates the use of an anionic surfactant or certain amphoteric surfactants combined with a polymer that is has positive or cationic charges. It is essential that the cationic polymer interact with but not precipitate the surfactant. This intermolecular interaction as provided by the invention, provides foam stability, including the water that is a component of the foam.

According to the invention, the positively charged class of polymers such as polyethyleneimine (PEI) and its derivatives such as ethoxylated (PEI) polymers, propoxylated (PEI) polymers, polyamines, polyquats, polyglycerol quats, and other PEI derivatives, their salts or mixtures thereof are used in foaming compositions to provide the electrostatic interaction with surfactants present in the foaming compositions, particularly preferred are ethoxylated or propoxylated PEI polymers. In preferred such embodiments, the PEI or PEIs are branched, spherical polymeric amines, and the molecular weight of the PEI or PEI salt used is from about 800 daltons to about 2 million Daltons. In addition, in preferred such embodiments, the charge density of the PEI or PEI salt used is from about 15 meq/g to about 25 meq/g, more preferably from about 16 meq/g to about 20 meq/g. Examples of such preferred PEIs include the BASF products LUPASOL WF (25 kDa; 16-20 meq/g) and Lupasol® FG (800 daltons; 16-20 meq/g), and the SOKALAN® family of polymers available from BASF, e.g., SOKALAN® HP20, SOKALAN® HP22 G, and the like.

According to the invention, cleaning compositions are formed with an detersive amount of an anionic surfactant (from about 1 wt. % to about 75 wt. %) and from about 0.01 wt. % to about 5.0 wt. % of ethoxylated PEI or other similarly positive charged polymer such as polyamines, polyquats, polyclycerol quats, and products commercially available from Nalco such as VX10035 a propoxylated PEI and two other Nalco products, VX9945 and VX9946, in which the PEI is first propoxylated then exthoxylated.

In another embodiment the cleaning compositions are formed with an amphoteric surfactant selected from the group including amine oxide or betaines and sultaines (described hereinafter as zwitterionic surfactants). The amphoteric surfactant is present in an amount of from about 0.01 wt. % to about 75 wt. % and PEI is present in an amount from about 0.01 wt. % to about 5.0 wt. %.

In a preferred embodiment the amine oxide is present in an amount of less than 8 wt. % active. In a more preferred embodiment the composition includes both an anionic surfactant in an amount of from about 1 wt. % to about 75 wt. % and less than 8 wt. % active of amine oxide in addition to the PEI polymer. The composition also includes water and additional optional detersive ingredients. The cleaning compositions are substantially free of cocamide DEA. Other surfactants and standard cleaning composition components may also be included as well.

The foaming cleaning compositions of the invention are advantageously be formulated to cocamide DEA free, phosphate-free and aminocarboxylate-free, as well as containing only ingredients generally recognized as safe (GRAS) for human use.

In a preferred embodiment the cleaning composition is cocamide DEA-free. Cocamide DEA-free refers to a composition, mixture, or ingredients to which cocamide DEA-containing compounds are not added. Should these compounds be present, for example through contamination of a cocamide DEA-free composition, mixture, or ingredients, the level of the same shall be less than 0.5 wt. %, may be less than 0.1 wt. %, and often less than 0.01 wt. %.

In another aspect, the presently described technology provides a process to prepare a cocamide DEA free foaming cleaning composition. The process can include the steps of adding to an aqueous medium a detersive amount of anionic surfactant or amphoteric surfactant and from about 0.01% wt. % to about 5 wt. % of one or more positively charged polymers such as ethoxylated PEI. In certain formulations, the method will also include the step of adding less than 8 wt. % active of amine oxide.

A novel cleaning method is also within the invention and involves applying the foaming cleaning mixture to a surface to be cleaned, allowing the foam to remain for a sufficient period of time for cleaning (typically until the foam dissipates) and thereafter rinsing said surface to that said cleaning composition is removed along with soil and debris.

DETAILED DESCRIPTION OF PREFERRED EMBODIMENTS

Figure 1:
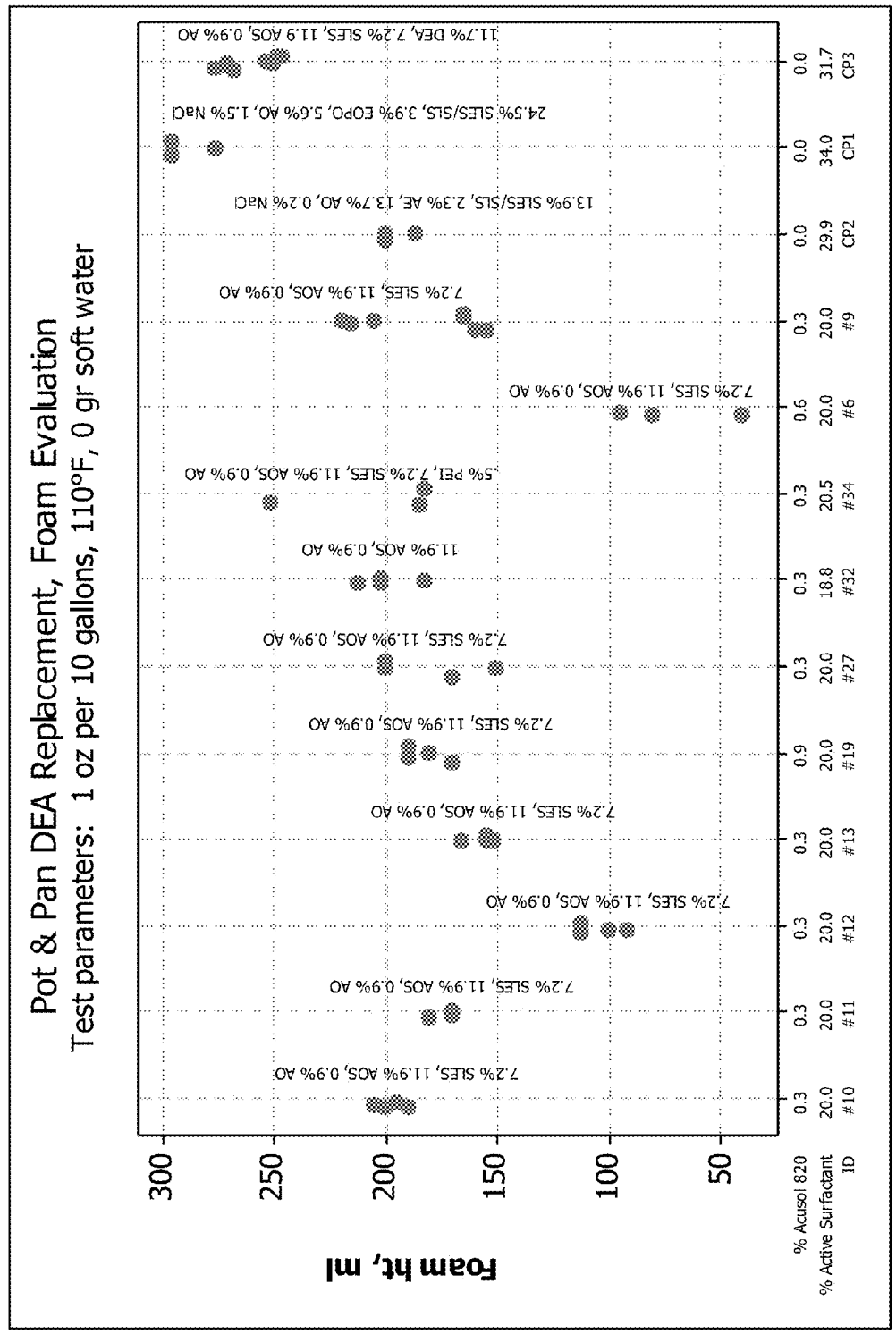
FIG. 1 is a graph depicting foam height of formulas 6, 9, 10, 11, 12, 13, 19, 28, 32, and 34 with commercially available foaming pot and pan cleaning products Commercial Product 1 and Commercial Product 2 (which include PEI-14 PEG-10/PPG-7) and Commercial Product 3.
Figure 2:
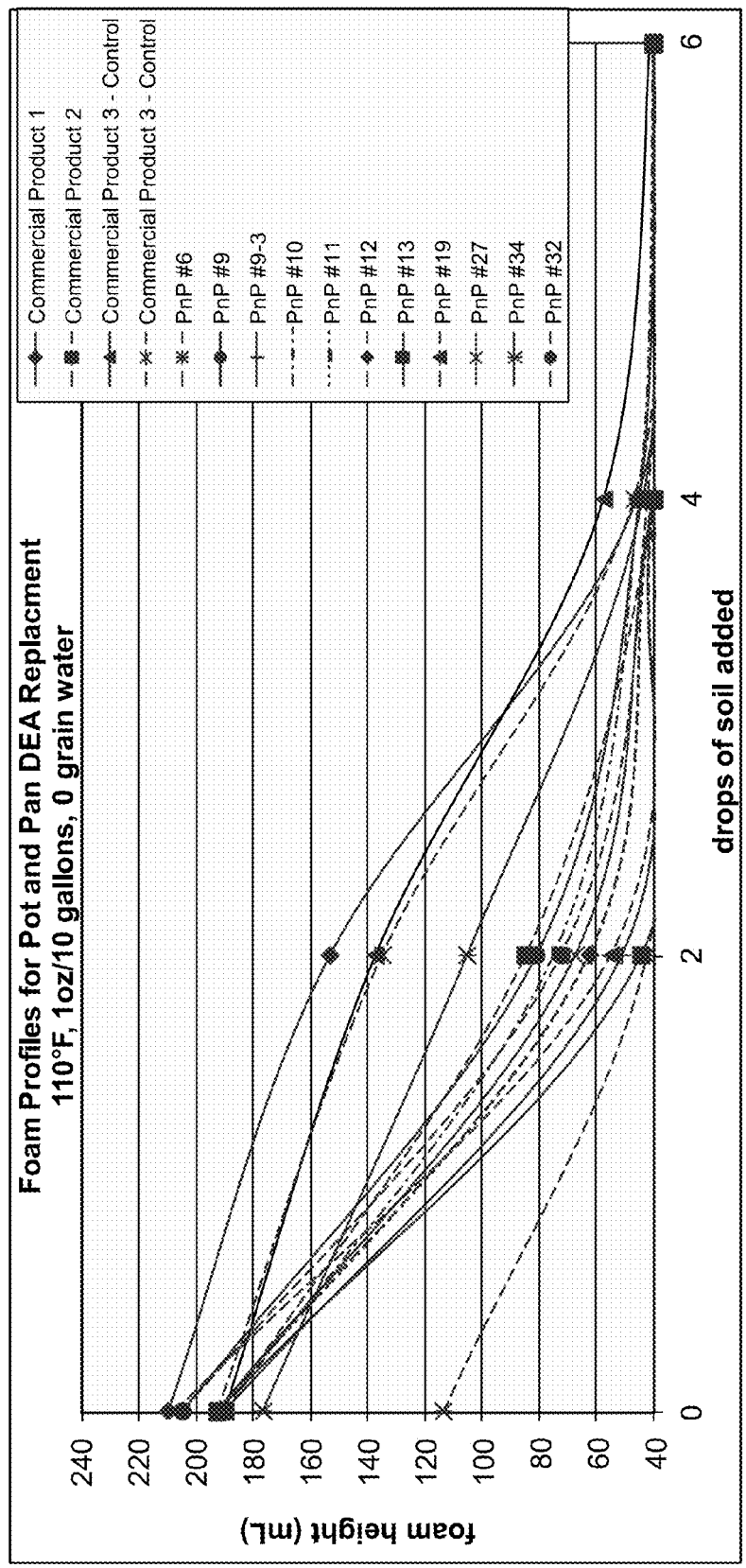
FIG. 2 is a graph depicting foam height as drops of soil are added for Commercial Products 1, 2, and 3, and formulas 6, 9, 9-3, 10, 11, 12, 13, 19, 27, 34, and 32.
Figure 3:
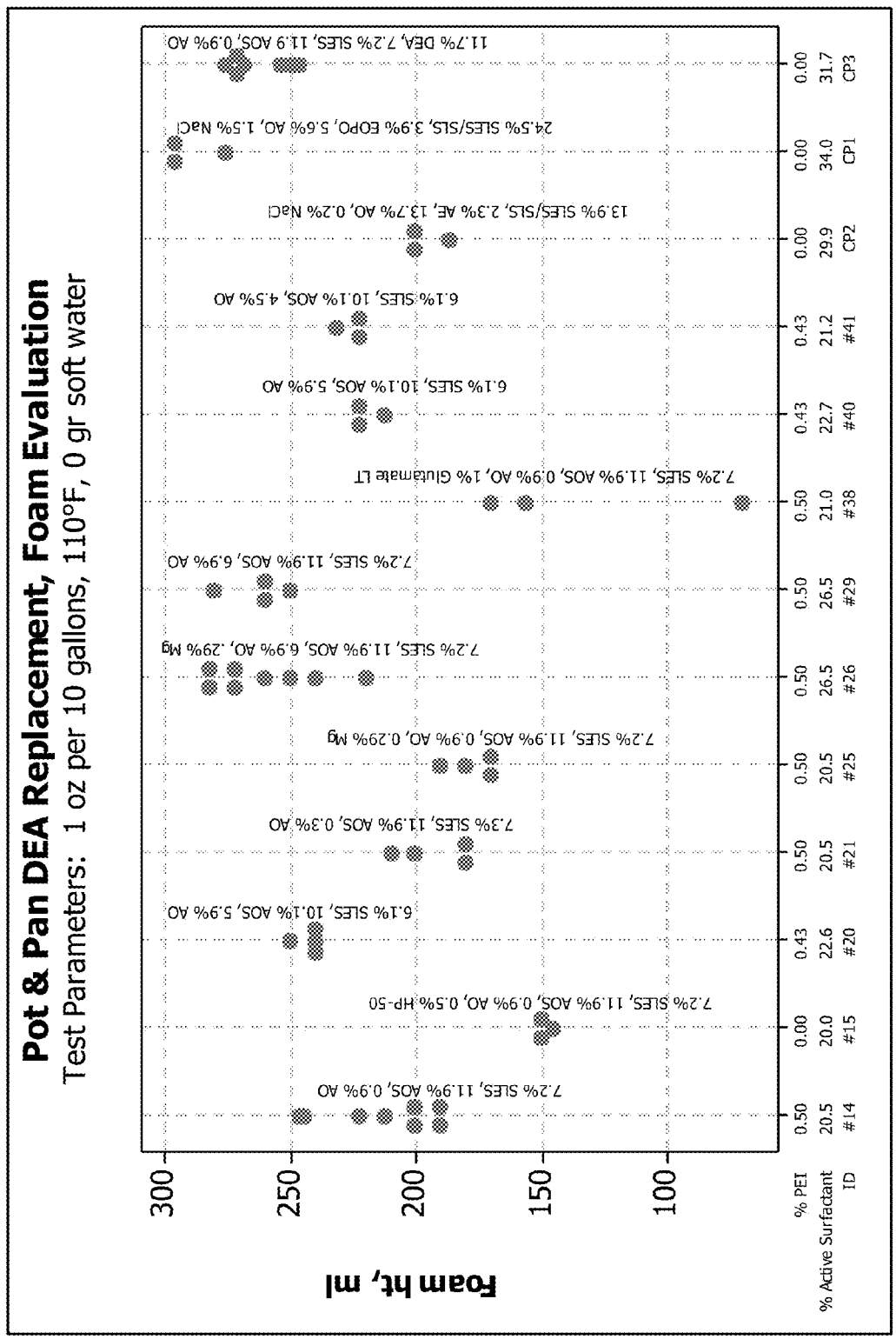
FIG. 3 is a graph depicting foam height of formulas 15, 20, 21, 14, 29, 25, 26, 38, 40, and 41 with commercially available foaming pot and pan cleaning products Commercial products 1 and 2 (which include PEI-14 PEG-10/PPG-7) and Commercial Product 3.
Figure 4:
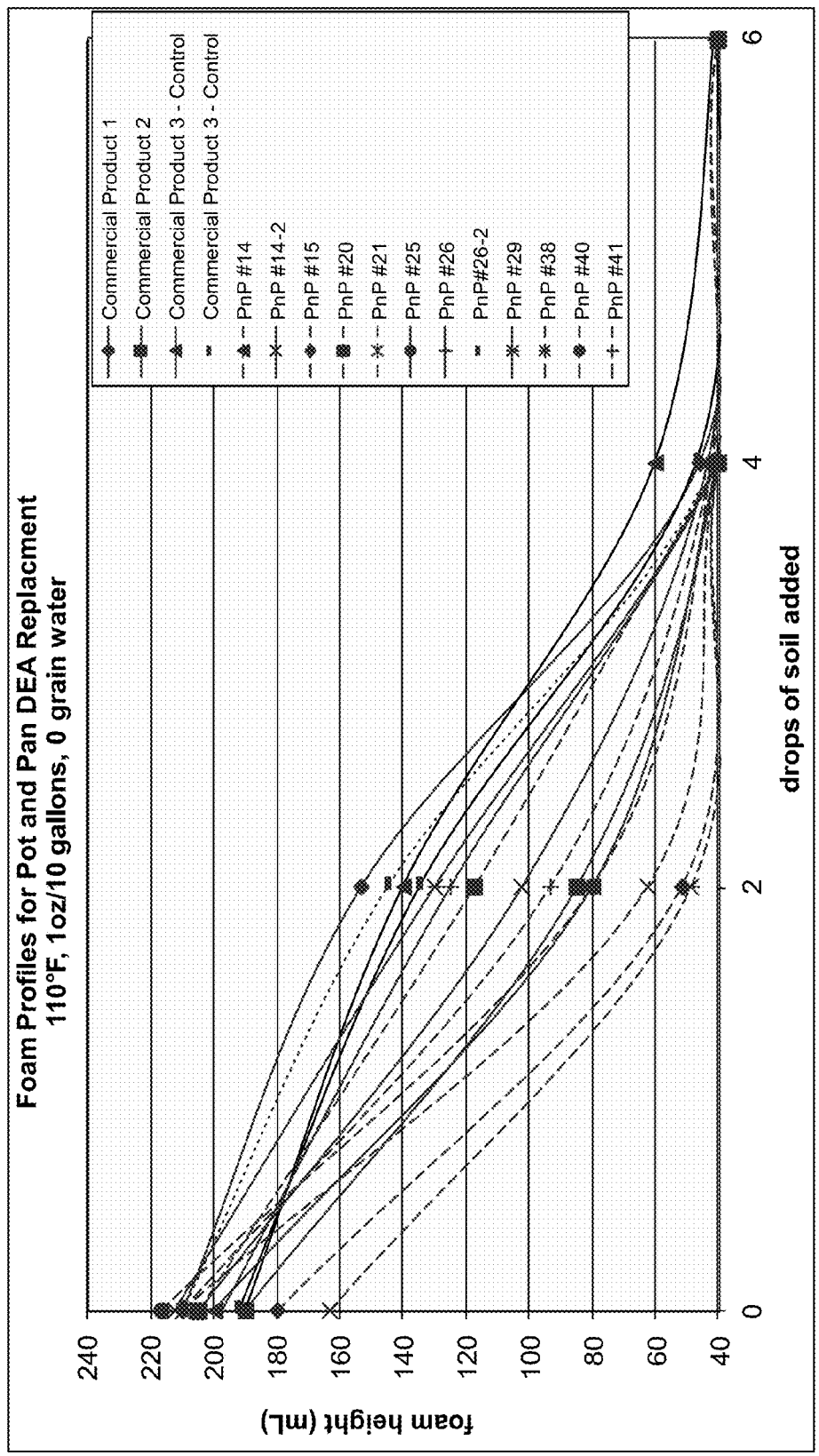
FIG. 4 is a graph depicting foam height as drops of soil are added for Commercial Products 1, 2, and 3, and formulas 14, 14-2, 15, 20, 21, 25, 26, 26-2, 29, 38, 40, and 41.
Figure 5:
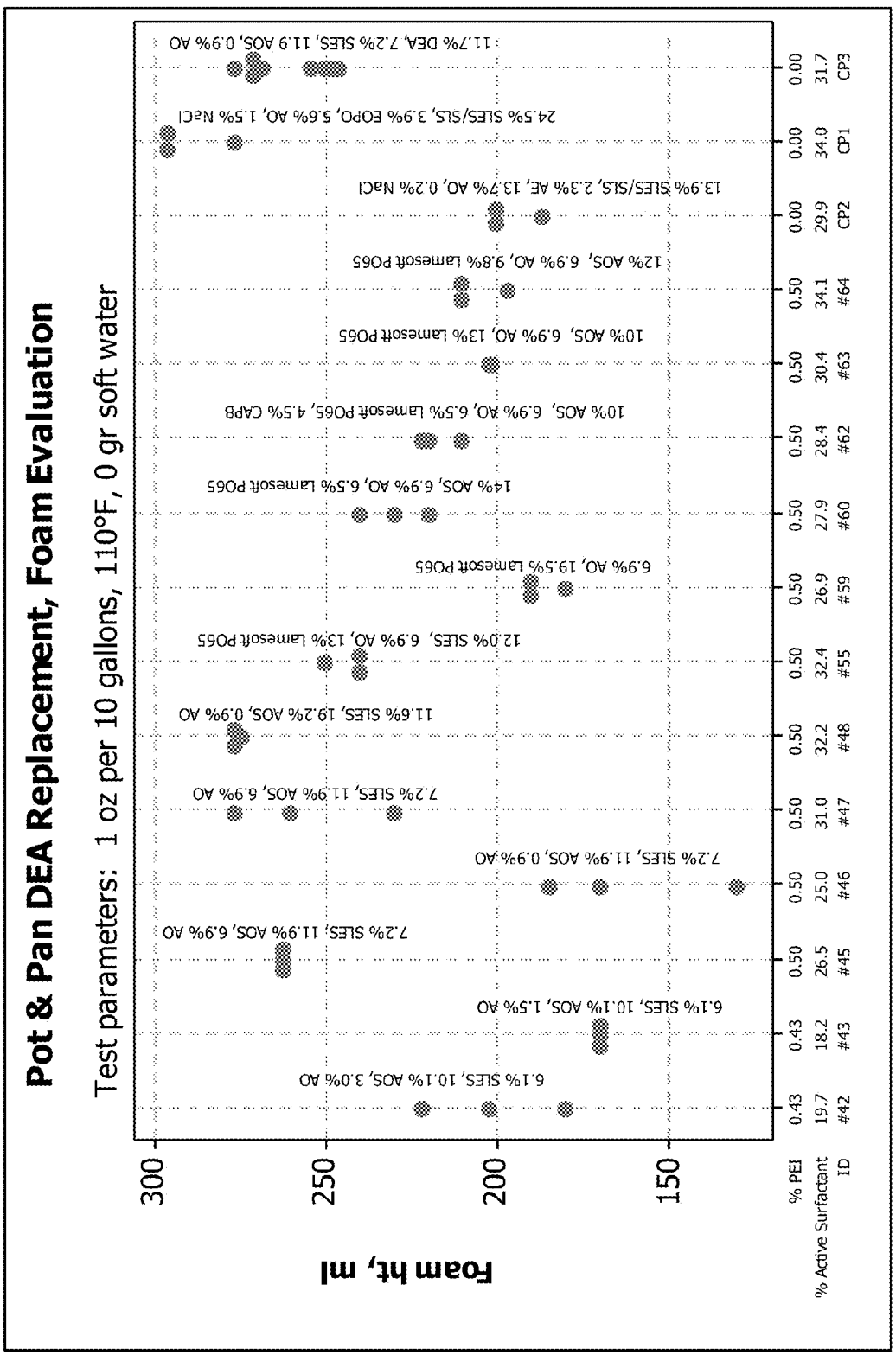
FIG. 5 is a graph depicting foam height of formulas 42, 43, 45, 46, 47, 48, 55, 59, 60, 62, 63, and 64 with commercially available foaming pot and pan cleaning products Commercial Product 1 and Commercial Product 2 (which include PEI-14 PEG-10/PPG-7) and Commercial Product 3.
Figure 6:
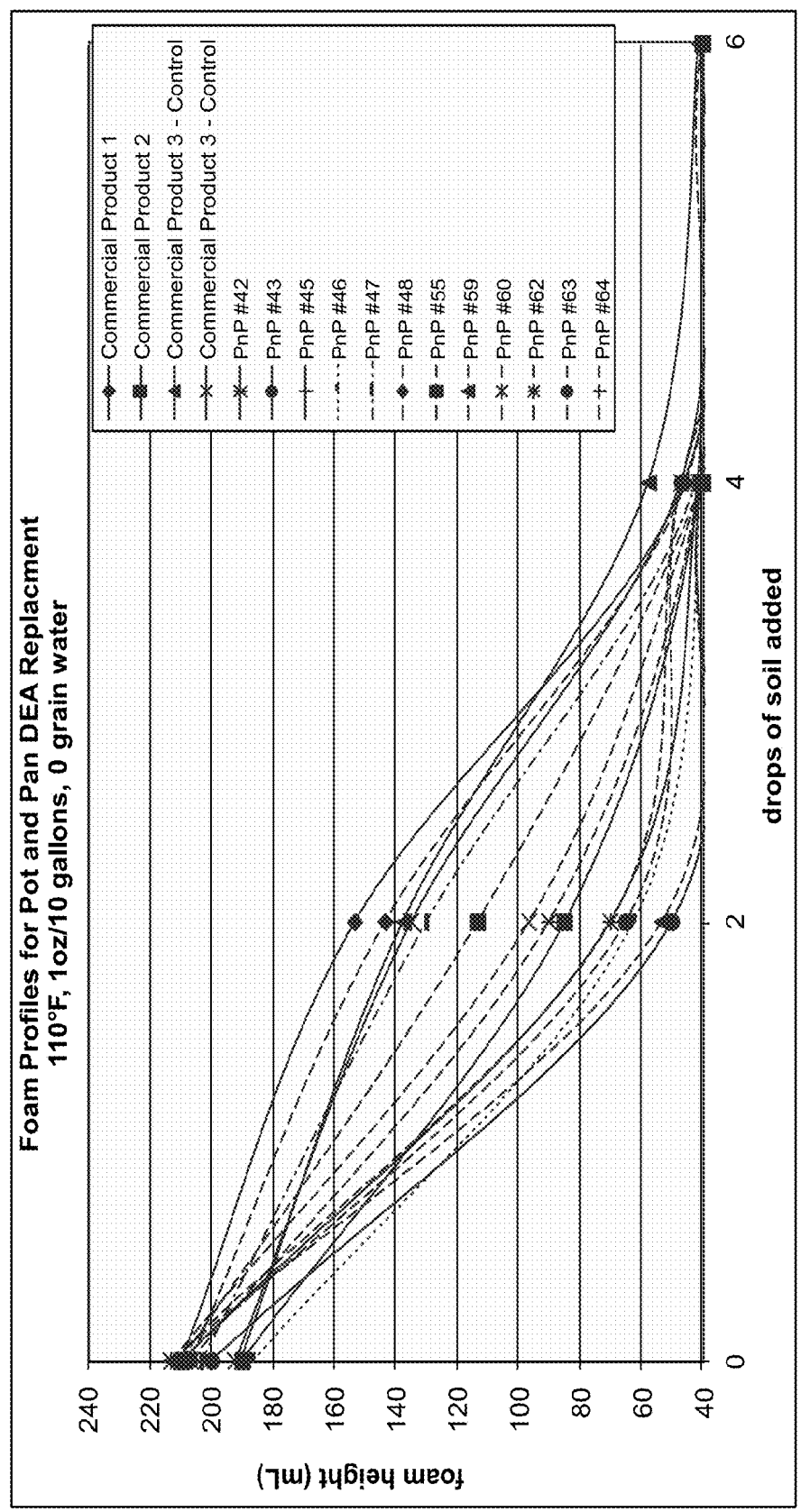
FIG. 6 is a graph depicting foam height as drops of soil are added for Commercial Product 1 and Commercial Product 2 (which include PEI-14 PEG-10/PPG-7) and Commercial Product 3, and formulas 42, 43, 45, 46, 47, 48, 55, 59, 60, 62, 63, and 64.
Figure 7:
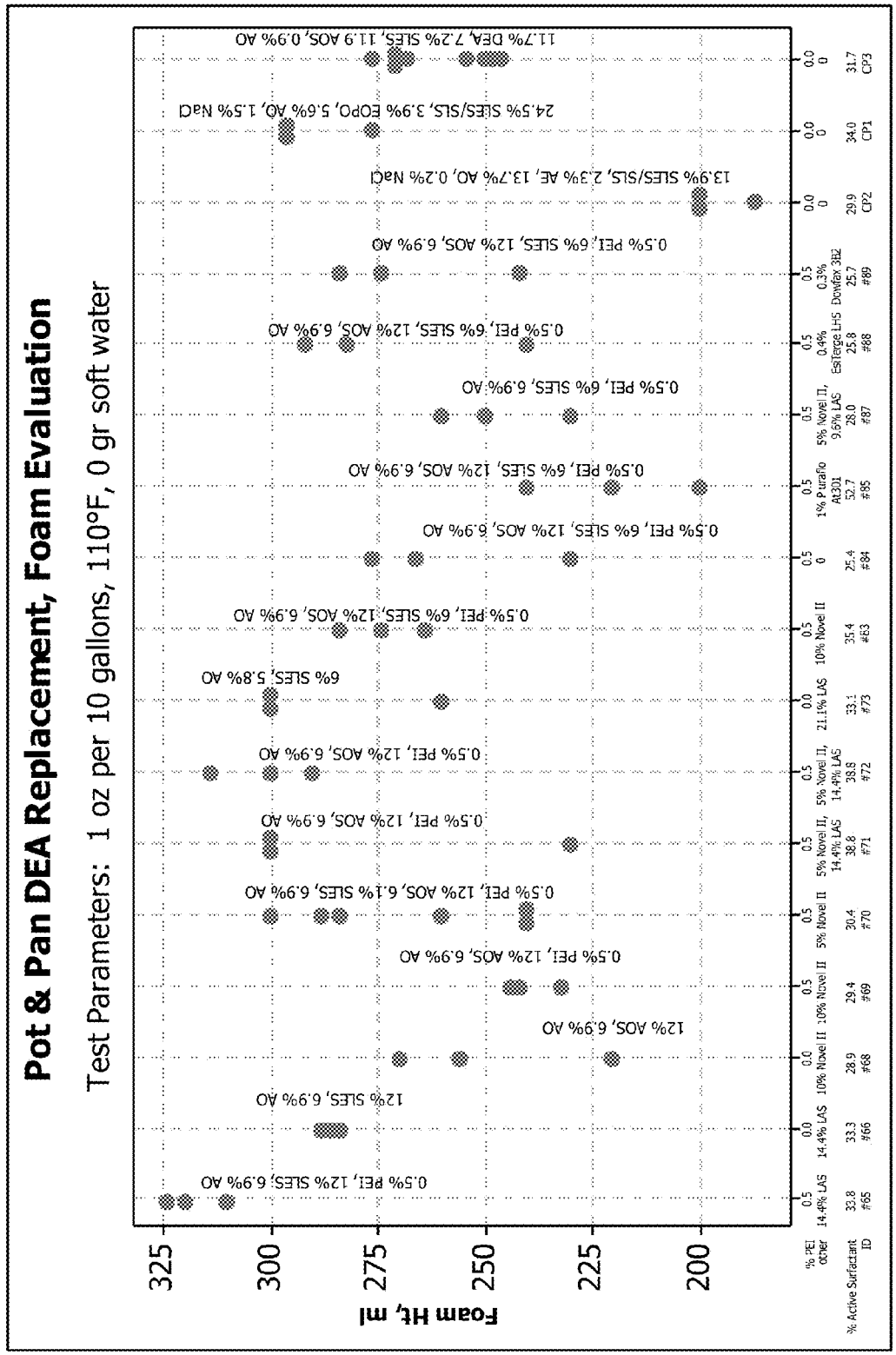
FIG. 7 is a graph depicting foam height of formulas 65, 66, 68, 69, 70, 71, 72, 73, 83, 84, 85, 87, 88, and 89 with commercially available foaming pot and pan cleaning products Commercial Product 1 and Commercial Product 2 (which include PEI-14 PEG-10/PPG-7) and Commercial Product 3.
Figure 8:
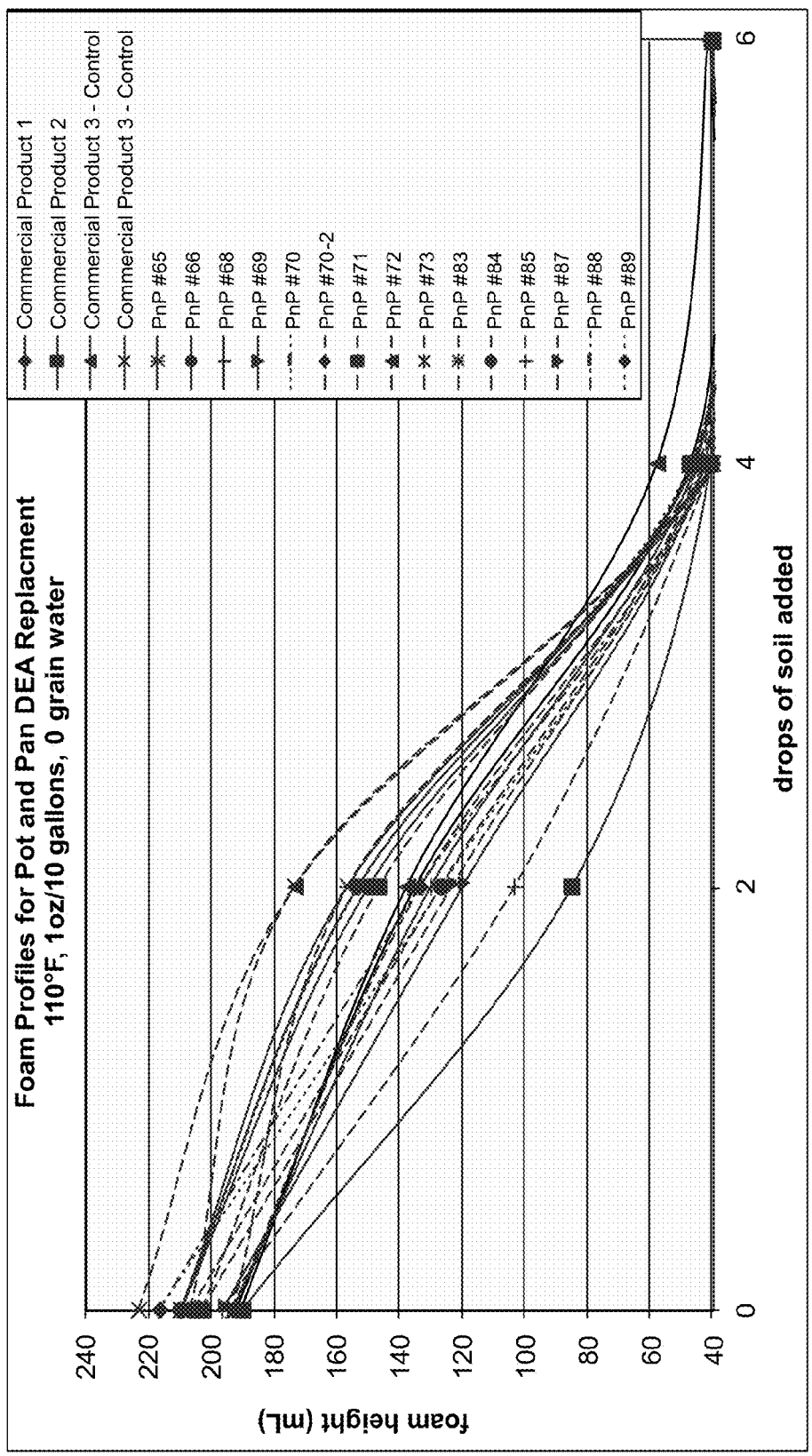
FIG. 8 is a graph depicting foam height as drops of soil are added for Commercial Product 1 and Commercial Product 2 (which include PEI-14 PEG-10/PPG-7) and Commercial Product 3, and formulas 65, 66, 68, 69, 70, 70-2, 71, 72, 73, 83, 84, 85, 87, 88, and 89.
Figure 9:
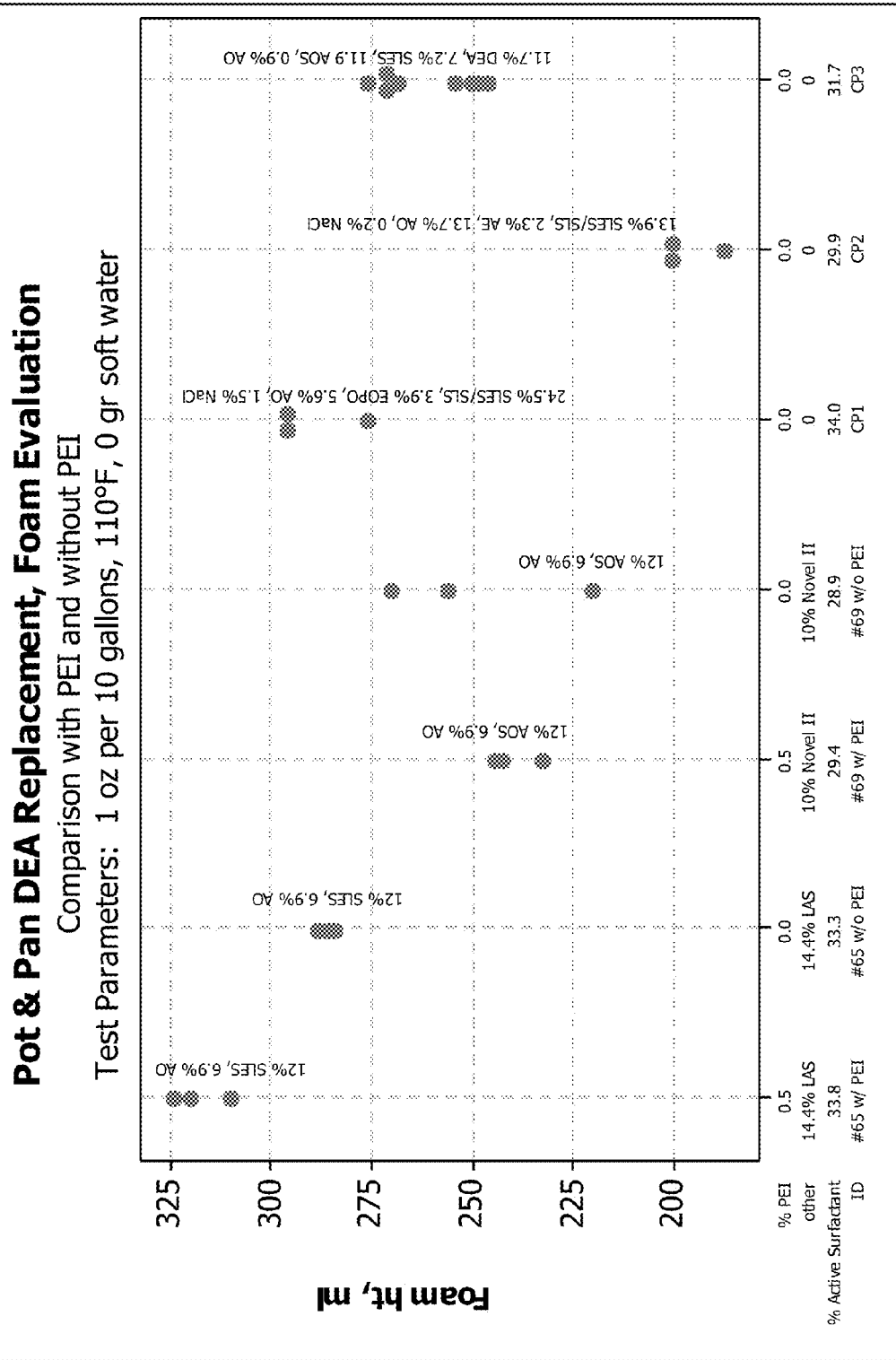
FIG. 9 is a graph depicting foam height of formula 65, without PEI and with PEI and formula 69 with and without PEI and with commercially available foaming pot and pan cleaning products Commercial Product 1 and Commercial Product 2 (which include PEI-14 PEG-10/PPG-7) and Commercial Product 3.
Figure 10:
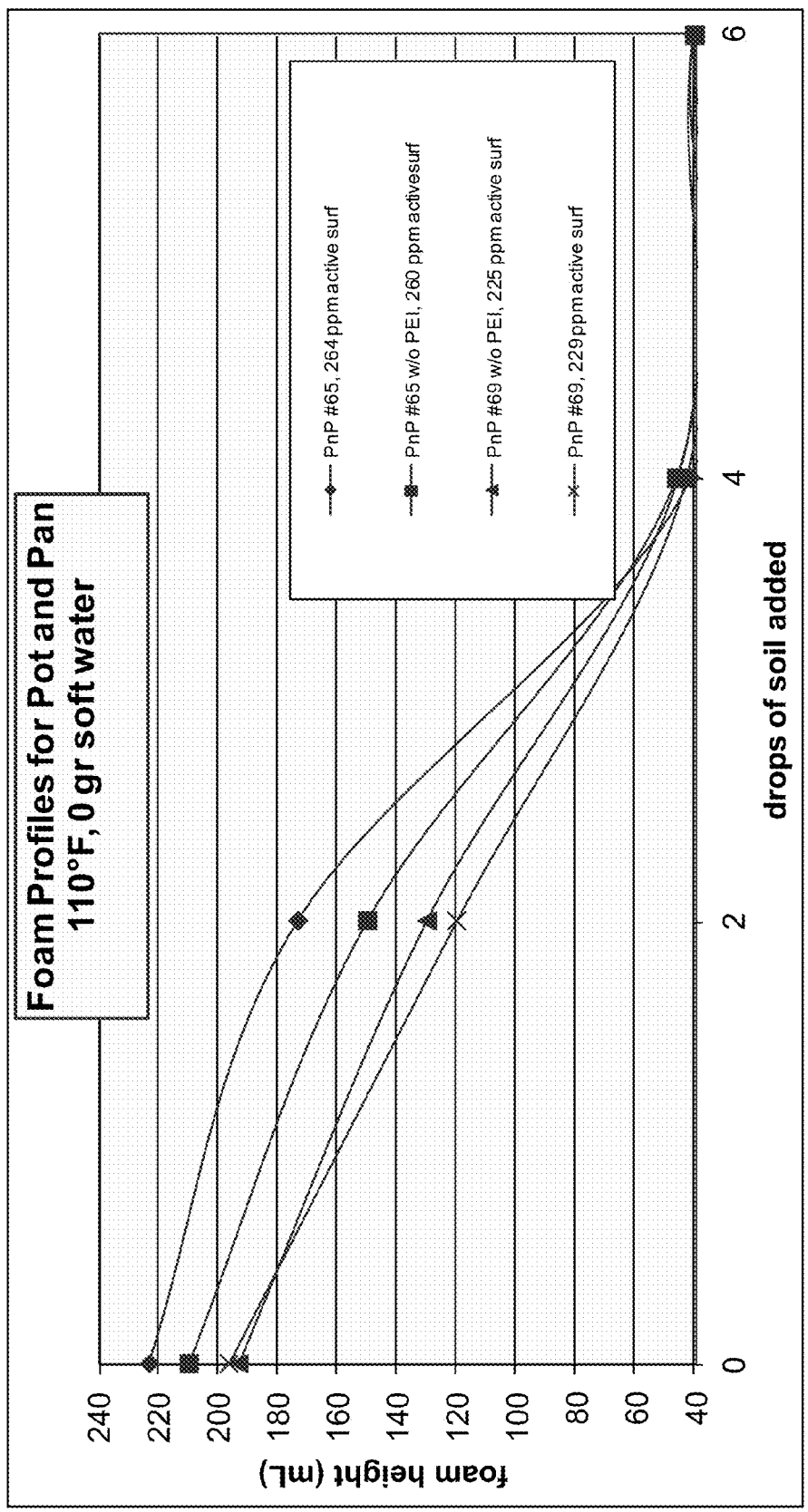
FIG. 10 is a graph depicting foam height as drops of soil are added for formula 65, without PEI and with PEI and formula 69 with and without PEI.

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

"Cleaning" means to perform or aid in soil removal, bleaching, microbial population reduction, rinsing, or combination thereof.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, "weight percent," "wt. %," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt. %," etc.

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers subsumed within that range (e.g., 1 to 5 includes 1, 1.5, 2, 2.75, 3, 3.80, 4, and 5).

DEFINITIONS

The term "commercially acceptable cleaning performance" refers generally to the degree of cleanliness, extent of effort, or both that a typical consumer would expect to achieve or expend when using a cleaning product or cleaning system to address a typical soiling condition on a typical substrate. This degree of cleanliness may, depending on the particular cleaning product and particular substrate, correspond to a general absence of visible soils, or to some lesser degree of cleanliness. For example, a shower cleaner or toilet bowl cleaner would be expected by a typical consumer to achieve an absence of visible soils when used on a moderately soiled but relatively new hard surface, but would not be expected to achieve an absence of visible soils when used on an old hard surface which already bears permanent stains such as heavy calcite deposits or iron discoloration. Cleanliness may be evaluated in a variety of ways depending on the particular cleaning product being used (e.g., ware or laundry detergent, rinse aid, hard surface cleaner, vehicular wash or rinse agent, or the like) and the particular hard or soft surface being cleaned (e.g., ware, laundry, fabrics, vehicles, and the like), and normally may be determined using generally agreed industry standard tests or localized variations of such tests. In the absence of such agreed industry standard tests, cleanliness may be evaluated using the test or tests already employed by a manufacturer or seller to evaluate the cleaning performance of its phosphorus-containing cleaning products sold in association with its brand.

The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both, when using the substitute cleaning product or substitute cleaning system rather than a branded phosphorus-containing cleaning to address a typical soiling condition on a typical substrate. This degree of cleanliness may, depending on the particular cleaning product and particular substrate, correspond to a general absence of visible soils, or to some lesser degree of cleanliness, as explained in the prior paragraph.

The term "hard surface" refers to a non-resilient cleanable substrate, for example materials made from ceramic, stone, glass or hard plastics including showers, sinks, toilets, bathtubs, countertops, windows, mirrors, transportation vehicles, walls, wooden or tile floors, patient-care equipment (for example diagnostic equipment, shunts, body scopes, wheel chairs, bed frames, etc.), surgical equipment and the like.

The term "improved cleaning performance" refers generally to achievement by a substitute cleaning product or substitute cleaning system of a generally greater degree of cleanliness or with generally a reduced expenditure of effort, or both, when using the substitute cleaning product or substitute cleaning system rather than a branded phosphorus-containing cleaning product to address a typical soiling condition on a typical substrate. This degree of cleanliness may, depending on the particular cleaning product and particular substrate, correspond to a general absence of visible soils, or to some lesser degree of cleanliness, as explained above.

The terms "include" and "including" when used in reference to a list of materials refer to but are not limited to the materials so listed.

The term "soft surface" refers to a resilient cleanable substrate, for example materials made from woven, nonwoven or knit textiles, leather, rubber or flexible plastics including fabrics (for example surgical garments, draperies, bed linens, bandages, etc.), carpet, transportation vehicle seating and interior components and the like.

The term "solid" refers to a composition in a generally shape-stable form under expected storage conditions, for example a powder, particle, agglomerate, flake, granule, pellet, tablet, lozenge, puck, briquette, brick or block, and whether in a unit dose or a portion from which measured unit doses may be withdrawn. A solid may have varying degrees of shape stability, but typically will not flow perceptibly and will substantially retain its shape under moderate stress, pressure or mere gravity, as for example, when a molded solid is removed from a mold, when an extruded solid exits an extruder, and the like. A solid may have varying degrees of surface hardness, and for example may range from that of a fused solid block whose surface is relatively dense and hard, resembling concrete, to a consistency characterized as being malleable and sponge-like, resembling a cured caulking material.

The term "water soluble" refers to a compound that can be dissolved in water at a concentration of more than 1 wt. %. The terms "sparingly soluble" or "sparingly water soluble" refer to a compound that can be dissolved in water only to a concentration of 0.1 to 1.0 wt. %. The term "water insoluble" refers to a compound that can be dissolved in water only to a concentration of less than 0.1 wt. %.

Compositions of the Invention

Positively Charged Polymer

According to the invention, the positively charged class of polymers such as polyethyleneimine (PEI) and its derivatives such as ethoxylated (PEI) polymers, polyamines, polyquats, polyglycerol quats, and other PEI derivatives, their salts or mixtures may use in the compositions of the invention. PEI is a polymeric amine or a polyamine, and include, polyethyleneimine compounds (PEI) and/or its derivatives. Polyethyleneimines may include primary, secondary or tertiary amine compounds. The polyethyleneimine compounds and/or its derivatives may include linear and/or branched polyethyleneimines. Still further, polyethyleneimines and/or its derivatives can vary significantly in molecular weight, topology and shape, including for example linear, branched or comb-like structures as a result of ring-opening polymerization of the ethylenimine. See Angelescu et al., *Langmuir*, 27, 9961-9971 (2011), which is incorporated herein by reference in its entirety. According to an aspect of the invention, the bleach activator may be a linear and/or branched polyethyleneimine.

Linear polyethyleneimines are made by the cationic polymerization of oxazoline and oxazine derivatives. Methods for preparing linear PEIs are more fully described in Advances in Polymer Science, Vol. 102, pgs. 171-188, 1992 (references 6-31) which is incorporated in its entirety herein by reference. Polyethyleneimines can also be made by the polymerization of aziridine to afford a polymeric amine often containing primary, secondary, and tertiary amine functionality. Commercial preparation of PEIs are generally acid-catalyzed reactions to open the ring of ethyleneimine, also known as aziridine as shown below:

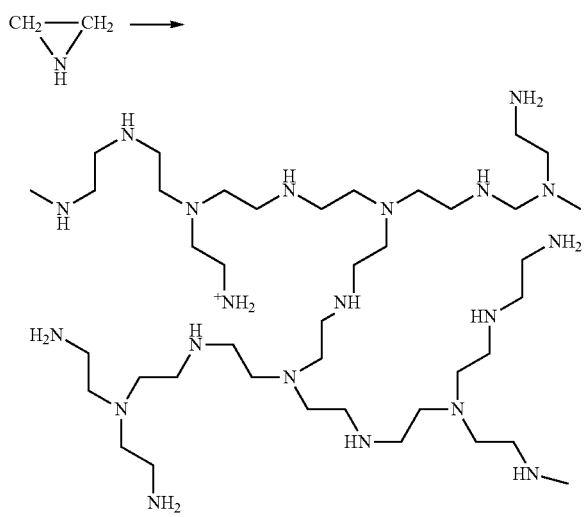

Often the commercial production of ethyleneimine, which is subsequently catalyzed to open to form PEIs, is prepared through sulfuric acid esterification of ethanolamine, such as shown below:

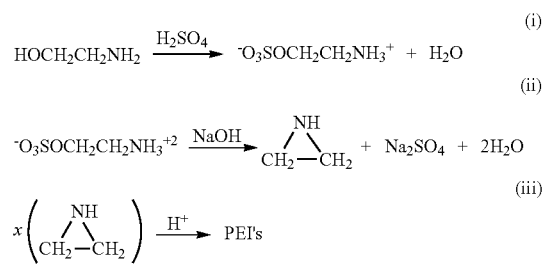

Suitable polyethyleneimine compounds useful in the present invention may contain a mixture of primary, secondary, and tertiary amine substituents. The mixture of primary, secondary, and tertiary amine substituents may be in any ratio, including for example in the ratio of about 1:1:1 to about 1:2:1 with branching every 3 to 3.5 nitrogen atoms along a chain segment. Alternatively, suitable polyethyleneimine compounds may be primarily one of primary, secondary or tertiary amine substituents.

Exemplary PEI products include multifunctional cationic polyethyleneimines with branched polymer structures according to the following formulas (—($CH_2$—$CH_2$—$NH$)$_n$—), with a molecular mass of 43.07 (as repeating units).

In certain aspects the formula (—(CH$_2$—CH$_2$—NH)$_n$—) has a value of n that is at least 10 to 10$^5$, and wherein the nitrogen to carbon ratio is 1:2. PEI polymers have the general following polymer structure:

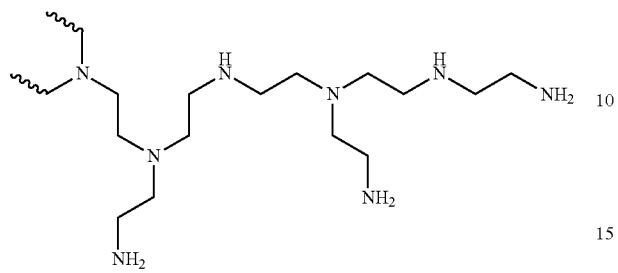

PEI products can also be represented by the following general formula, which may vary according to substitutions, size, molecular weight, branching, and the like:

wherein x is an integer that is 1 or greater and y is an integer that is 1 or greater than 1. Preferably, wherein x is an integer from about 1 to about 120,000, preferably from about 2 to about 60,000, more preferably from about 3 to about 24,000 and y is an integer from about 1 to about 60,000, preferably from about 2 to about 30,000, more preferably from about 3 to about 12,000.

Various commercial polyethyleneimines are available, including for example those sold under the tradename Lupasol® (BASF), including for example Lupasol® FG, Lupasol® G, Lupasol® PR 8515, Lupasol® WF, Lupasol® G 20/35/100, Lupasol® HF, Lupasol® P, Lupasol® PS, Lupasol® PO 100, Lupasol® PN 50/60, and Lupasol® SK. Such exemplary polyethyleneimines are available as anhydrous polyethyleneimines and/or modified polyethyleneimines provided in aqueous solutions or methoyxypropanol (Lupasol® PO 100). The molar mass of the polyethyleneimines, including modified polyethyleneimines can vary from about 800 g/mol to at least 2,000,000 g/mol.

In certain aspects the polymeric amine bleach activators, and preferably the PEI bleach activators, may be a branched, spherical polymeric amine. In further aspects, the molecular weight of the polymeric amine bleach activators or PEI bleach is from about 100 Daltons to about 2 million Daltons (PEI-2,000,000), more preferably from about 100 Daltons to about 1 million Daltons (PEI-1,000,000), more preferably from about 500 Daltons to about 500 kDa (PEI-500,000), more preferably from about 500 Daltons to about 50 kDa (PEI-50,000), more preferably from about 800 Daltons to about 50 kDa (PEI-50,000), more preferably from about 800 Daltons to about 10 kDa (PEI-10,000). In further aspects, the charge density of the PEI or PEI salt is from about 15 meq/g to about 25 meq/g, more preferably from about 16 meq/g to about 20 meq/g. Commercially-available examples of such preferred PEIs include the BASF products LUPASOL® WF (25 kDa; 16-20 meq/g) and Lupasol® FG (800 Daltons; 16-20 meq/g), and the BASF products in the SOKALAN® family of polymers, e.g., SOKALAN® HP20, SOKALAN® HP22 G, and the like.

In an aspect, a polymeric amine may contain other substituents and/or copolymers. For example, a polymeric amine may also include substituents, including for example ethoxylates and propoxylates. In an aspect of the invention, the polymeric amine, such as a polyethyleneimines, are derivatized with ethylene oxide (EO) and/or propylene oxide (PO) side chains. According to the invention, the PEI does not contain propylene oxide side chains. In an exemplary aspect of the invention ethoxylated PEIs may be heavily branched, wherein the substitutable hydrogens on the primary and secondary nitrogens are replaced with ethoxylated chains containing varying degrees of repeating units, such as the following polymer structure (generic for PEI$_{20}$EO):

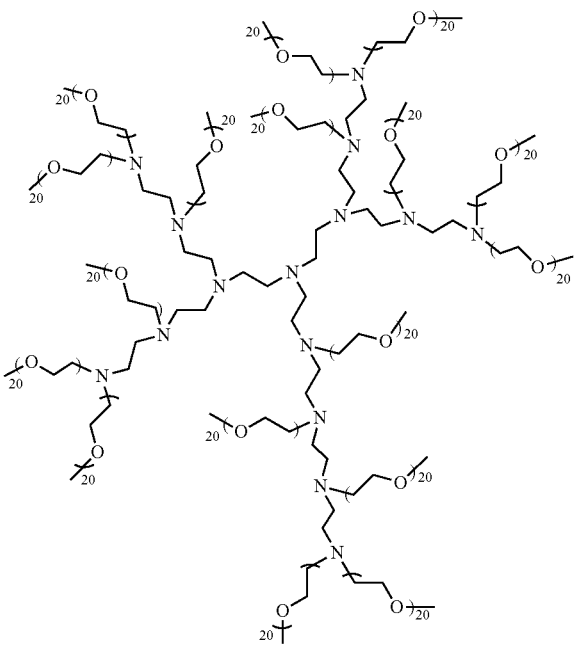

In an aspect, the bleach activator is a polyethyleneimine polymer with ethyleneoxide chains. Ethoxylation of PEIs increases the solubility of the bleach activator according to the invention.

A polymeric amine may also include copolymers, including for example ethylenediamine. A variety of substituents and/or copolymers may be included in order to modify the solubility or any other physical characteristics of a particular polymeric amine employed as a bleach activator according to the invention.

Because of the presence of amine groups, PEI can be protonated with acids to form a PEI salt from the surrounding medium resulting in a product that is partially or fully ionized depending on pH. For example, about 73% of PEI is protonated at pH 2, about 50% of PEI is protonated at pH 4, about 33% of PEI is protonated at pH 5, about 25% of PEI is protonated at pH 8 and about 4% of PEI is protonated at pH 10. In general, PEIs can be purchased as their protonated or unprotonated form with and without water. An example of a segment of a branched protonated polyethyleneimine (PEI salt) is shown below:

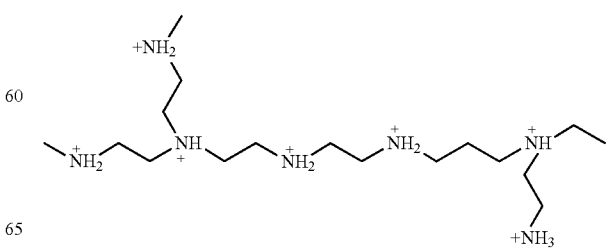

The counterion of each protonated nitrogen center is balanced with an anion of an acid obtained during neutralization. Examples of protonated PEI salts include, but are not limited to, PEI-hydrochloride salt, PEI-sulfuric acid salt, PEI-nitric acid salt, PEI-acetic acid salt PEI fatty acid salt and the like. In fact, any acid can be used to protonate PEIs resulting in the formation of the corresponding PEI salt compound.

The cationic polymer, PEI is present in an amount of from about 0.01 wt. % 1 to about 5 wt. %. At greater than 5 wt. % the affect is decreased and this is a critical upper limit.

Anionic Surfactants

The invention contemplates the use of one or more anionic surfactants which electrostatically interact or ionically interact with the positively charged polymer to enhance foam stability. Anionic surfactants are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility.

As those skilled in the art understand, anionics are excellent detersive surfactants and are therefore traditionally favored additions to heavy duty detergent compositions. Generally, anionics have high foam profiles which are useful for the present foaming cleaning compositions. Anionic surface active compounds are useful to impart special chemical or physical properties other than detergency within the composition.

The majority of large volume commercial anionic surfactants can be subdivided into five major chemical classes and additional sub-groups known to those of skill in the art and described in "Surfactant Encyclopedia," Cosmetics & Toiletries, Vol. 104 (2) 71-86 (1989).

The first class includes acylamino acids (and salts), such as acylgluamates, acyl peptides, sarcosinates (e.g. N-acyl sarcosinates), taurates (e.g. N-acyl taurates and fatty acid amides of methyl tauride), and the like. The second class includes carboxylic acids (and salts), such as alkanoic acids (and alkanoates), ester carboxylic acids (e.g. alkyl succinates), ether carboxylic acids, and the like. The third class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. A particularly preferred anionic surfactant is alpha olefin sulfonate. The fourth class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. The fifth class includes sulfuric acid esters (and salts), such as alkyl ether sulfates, alkyl sulfates, and the like. The fifth class includes sulfuric acid esters (and salts), such as alkyl ether sulfates, alkyl sulfates, and the like. A particularly preferred anionic surfactant is sodium laurel ether sulfate.

Anionic sulfate surfactants suitable for use in the present compositions include the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside (the nonionic nonsulfated compounds being described herein). Ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives.

Anionic carboxylate surfactants suitable for use in the present compositions include the alkyl ethoxy carboxylates, the alkyl polyethoxy polycarboxylate surfactants and the soaps (e.g. alkyl carboxyls). Secondary soap surfactants (e.g. alkyl carboxyl surfactants) useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary soap surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present.

Other anionic detergents suitable for use in the present compositions include olefin sulfonates, such as long chain alkene sulfonates, long chain hydroxyalkane sulfonates or mixtures of alkenesulfonates and hydroxyalkane-sulfonates. Also included are the alkyl sulfates, alkyl poly(ethyleneoxy) ether sulfates and aromatic poly(ethyleneoxy)sulfates such as the sulfates or condensation products of ethylene oxide and nonyl phenol (usually having 1 to 6 oxyethylene groups per molecule). Resin acids and hydrogenated resin acids are also suitable, such as rosin, hydrogenated rosin, and resin acids and hydrogenated resin acids present in or derived from tallow oil.

The particular salts will be suitably selected depending upon the particular formulation and the needs therein.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Anionic surfactants are present in the composition in any detersive amount which can range typically from about 1 wt. % to about 75 wt. % of the cleaning composition. In a preferred embodiment, about 5 wt. % to about 65 wt. % and more preferably from about 15 wt. % to about 60 wt. %.

Amphoteric Surfactant (Amine Oxide, Betaines and Sultaines)

The invention also include amphoteric and/or zwitterionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Preferred semi-polar nonionic detergent surfactants are the amine oxide surfactants having the formula:

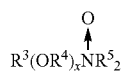

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. $R^5$ groups can be attached to each other, e.g., through an oxygen or nitrogen atom, to form a ring structure.

Preferred amine oxide surfactants are $C_{10}$-$C_{18}$ alkyldimethylamine oxides and $C_8$-$C_{12}$ alkoxyethyldihydroxyethylamine oxides. Other amphoteric surfactants as described herein may also be used according to the invention. Applicants found that the amphoteric surfactant, (preferably amine oxide) cannot be present in an amount greater than 8 wt. % active. Typical ranges of the same would include from about 0 wt. % active to about 7.99 wt. % active, preferably from about 0.1-7 wt. % active and most preferably from about 2 wt. % active to about 6 wt. % active.

The invention also includes the zwitterionic class of amphoteric surfactants.

Zwitterionic Surfactants

Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion, a negative charged carboxyl group, and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

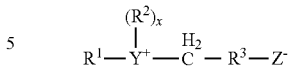

wherein R1 contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-car-boxylate; 5-[S-3-hydroxypropyl-S-hexadecylsulfonio]-3-hydroxypentane-1-sul-fate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propan-e-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N (2-hydroxydodecyl)ammonio]-butane-1-carboxyl-ate; 3-[S-ethyl-S-(3-dodecoxy-2-hydroxypropyl)sulfonio]-propane-1-phosphat-e; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

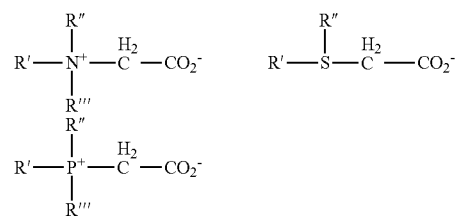

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R1)_2N.\text{sup.}+R^2SO^3-)$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Betaines and sultaines and other such zwitterionic surfactants are present in an amount of from Anionic surfactants are present in the composition in any detersive amount which can range typically from about 0.01 wt. % to about 75 wt. % of the cleaning composition. In a preferred embodiment, about 10 wt. % to about 30 wt. % and more preferably from about 15 wt. % to about 25 wt. %.

Additional Materials

The compositions may also include additional materials, such as additional functional materials, for example enzymes, enzyme stabilizing system, additional surfactant, chelating agents, sequestering agents, bleaching agents, additional thickening agent, solubility modifier, detergent filler, anti-redeposition agent, a threshold agent or system, aesthetic enhancing agent (i.e. dye, perfume, etc.) and the like, or combinations or mixtures thereof. Adjuvants and other additive ingredients will vary according to the type of composition being manufactured and can be included in the compositions in any amount. The following is a brief discussion of some examples of such additional materials.

Additional Surfactant

Additional surfactants may be present in some compositions embodying the invention in addition to those described supra. The additional surfactant or surfactant admixture can be selected from nonionic (supra), semi-polar nonionic, anionic (supra), cationic, amphoteric, or zwitterionic surface-active agents; or any combination thereof. In at least some embodiments, the surfactants are water soluble or water dispersible. The particular surfactant or surfactant mixture chosen for use in the process and products of this invention can depend on the conditions of final utility, including method of manufacture, physical product form, use pH, use temperature, foam control, and soil type. For a discussion of surfactants, see Kirk-Othmer, Encyclopedia of Chemical Technology, Third Edition, volume 8, pages 900-912. The composition may include additional surfactant a surfactant in an amount effective to provide a desired level of cleaning, such as 0-20 wt. %, or 1.5-15 wt. %. A discussion of examples of different types of surfactants not already addressed follows hereinafter.

Nonionic Surfactants

The surfactant is preferably a nonionic surfactant. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amino group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants in the present invention include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp.

Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from 1,000 to 4,000. Ethylene oxide is then added to sandwich this hydrophobe between hydrophilic groups, controlled by length to constitute from about 10% by weight to about 80% by weight of the final molecule.

Tetronic® compounds are tetra-functional block copolymers derived from the sequential addition of propylene oxide and ethylene oxide to ethylenediamine. The molecular weight of the propylene oxide hydrotype ranges from 500 to 7,000; and, the hydrophile, ethylene oxide, is added to constitute from 10% by weight to 80% by weight of the molecule.

2. Condensation products of one mole of alkyl phenol wherein the alkyl chain, of straight chain or branched chain configuration, or of single or dual alkyl constituent, contains from 8 to 18 carbon atoms with from 3 to 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Polyethylene sorbitan fatty acid esters with the esterifying fatty acid being selected from the group consisting of $C_{12}$-$C_{18}$ fatty acids wherein an average of about 1 or 3 of said acids are esterified per polyoxyethylene sorbitan molecule. One preferred non-ionic surfactant is a mixture of laurate esters of sorbitol and sorbitol anhydrides (sorbitan) consisting predominantly of the mono-ester condensed with about 20 moles of ethylene oxide. This surfactant is designated in the CTFA dictionary as Polysorbate 20 and is also known in the art as polyoxyethylene (20) sorbitan monolaurate and is available from several commercial sources. Another suitable example of a polyoxyethylene alkyl ester is the CTFA designated Polysorbate 80 which is a mixture of oleate esters of sorbitol and sorbitol anhydrides, condensed with approximately 80 moles of ethylene oxide In a preferred embodiment the surfactant is a sorbitan ester.

4. Condensation products of one mole of a saturated or unsaturated, straight or branched chain alcohol having from 6 to 24 carbon atoms with from 3 to 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co. and Alfonic® manufactured by Vista Chemical Co.

5. Condensation products of one mole of saturated or unsaturated, straight or branched chain carboxylic acid having from 8 to 18 carbon atoms with from 6 to 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol® manufactured by Henkel Corporation and Lipopeg® manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances.

Examples of Nonionic Low Foaming Surfactants Include:

6. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from 1,000 to 3,100 with the central hydrophile including 10% by weight to 80% by weight of the final molecule. These reverse Pluronics® are manufactured by BASF Corporation under the trade name Pluronic® R surfactants.

Likewise, the Tetronic® R surfactants are produced by BASF Corporation by the sequential addition of ethylene oxide and propylene oxide to ethylenediamine. The hydrophobic portion of the molecule weighs from 2,100 to 6,700 with the central hydrophile including 10% by weight to 80% by weight of the final molecule.

7. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

8. The alkylphenoxypolyethoxyalkanols of U.S. Pat. No. 2,903,486 issued Sep. 8, 1959 to Brown et al. and represented by the formula

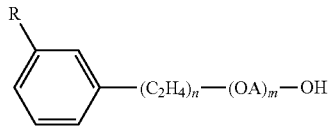

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from 1 to 6 carbon atoms and one reactive hydrogen atom, n has an average value of at least 6.4, as determined by hydroxyl number and m has a value such that the oxyethylene portion constitutes 10% to 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n(C_2H_4O)_mH]_x$ wherein Y is the residue of an organic compound having from 2 to 6 carbon atoms and containing x reactive hydrogen atoms in which x has a value of at least 2, n has a value such that the molecular weight of the polyoxypropylene hydrophobic base is at least 900 and m has value such that the oxyethylene content of the molecule is from 10% to 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from 8 to 18 carbon atoms and containing x reactive hydrogen atoms in which x has a value of 1 or 2, n has a value such that the molecular weight of the polyoxyethylene portion is at least 44 and m has a value such that the oxypropylene content of the molecule is from 10% to 90% by weight. In either case the oxypropylene chains may contain optionally, but advantageously, small amounts of ethylene oxide and the oxyethylene chains may contain also optionally, but advantageously, small amounts of propylene oxide.

9. Polyhydroxy fatty acid amide surfactants suitable for use in the present compositions include those having the structural formula $R^2CONR^1Z$ in which: $R^1$ is H, $C_1$-$C_4$ hydrocarbyl, 2-hydroxy ethyl, 2-hydroxy propyl, ethoxy, propoxy group, or a mixture thereof; R is a $C_5$-$C_3$1 hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

10. The alkyl ethoxylate condensation products of aliphatic alcohols with from 0 to 25 moles of ethylene oxide are suitable for use in the present compositions. The alkyl chain of the aliphatic alcohol can either be straight or branched, primary or secondary, and generally contains from 6 to 22 carbon atoms.

11. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_{10}$-$C_{18}$ ethoxylated fatty alcohols with a degree of ethoxylation of from 3 to 50.

12. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from 6 to 30 carbon atoms and a polysaccharide, e.g., a polyglycoside, hydrophilic group containing from 1.3 to 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

13. Fatty acid amide surfactants suitable for use in the present compositions include those having the formula: $R^6CON(R^7)_2$ in which $R^6$ is an alkyl group containing from 7 to 21 carbon atoms and each $R^7$ is independently hydrogen, $C_1$-$C_4$ alkyl, $C_1$-$C_4$ hydroxyalkyl, or —$(C_2H_4O)_xH$, where x is in the range of from 1 to 3.

14. A useful class of non-ionic surfactants includes the class defined as alkoxylated amines or, most particularly, alcohol alkoxylated/aminated/alkoxylated surfactants. These non-ionic surfactants may be at least in part represented by the general formulae:

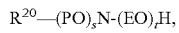

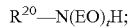

in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula:

in which $R^{20}$ is as defined above, v is 1 to 20 (e.g., 1, 2, 3, or 4 (preferably 2)), and w and z are independently 1-10, preferably 2-5.

These compounds are represented commercially by a line of products sold by Huntsman Chemicals as nonionic surfactants. A preferred chemical of this class includes Surfonic™ PEA 25 Amine Alkoxylate.

15. Extended chain surfactants having an intermediate polarity linking chain, such as a block of poly-propylene oxide, or a block of poly-ethylene oxide, or a block of poly-butylene oxide or a mixture thereof inserted between the surfactant's conventional lipophilic segment and hydrophilic segment.

The treatise Nonionic Surfactants, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Semi-Polar Nonionic Surfactants

The semi-polar type of nonionic surface active agents is another class of nonionic surfactant useful in compositions of the present invention. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

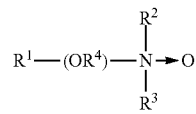

wherein the arrow is a conventional representation of a semi-polar bond; and $R^1$, $R^2$, and $R^3$ may be aliphatic, aromatic, heterocyclic, alicyclic, or combinations thereof. Generally, for amine oxides of detergent interest, R' is an alkyl radical of from 8 to 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to 20.

Useful water soluble amine oxide surfactants are selected from the coconut or tallow alkyl di-(lower alkyl) amine oxides, specific examples of which are dodecyldimethylamine oxide, tridecyldimethylamine oxide, tetradecyldimethylamine oxide, pentadecyldimethylamine oxide, hexadecyldimethylamine oxide, heptadecyldimethylamine oxide, octadecyldimethylamine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

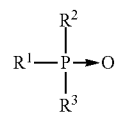

wherein the arrow is a conventional representation of a semi-polar bond; and $R^1$ is an alkyl, alkenyl or hydroxyalkyl moiety ranging from 10 to 24 carbon atoms in chain length; and $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphine oxide, dimethylhexadecylphosphine oxide, diethyl-2-hydroxyoctyldecylphosp-hine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

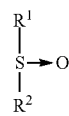

wherein the arrow is a conventional representation of a semi-polar bond; and, $R^1$ is an alkyl or hydroxyalkyl moiety of 8 to 28 carbon atoms, from 0 to 5 ether linkages and from 0 to 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dode-coxybutyl methyl sulfoxide.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Cationic Surfactants

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure RnX+Y—and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

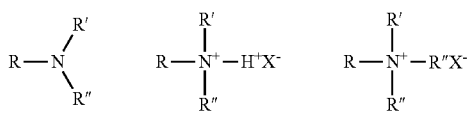

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those of skill in the art and described in "Surfactant Encyclopedia," Cosmetics & Toiletries, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1{}_m R^2{}_x YLZ$ wherein each $R^1$ is an organic group containing a straight or branched alkyl or alkenyl group optionally substituted with up to three phenyl or hydroxy groups and optionally interrupted by up to four of the following structures:

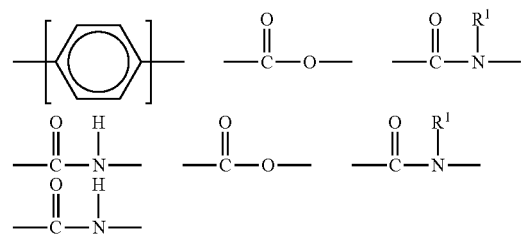

or an isomer or mixture of these structures, and which contains from 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2, or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group is filled by hydrogens.

Y can be a group including, but not limited to:

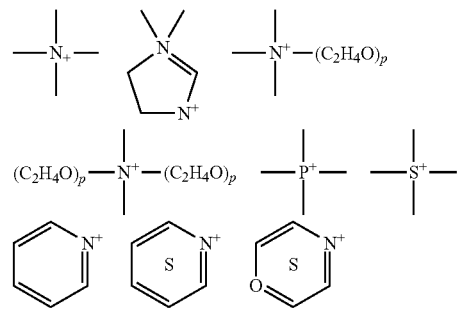

p = about 1 to 12 or a mixture thereof.

Preferably, L is 1 or 2, with the Y groups being separated by a moiety selected from $R^1$ and $R^2$ analogs (preferably alkylene or alkenylene) having from 1 to 22 carbon atoms and two free carbon single bonds when L is 2. Z is a water soluble anion, such as sulfate, methylsulfate, hydroxide, or nitrate anion, particularly preferred being sulfate or methyl sulfate anions, in a number to give electrical neutrality of the cationic component.

Amphoteric Surfactants

Amphoteric, or ampholytic, surfactants contain both a basic and an acidic hydrophilic group and an organic hydrophobic group. These ionic entities may be any of the anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia," Cosmetics & Toiletries, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

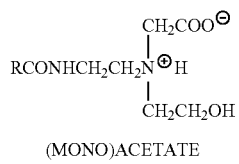

(MONO)ACETATE

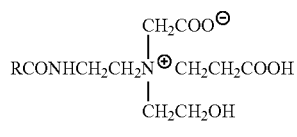

(DI)PROPIONATE

Neutral pH-Zwitterion

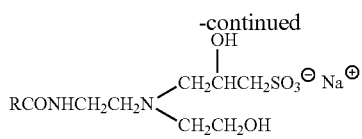

AMPHOTERIC SULFONATE wherein R is an acyclic hydrophobic group containing from 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Preferred amphocarboxylic acids are produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reacting $RNH_2$, in which R.dbd.$C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In these, R is preferably an acyclic hydrophobic group containing from 8 to 18 carbon atoms, and M is a cation to neutralize the charge of the anion.

Preferred amphoteric surfactants include those derived from coconut products such as coconut oil or coconut fatty acid. The more preferred of these coconut derived surfactants include as part of their structure an ethylenediamine moiety, an alkanolamide moiety, an amino acid moiety, preferably glycine, or a combination thereof; and an aliphatic substituent of from 8 to 18 (preferably 12) carbon atoms. Such a surfactant can also be considered an alkyl amphodicarboxylic acid. Disodium cocoampho dipropionate is one most preferred amphoteric surfactant and is commercially available under the tradename Miranol™ FBS from Rhodia Inc., Cranbury, N.J. Another most preferred coconut derived amphoteric surfactant with the chemical name disodium cocoampho diacetate is sold under the tradename Miranol C2M-SF Conc., also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Additional surfactant may be present in the compositions in any detersive amount so long as they do not interfere with the electrostatic, ionic interactions that provide for foam stabilization.

Enzymes

The composition of the invention may include one or more enzymes, which can provide desirable activity for removal of protein-based, carbohydrate-based, or triglyceride-based stains from substrates; for cleaning, destaining, and sanitizing presoaks, such as presoaks for flatware, cups and bowls, and pots and pans; presoaks for medical and dental instruments; or presoaks for meat cutting equipment; for machine warewashing; for laundry and textile cleaning and destaining; for carpet cleaning and destaining; for cleaning-in-place and destaining-in-place; for cleaning and destaining food processing surfaces and equipment; for drain cleaning; presoaks for cleaning; and the like. Enzymes may act by degrading or altering one or more types of soil residues encountered on a surface or textile thus removing the soil or making the soil more removable by a surfactant or other component of the cleaning composition. Both degradation and alteration of soil residues can improve detergency by reducing the physicochemical forces which bind the soil to the surface or textile being cleaned, i.e. the soil becomes more water soluble. For example, one or more proteases can cleave complex, macromolecular protein structures present in soil residues into simpler short chain molecules which are, of themselves, more readily desorbed from surfaces, solubilized or otherwise more easily removed by detersive solutions containing said proteases.

Suitable enzymes may include a protease, an amylase, a lipase, a gluconase, a cellulase, a peroxidase, or a mixture thereof of any suitable origin, such as vegetable, animal, bacterial, fungal or yeast origin. Selections are influenced by factors such as pH-activity and/or stability optima, thermostability, and stability to active detergents, builders and the like. In this respect bacterial or fungal enzymes may be preferred, such as bacterial amylases and proteases, and fungal cellulases. Preferably the enzyme may be a protease, a lipase, an amylase, or a combination thereof. Enzyme may be present in the composition from at least 0.01 wt. %, or 0.01 to 2 wt. %.

Enzyme Stabilizing System

The composition of the invention may include an enzyme stabilizing system. The enzyme stabilizing system can include a boric acid salt, such as an alkali metal borate or amine (e.g. an alkanolamine)borate, or an alkali metal borate, or potassium borate. The enzyme stabilizing system can also include other ingredients to stabilize certain enzymes or to enhance or maintain the effect of the boric acid salt.

For example, the cleaning composition of the invention can include a water soluble source of calcium and/or magnesium ions. Calcium ions are generally more effective than magnesium ions and are preferred herein if only one type of cation is being used. Cleaning and/or stabilized enzyme cleaning compositions, especially liquids, may include 1 to 30, 2 to 20, or 8 to 12 millimoles of calcium ion per liter of finished composition, though variation is possible depending on factors including the multiplicity, type and levels of enzymes incorporated. Water-soluble calcium or magnesium salts may be employed, including for example calcium chloride, calcium hydroxide, calcium formate, calcium malate, calcium maleate, calcium hydroxide and calcium acetate; more generally, calcium sulfate or magnesium salts corresponding to the listed calcium salts may be used. Further increased levels of calcium and/or magnesium may of course be useful, for example for promoting the grease-cutting action of certain types of surfactant.

Stabilizing systems of certain cleaning compositions, for example warewashing stabilized enzyme cleaning compositions, may further include 0 to 10%, or 0.01% to 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme, for example during warewashing, can be relatively large; accordingly, enzyme stability to chlorine in-use can be problematic.

Suitable chlorine scavenger anions are known and readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used.

Chelating/Sequestering Agent

The composition may include a chelating/sequestering agent such as an aminocarboxylic acid, a condensed phosphate, a phosphonate, a polyacrylate, and the like. In general, a chelating agent is a molecule capable of coordinating (i.e., binding) the metal ions commonly found in natural water to prevent the metal ions from interfering with the action of the other detersive ingredients of a cleaning composition. The chelating/sequestering agent may also function as a threshold agent when included in an effective amount. The composition may include 0.1-70 wt. %, or 5-60 wt. %, of a chelating/sequestering agent. An iminodisuccinate (available commercially from Bayer as IDS™) may be used as a chelating agent.

Useful aminocarboxylic acids include, for example, N-hydroxyethyliminodiacetic acid, nitrilotriacetic acid (NTA), ethylenediaminetetraacetic acid (EDTA), N-hydroxyethyl-ethylenediaminetriacetic acid (HEDTA), diethylenetriaminepentaacetic acid (DTPA), and the like.

Examples of condensed phosphates useful in the present composition include sodium and potassium orthophosphate, sodium and potassium pyrophosphate, sodium tripolyphosphate, sodium hexametaphosphate, and the like.

The composition may include a phosphonate such as 1-hydroxyethane-1,1-diphosphonic acid and the like.

Polymeric polycarboxylates may also be included in the composition. Those suitable for use as cleaning agents have pendant carboxylate groups and include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like. For a further discussion of chelating agents/sequestrants, see Kirk-Othmer, Encyclopedia of Chemical Technology, Third Edition, volume 5, pages 339-366 and volume 23, pages 319-320, the disclosure of which is incorporated by reference herein.

Bleaching Agents

Bleaching agents for lightening or whitening a substrate, include bleaching compounds capable of liberating an active halogen species, such as $C_{12}$, $Br_2$, —$OCl^-$ and/or —$OBr^-$, under conditions typically encountered during the cleansing process. Suitable bleaching agents include, for example, chlorine-containing compounds such as a chlorine, a hypochlorite, chloramine. Halogen-releasing compounds may include the alkali metal dichloroisocyanurates, chlorinated trisodium phosphate, the alkali metal hypochlorites, monochloramine and dichloramine, and the like. Encapsulated chlorine sources may also be used to enhance the stability of the chlorine source in the composition (see, for example, U.S. Pat. Nos. 4,618,914 and 4,830,773, the disclosure of which is incorporated by reference herein). A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. A cleaning composition may include a minor but effective amount of a bleaching agent, such as 0.1-10 wt. %, or 1-6 wt. %.

Detergent Builders or Fillers

A composition may include a minor but effective amount of one or more of a detergent filler which does not perform as a cleaning agent per se, but cooperates with the cleaning agent to enhance the overall cleaning capacity of the composition. Examples of fillers suitable for use in the present cleaning compositions include sodium sulfate, sodium chloride, starch, sugars, $C_1$-$C_{10}$ alkylene glycols such as propylene glycol, and the like. Inorganic or phosphate-containing detergent builders may include alkali metal, ammonium and alkanolammonium salts of polyphosphates (e.g. tripolyphosphates, pyrophosphates, and glassy polymeric meta-phosphates). Non-phosphate builders may also be used. A detergent filler may be included in an amount of 1-20 wt. %, or 3-15 wt. %.

Anti-Redeposition Agents

The composition may include an anti-redeposition agent capable of facilitating sustained suspension of soils in a cleaning solution and preventing the removed soils from being redeposited onto the substrate being cleaned. Examples of suitable anti-redeposition agents include fatty acid amides, fluorocarbon surfactants, complex phosphate esters, styrene maleic anhydride copolymers, and cellulosic derivatives such as hydroxyethyl cellulose, hydroxypropyl cellulose, and the like. The composition may include 0.5-10 wt. %, or 1-5 wt. %, of an anti-redeposition agent.

Dyes/Odorants

Various dyes, odorants including perfumes, and other aesthetic enhancing agents may also be included in the composition. Dyes may be included to alter the appearance of the composition, as for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like.

Fragrances or perfumes that may be included in the compositions include, for example, terpenoids such as citronellol, aldehydes such as amyl cinnamaldehyde, a jasmine such as CIS-jasmine or jasmal, vanillin, and the like.

Divalent Ion

The compositions of the invention may contain a divalent ion, selected from calcium and magnesium ions, at a level of from 0.05% to 5% by weight, or from 0.1% to 1% by weight, or 0.25% by weight of the composition. The divalent ion can be, for example, calcium or magnesium. The calcium ions can, for example, be added as a chloride, hydroxide, oxide, formate, acetate, nitrate salt.

Polyol

The composition of the invention can also include a polyol. The polyol may provide additional stability and hydrotrophic properties to the composition. Propylene glycol and sorbitol are examples of some suitable polyols.

Thickening Agent

In some embodiments, it is contemplated that a thickening agent may be included, however, in many embodiments, it is not required. Some examples of additional thickeners include soluble organic or inorganic thickener material. Some examples of inorganic thickeners include clays, silicates and other well-known inorganic thickeners. Some examples of organic thickeners include thixotropic and non-thixotropic thickeners. In some embodiments, the thickeners have some substantial proportion of water solubility to promote easy removability. Examples of useful soluble organic thickeners for the compositions of the invention comprise carboxylated vinyl polymers such as polyacrylic acids and sodium salts thereof, ethoxylated cellulose, polyacrylamide thickeners, xanthan thickeners, guargum, sodium alginate and algin by-products, hydroxy propyl cellulose, hydroxy ethyl cellulose and other similar aqueous thickeners that have some substantial proportion of water solubility.

Hardening Agent

A hardening agent, as used in the present method and compositions, is a compound or system of compounds, organic or inorganic, that significantly contributes to the uniform solidification of the composition. Preferably, the hardening agents are compatible with the cleaning agent and other active ingredients of the composition, and are capable of providing an effective amount of hardness and/or aqueous solubility to the processed composition. The hardening agents should also be capable of forming a homogeneous matrix with the cleaning agent and other ingredients when mixed and solidified to provide a uniform dissolution of the cleaning agent from the solid composition during use.

The amount of hardening agent included in the cleaning composition will vary according to the type of cleaning composition being prepared, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. It is preferred that the amount of the hardening agent is effective to combine with the cleaning agent and other ingredients of the composition to form a homogeneous mixture under continuous mixing conditions and a temperature at or below the melting temperature of the hardening agent.

It is also preferred that the hardening agent form a matrix with the cleaning agent and other ingredients which will harden to a solid form under ambient temperatures of about 30 to 50° C., preferably about 35 to 45° C., after mixing ceases and the mixture is dispensed from the mixing system, within about 1 minute to about 3 hours, preferably about 2 minutes to about 2 hours, preferably about 5 minutes to about 1 hour. A minimal amount of heat from an external source may be applied to the mixture to facilitate processing of the mixture. It is preferred that the amount of the hardening agent included in the composition is effective to provide a hardness and desired rate of controlled solubility of the processed composition when placed in an aqueous medium to achieve a desired rate of dispensing the cleaning agent from the solidified composition during use.

The preferred organic hardening agent is a polyethylene glycol (PEG) compound for use in the above cleaning composition. The solidification rate of cleaning compositions comprising a polyethylene glycol hardening agent made according to the invention will vary, at least in part, according to the amount and the molecular weight of the polyethylene glycol added to the composition.

Polyethylene glycol compounds useful according to the invention include, for example, solid polyethylene glycols of the general formula $H(OCH_2-CH_2)_nOH$, where n is greater than 15, more preferably about 30 to 1700. Solid polyethylene glycols which are useful are commercially available from Union Carbide under the name CARBOWAX. Typically, the polyethylene glycol is a solid in the form of a free-flowing powder or flakes, having a molecular weight of about 1000 to 100,000, preferably having a molecular weight of at least about 1450 to 20,000, more preferably between about 1450 to about 8000. The polyethylene glycol is present at a concentration of from about 1 to 75 wt.-%, preferably about 3 to 15 wt.-%. Suitable polyethylene glycol compounds useful according to the invention include, for example, PEG 1450 and PEG 8000 among others, with PEG 8000 being most preferred.

Preferred inorganic hardening agents are hydratable inorganic salts, such as sulfates, acetates, carbonates, and bicarbonates. The inorganic hardening agents are present at concentrations of about 0 to 50 wt.-%, preferably about 5-25 wt.-%, more preferably about 5-15 wt-%.

Alkaline Sources

The cleaning composition produced according to the invention may include minor but effective amounts of one or more alkaline sources to neutralize the anionic surfactants and improve soil removal performance of the composition. Accordingly, an alkali metal or alkaline earth metal hydroxide or other hydratable alkaline source, is preferably included in the cleaning composition in an amount effective to neutralize the anionic surfactant. However, it can be appreciated that an alkali metal hydroxide or other alkaline source can assist to a limited extent, in solidification of the composition. Although the amount of alkali metal and alkaline earth metal hydroxide is necessitated to neutralize the anionic surfactant as above described, additional alkaline sources may be present to a point where the pH of an aqueous solution does not exceed 9.

Suitable alkali metal hydroxides include, for example, sodium or potassium hydroxide. Suitable alkaline earth metal hydroxides include, for example, magnesium hydroxide. An alkali or alkaline earth metal hydroxide may be added to the composition in the form of solid beads, dissolved in an aqueous solution, or a combination thereof. Alkali and alkaline earth metal hydroxides are commercially available as a solid in the form of prilled beads having a mix of particle sizes ranging from about 12-100 U.S. mesh, or as an aqueous solution, as for example, as a 50 wt.-% and a 73 wt.-% solution. It is preferred that the alkali or alkaline earth metal hydroxide is added in the form of an aqueous solution, preferably a 50 wt.-% hydroxide solution, to reduce the amount of heat generated in the composition due to hydration of the solid alkali material.

A cleaning composition may include a secondary alkaline source other than an alkali metal hydroxide. Examples of secondary alkaline sources include a metal silicate such as sodium or potassium silicate or metasilicate, a metal carbonate such as sodium or potassium carbonate, bicarbonate or sesquicarbonate, and the like; a metal borate such as sodium or potassium borate, and the like; ethanolamines and amines; and other like alkaline sources. Secondary alkalinity agents are commonly available in either aqueous or powdered form, either of which is useful in formulating the present cleaning compositions.

Chelating/Sequestering Agents

The composition may include a chelating/sequestering agent such as an aminocarboxylic acid, a condensed phosphate, a phosphonate, a polyacry-late, and the like. In general, a chelating agent is a molecule capable of coordinating (i.e., binding) the metal ions commonly found in natural water to prevent the metal ions from interfering with the action of the other detersive ingredients of a cleaning composition. Depending on the type of cleaning composition being formulated, a chelating/sequestering agent is included in an amount of about 0.1 to 70 wt.-%, preferably from about 5 to 50 wt.-%.

Useful aminocarboxylic acids include, for example, n-hydroxyethyliminodiacetic acid, nitrilotriacetic acid (NTA), ethylenediaminetetraacetic acid (EDTA), N-hydroxyethyl-ethylenediaminetriacetic acid (HEDTA), diethylenetriaminepentaacetic acid (DTPA), and the like. Examples of condensed phosphates useful in the present composition include, for example, sodium and potassium orthophosphate, sodium and potassium pyrophosphate, sodium tripolyphosphate, sodium hexametaphosphate, and the like. A condensed phosphate may also assist, to a limited extent, in solidification of the composition by fixing the free water present in the composition as water of hydration.

The composition may include a phosphonate such as aminotris(methylene phosphonic acid), hydroxyethylidene diphosphonic acid, ethylenediaminetetra(methylene phosphonic acid), diethylenetriaminepente(methylene phosphonic acid), and the like. It is preferred to use a neutralized or alkaline phosphonate, or to combine the phosphonate with an alkali source prior to being added into the mixture such that there is little or no heat generated by a neutralization reaction when the phosphate is added.

Polyacrylates suitable for use as cleaning agents include, for example, polyacrylic acid, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like. For a further discussion of chelating agents/sequestrants, see Kirk-Othmer, Encyclopedia of Chemical Technology, Third Edition, volume 5, pages 339-366 and volume 23, pages 319-320, the disclosure of which is incorporated by reference herein.

Methods of Making the Compositions

The compositions according to the invention are easily produced by any of a number of known art techniques. Conveniently, a part of the water is supplied to a suitable mixing vessel further provided with a stirrer or agitator, and while stirring, the remaining constituents are added to the mixing vessel, including any final amount of water needed to provide to 100% wt. of the inventive composition.

The compositions may be packaged in any suitable container particularly flasks or bottles, including squeeze-type bottles, as well as bottles provided with a spray apparatus (e.g. trigger spray) which is used to dispense the composition by spraying. Accordingly the compositions are desirably provided as a ready to use product in a manually operated spray dispensing container, or may be supplied in aerosolized product wherein it is discharged from a pressurized aerosol container. Propellants which may be used are well known and conventional in the art and include, for example, a hydrocarbon, of from 1 to 10 carbon atoms, such as n-propane, n-butane, isobutane, n-pentane, isopentane, and mixtures thereof; dimethyl ether and blends thereof as well as individual or mixtures of chloro-, chlorofluoro- and/or fluorohydrocarbons- and/or hydrochlorofluorocarbons (HCFCs). Useful commercially available compositions include A-70 (Aerosol compositions with a vapor pressure of 70 psig available from companies such as Diversified and Aeropress) and Dyme® 152a (1,1-difluoroethane from DuPont). Compressed gases such as carbon dioxide, compressed air, nitrogen, and possibly dense or supercritical fluids may also be used. In such an application, the composition is dispensed by activating the release nozzle of said aerosol type container onto the area in need of treatment, and in accordance with a manner as above-described the area is treated (e.g., cleaned and/or sanitized and/or disinfected). If a propellant is used, it will generally be in an amount of from about 1% to about 50% of the aerosol formulation with preferred amounts being from about 2% to about 25%, more preferably from about 5% to about 15%. Generally speaking, the amount of a particular propellant employed should provide an internal pressure of from about 20 to about 150 psig at 70° F.

Preferably, the composition is adapted for being dispensed using a trigger spray. Alternately, preferably, the composition is adapted for being dispensed using a squeeze bottle through a nozzle.

The compositions according to the invention can also be suited for use in a consumer "spray and wipe" application as a cleaning composition. In such an application, the consumer generally applies an effective amount of the composition using the pump and within a few moments thereafter, wipes off the treated area with a cloth, towel, or sponge, usually a disposable paper towel or sponge. In certain applications, however, especially where undesirable stain deposits are heavy, such as grease stains the cleaning composition according to the invention may be left on the stained area until it has effectively loosened the stain deposits after which it may then be wiped off, rinsed off, or otherwise removed. For particularly heavy deposits of such undesired stains, multiple applications may also be used. Optionally, after the composition has remained on the surface for a period of time, it could be rinsed or wiped from the surface. Due to the viscoelasticity of the compositions, the cleaning compositions have improved cling and remain for extended periods of time even on vertical surfaces.

Whereas the compositions of the present invention are intended to be used in the types of liquid forms described, nothing in this specification shall be understood as to limit the use of the composition according to the invention with a further amount of water to form a cleaning solution there from. In such a proposed diluted cleaning solution, the greater the proportion of water added to form said cleaning dilution will, the greater may be the reduction of the rate and/or efficacy of the thus formed cleaning solution. Accordingly, longer residence times upon the stain to affect their loosening and/or the usage of greater amounts may be necessitated. Preferred dilution ratios of the concentrated hard surface cleaning composition:water of 1:1-100, preferably 1:2-100, more preferably 1:3-100, yet more preferably 1:10-100, and most preferably 1:16-85, on either a weight/weight ("w/w") ratio or alternately on a volume/volume ("v/v") ratio. Conversely, nothing in the specification shall be also understood to limit the forming of a "super-concentrated" cleaning composition based upon the composition described above. Such a super-concentrated ingredient composition is essentially the same as the cleaning compositions described above except in that they include a lesser amount of water.

In other embodiments, the invention provides a laundry detergent pre-treatment composition comprising one or more of the above-described cleaning compositions of the invention and one or more additional detergent components. In certain such embodiments, the laundry detergent composition is provided as a liquid composition, spray, aerosol or as a foaming gel composition.

In other embodiments, the invention provides a hard surface cleaning composition comprising one or more of the above-described cleaning compositions of the invention and one or more additional cleaning components. In certain such embodiments, the hard surface cleaning composition is provided as a liquid composition, spray, aerosol or as a foaming gel composition.

In other embodiments, the invention provides a dishware cleaning composition comprising one or more of the above-described cleaning compositions of the invention and one or more additional dishware cleaning components (such as one or more enzymes, one or more rinse aids, one or more surfactants, one or more builders, one or more bleaches or bleach-generating compounds or systems, and the like. In certain such embodiments, the dishware cleaning composition is provided as a liquid composition, spray, aerosol or as a foaming gel composition. In additional such embodiments, the dishware cleaning composition is provided in unit dose format, such as in a water-dissolvable (e.g., polyvinyl alcohol) pouch, tablet, or the like, suitable for use in automatic dishwashing machines.

In additional embodiments, the invention provides a method for laundering fabrics comprising agitating fabrics in an aqueous solution containing from about 0.01% to about 5% by weight of one or more of the compositions (for example, one or more of the laundry detergent compositions) of the present invention.

In additional embodiments, the invention provides a method for cleaning hard surfaces comprising contacting the hard surface with an aqueous solution containing from about 0.01% to about 5% by weight of one or more of the compositions (for example, one or more of the hard surface cleaning compositions) of the present invention.

In additional embodiments, the invention provides methods for cleaning dishware, comprising contacting the dishware with an aqueous solution containing from about 0.01% to about 5% by weight of one or more of the compositions (for example, one or more of the dishware cleaning compositions) of the present invention.

Methods of Cleaning

The present invention also relates to methods of cleaning a soiled object. This embodiment of the method can include contacting the object with a cleaning composition of the invention. The cleaning steps can be provided in a number of ways depending on the specific formulation. In an embodiment, the method can include contacting the object with cleaning composition according to the in any of a number of for a predetermined time, preferably for a sufficient amount of time to allow the foam dissipate; and after passage of the predetermined time, rising the cleaning composition from the object so that the cleaning composition and any soils or debris are washed away. The method can be employed to clean any of a variety of objects. In an embodiment, the soiled object includes or is pipes or vessels in a food processing plant, wares, laundry, an oven, a grill, or a floor, a carpet, a medical device.

Exemplary Compositions

The table below gives useful, preferred and more preferred composition ranges for each essential ingredient in the invention with any remainder being water:

| | preferred | more preferred | most preferred |
|---|---|---|---|
| PEI | .01-5 | 0.5-3.5 | 0.1-2 |
| Anionic surfactant | 1-75 | 5-65 | 15-60 |
| Amphoteric surfactant, amine oxide | 0-7.99, active. | 1-7, active | 2-6, active |
| If no amine oxide, amphoteric surfactant, betaine or sultaine | .01-75 | 10-30 | 15-25 |

The present invention will now be further illustrated by way of the following non-limiting examples, in which parts and percentages are by weight unless otherwise indicated.

EXAMPLES

Manual Pot and Pan Cylinder Foam Test Method

Purpose:
 To screen hand dish washing detergents for foam height and stability.
Scope:
 This procedure applies to any hand dish washing product.
Apparatus and Materials:
1. Cisco Shortening
2. Flour
3. Powdered Egg
4. Oleic acid
5. Disposable pipets
6. Guwina-Hoffmann rotation device
7. Ground glass stoppered graduated cylinders (250 ml)
8. Rubber stoppers
9. Hop plate with variable heat adjustment
10. Water bath/heat chamber
Soil Formula:
1. 45% Crisco Shortening
2. 30% Flour
3. 15% Powdered Egg
4. 10% Oleic Equipment Setup:
 Calibrate the Guwina-Hofmann rotation devise to 30 rpm.
Procedure:
1. Prepare solutions. Test solution is 500 ppm active surfactant (not to include SXS).
2. To a 250 ml graduated cylinder, add 40 mls of test solution. Repeat this step for each product. Label all cylinders.
3. Loosen stoppers and heat cylinders containing solutions to 80° F. and a second set to 110° F.
4. Liquefy soil on a low temperature hot plate set at 104° F.
5. Stopper cylinders, place in apparatus, and secure tightly.
6. Rotate for 240 sec (4 minutes). Record initial foam height. Add 2 drops (0.5 g) soil with disposable pipettes.
7. Rotate for 120 sec (2 minutes). Record foam height. Add 2 drops (0.5 g) soil with disposable pipette. Continue this process until 40 mls or less foam height remain.

Calculations:
 Sum of all foam heights—(# of readings)*40 mls
General Comments:
 Make sure that the graduated cylinders are secure before starting the rotations.

The compositions prepared and studied are shown on the table below. The raw material labeled as ES 8965, PEI ethoxylate is identical to Sokalan HP-20. The raw material labeled as Acusol 820 is an effective associative thickener found to be very effective from ROI 2865US01.

| POT AND PAN DEA REPLACEMENT | % active | Commercial Product 1 | Commercial Product 2 | Commercial Product 3 | DEA replacement #1 | DEA replacement #2 | DEA replacement #3 | DEA replacement #4 | DEA replacement #5 | DEA replacement #6 2% Acusol 820 | DEA replacement #7 | DEA replacement #8 | DEA replacement #9 (#24 & #28) 1% Acusol 820 only | DEA replacement #10 1% Acusol 820 + 1.5% salt |
|---|---|---|---|---|---|---|---|---|---|---|---|---|---|---|
| Water Zeolite Softened TNK | | 0.00 | 0.00 | 31.78 | 47.18 | 46.50 | 45.50 | 44.50 | 43.50 | 42.26 | 43.68 | 48.68 | 53.93 | 52.75 |
| Acusol 820 | | | | 0.00 | 2.00 | 2.00 | 2.00 | 2.00 | 2.00 | 2.00 | 2.00 | 2.00 | 1.00 | 1.00 |
| Glutamate LT | | | | | | | | | | 1.50 | | | | |
| Laponite | 1 | | | | | | | | | | | | | |
| Sodium Chloride; FCC Gran | | | | 1.50 | 1.50 | 1.50 | 1.50 | 1.50 | 1.50 | 1.50 | | | | 1.50 |
| Mg Sulfate heptahydrate | | | | | | | | | | | | | | |
| ES 8965, PEI ethoxylate | | | | | | | | | | | | | | |
| Sokalan HP-70 | | | | | | | | | | | | | | |
| Propylene Glycol Technical DRM | | | | 1.50 | 1.50 | 1.50 | 1.50 | 1.50 | 1.50 | 1.50 | 1.50 | 1.50 | | |
| Ethanol, SDA-3C | | | | 1.75 | 1.75 | 1.75 | 1.75 | 1.75 | 1.75 | 1.75 | 1.75 | 1.75 | | |
| DEA COCO AMIDE (1/1) IBC | 0.96 | | | 12.22 | | | | | | | | | | |
| Sodium Lauryl Ether Ethoxylate Sulfate 60% | 0.6 | | | 12.00 | 12.00 | 12.00 | 12.00 | 12.00 | 12.00 | 12.00 | 12.00 | 12.00 | 12.00 | 12.00 |
| Sodium C14-16 Olefin Sulfonate TNK | 0.4 | | | 29.75 | 29.75 | 29.75 | 29.75 | 29.75 | 29.75 | 29.75 | 29.75 | 29.75 | 29.75 | 29.75 |
| CITRIC ACID, 50% TAN | | | | 0.50 | | | | | | | | | | |
| LAURAMINE OXIDE 29-31% IBC | 0.3 | | | 3.00 | 3.00 | 3.00 | 3.00 | 3.00 | 3.00 | 3.00 | 3.00 | 3.00 | 3.00 | 3.00 |
| Sodium Xylene Sulfonate 40% TNK | 0.4 | | | 6.00 | 1.00 | 2.00 | 3.00 | 4.00 | 5.00 | 6.00 | 6.00 | 1.00 | | |
| Total | | 0.00 | 0.00 | 100.00 | 100.00 | 100.00 | 100.00 | 100.00 | 100.00 | 100.00 | 100.00 | 100.00 | 100.00 | 100.00 |
| % Active Surfactant | | 34.00 | 29.9 | 31.73 | 20.00 | 20.00 | 20.00 | 20.00 | 20.00 | 20.00 | 20.00 | 20.00 | 20.00 | 20.00 |
| % Active Amine Oxide | | 1.68 | 13.71 | 0.9 | 0.9 | 0.9 | 0.9 | 0.9 | 0.9 | 0.9 | 0.9 | 0.9 | 0.9 | 0.9 |

-continued

| POT AND PAN DEA REPLACEMENT | % active | Commercial Product 1 | Commercial Product 2 | Commercial Product 3 | DEA replacement #11 1% Acusol 820 + 6% SXS | DEA replacement #12 1% Acusol 820 + 1.5% P glycol | DEA replacement #13 1% Acusol 820 + 1.75% Ethanol | DEA replacement #14 (#30) .5% ES 8965 only | DEA replacement #15 .5% Sokalan HP 70 | DEA replacement #16 914316 | DEA replacement #17 914316 | DEA replacement #18 | DEA replacement #19 | DEA replacement #20 .43% ES 8965 + 5.8% AO |
|---|---|---|---|---|---|---|---|---|---|---|---|---|---|---|
| 100016 Water Zeolite Softened TNK | | | | 31.78 | 48.25 | 52.75 | 52.50 | 54.75 | 54.75 | 43.03 | 53.75 | 43.98 | 52.25 | 44.47 |
| 230268 Acusol 820 | | | | 0.00 | 1.00 | 1.00 | 1.00 | | | 0.00 | 1.00 | 11.27 | 3.00 | |
| Glutamate LT Laponite | | | | 1.50 | | | | | | | 0.50 | | | |
| 830242 Sodium Chloride; FCC Gran | | | | | | | | | | | | | | |
| 143040 Mg Sulfate heptahydrate | | | | | | | | | | | | | | |
| ES 8965, PEI ethoxylate | 1 | | | | | | | | | | | | | 0.43 |
| 164079 Sokalan HP-70 | | | | | | 1.50 | | | 0.50 | | | | | |
| Propylene Glycol Technical DRM | | | | 1.50 | | | 1.75 | | | | | | | |
| 830699 Ethanol, SDA-3C | | | | 1.75 | | | | | | | | | | |
| 173856 DEA COCO AMIDE (1/1) IBC | 0.96 | | | 12.22 | | | | | | 12.22 | | | | |
| 171405 Sodium Lauryl Ether Ethoxylate Sulfate 60% | 0.6 | | | 12.00 | 12.00 | 12.00 | 12.00 | 12.00 | 12.00 | 12.00 | 12.00 | 12.00 | 12.00 | 10.21 |
| 171318 Sodium C14-16 Olefin Sulfonate TNK | 0.4 | | | 29.75 | 29.75 | 29.75 | 29.75 | 29.75 | 29.75 | 29.75 | 29.75 | 29.75 | 29.75 | 25.32 |
| 830774 CITRIC ACID, 50% TAN | | | | 0.50 | | | | | | | | | | |
| 172452 LAURAMINE OXIDE 29-31% IBC | 0.3 | | | 3.00 | 3.00 | 3.00 | 3.00 | 3.00 | 3.00 | 3.00 | 3.00 | 3.00 | 3.00 | 19.57 |
| 171371 Sodium Xylene Sulfonate 40% TNK | 0.4 | | | 6.00 | 6.00 | | | | | | | | | |
| Total | | 0.00 | 0.00 | 100.00 | 100.00 | 100.00 | 100.00 | 100.00 | 100.00 | 100.00 | 100.00 | 100.00 | 100.00 | 100.00 |
| % Active Surfactant | | 34.00 | 29.9 | 31.73 | 20.00 | 20.00 | 20.00 | 20.50 | 20.00 | 31.73 | 20.00 | 20.00 | 20.00 | 22.55 |
| % Active Amine Oxide | | 1.68 | 13.71 | 0.9 | 0.9 | 0.9 | 0.9 | 0.9 | 0.9 | 0.9 | 0.9 | 0.9 | 0.9 | 5.87 |

-continued

| POT AND PAN DEA REPLACEMENT | | % active | Com-mercial Product 1 | Com-mercial Product 2 | Com-mercial Product 3 | DEA replace-ment #32 1% Acusol 820, 0% SLES | DEA replacement #33 | DEA replacement #34 Acusol 820 + 0.50% ES 8965 + 0.9% AO | DEA replacement #14-3 ##14-3 .5% ES 8965 only | DEA replacement #29-3 .43% ES 8965 + 5.8% AO | DEA replacement #29-4 .5% ES 8965 + 6.9% AO | DEA replacement #29-5 .43% ES 8965 + 5.8% AO | DEA replacement #20-2 .43% ES 8965 + 5.8% AO | DEA replacement #29-6 .5% ES 8965 + 6.9% AO | DEA replacement #20-3 .43% ES 8965 + 5.8% AO |
|---|---|---|---|---|---|---|---|---|---|---|---|---|---|---|---|
| 100016 | Water Zeolite Softened TNK | | 0.00 | 0.00 | 31.78 | 46.25 | 35.25 | 53.75 | 53.21 | 33.57 | 34.75 | 33.57 | 44.47 | 34.75 | 44.47 |
| 230268 | Acusol 820 | | | | 0.00 | 1.00 | | 1.00 | | | | | | | |
| | Glutamate LT Laponite | | | | | | | | | | | | | | |
| 830242 | Sodium Chloride; FCC Gran | | | | 1.50 | | | | | | | | | | |
| 143040 | Mg Sulfate heptahydrate | | | | | | | | | | | | | | |
| | ES 8965, PEI ethoxylate | 1 | | | | | | 0.50 | 0.50 | 0.50 | 0.50 | 0.50 | 0.43 | 0.50 | 0.43 |
| 164079 | Sokalan HP-70 | | | | 1.50 | | | | | | | | | | |
| | Propylene Glycol Technical DRM | | | | | | | | | | | | | | |
| 830699 | Ethanol, SDA-3C | | | | 1.75 | | | | | | | | | | |
| 173856 | DEA COCO AMIDE (1/1) IBC | 0.96 | | | 12.22 | | | | | | | | | | |
| 171405 | Sodium Lauryl Ether Ethoxylate Sulfate 60% | 0.6 | | | 12.00 | 12.00 | 12.00 | 12.00 | 12.00 | 12.00 | 12.00 | 12.00 | 10.21 | 12.00 | 10.21 |
| 171318 | Sodium C14-16 Olefin Sulfonate TNK | 0.4 | | | 29.75 | 29.75 | 29.75 | 29.75 | 29.75 | 29.75 | 29.75 | 29.75 | 25.32 | 29.75 | 25.32 |
| 830774 | CITRIC ACID, 50% TAN | | | | 0.50 | | | 0.50 | 0.66 | | | | 0.79 | | |
| 172452 | LAURAMINE OXIDE 29-31% IBC | 0.3 | | | 3.00 | 23.00 | 23.00 | 3.00 | 3.00 | 23.00 | 23.00 | 23.00 | 19.57 | 23.00 | 19.57 |
| 171371 | Sodium Xylene Sulfonate 40% TNK | 0.4 | | | 6.00 | | | | | | | | | | |
| | Total | | 0.00 | 0.00 | 100.00 | 100.00 | 100.00 | 100.50 | 99.12 | 98.82 | 100.00 | 98.82 | 100.79 | 100.00 | 100.00 |
| | % Active Surfactant | | 34.00 | 29.9 | 31.73 | 18.80 | 26.00 | 20.50 | 20.50 | 26.50 | 26.50 | 26.50 | 22.55 | 26.50 | 22.55 |
| | % Active Amine Oxide | | 1.68 | 13.71 | 0.9 | 6.9 | 6.9 | 0.9 | 0.9 | 6.9 | 6.9 | 6.9 | 5.87234043 | 6.9 | 5.872340426 |

| | POT AND PAN DEA REPLACEMENT | | % active | Commercial Product 1 | Commercial Product 2 | Commercial Product 3 | DEA replacement #35 .5% ES 8965 + 6.9% AO | DEA replacement #36 1% ES 8965 + 6.9% AO | DEA replacement #37 2% ES 8965 + 6.9% AO | DEA replacement #38 | DEA replacement #39 |
|---|---|---|---|---|---|---|---|---|---|---|---|
| 100016 | Water Zeolite Softened TNK | | | | | 31.78 | 34.75 | 34.25 | 33.25 | 53.75 | 33.75 |
| 230268 | Acusol 820 | | 0.5 | | | 0.00 | | | | | |
| | Glucamate LT | | | | | | | | | 1.00 | 1.00 |
| | Laponite | | | | | | | | | | |
| 830242 | Sodium Chloride; FCC Gran | | | | | 1.50 | | | | | |
| 143040 | Mg Sulfate heptahydrate | | | | | | | | | | |
| | ES 8965, PEI ethoxylate | | 1 | | | | 0.5 | 1 | 2 | 0.50 | 0.50 |
| | Sokalan HP-70 | | | | | | | | | | |
| 164079 | Propylene Glycol Technical DRM | | | | | 1.50 | | | | | |
| 830699 | Ethanol, SDA-3C | | | | | 1.75 | | | | | |
| 173856 | DEA COCO AMIDE (1/1) IBC | | 0.96 | | | 12.22 | | | | | |
| 830555 | Sodium Lauryl Ether Ethoxylate Sulfate 60% | | 0.6 | | | 12.00 | 12.00 | 12.00 | 12.00 | 12.00 | 12.00 |
| 171318 | Sodium C14-16 Olefin Sulfonate TNK | | 0.4 | | | 29.75 | 29.75 | 29.75 | 29.75 | 29.75 | 29.75 |
| 830774 | CITRIC ACID, 50% TAN | | | | | 0.50 | | | | | |
| 172452 | LAURAMINE OXIDE 29-31% IBC | | 0.3 | | | 3.00 | 23 | 23.00 | 23 | 3.00 | 23.00 |
| 171371 | Sodium Xylene Sulfonate 40% TNK | | | | | 6.00 | | | | | |
| | NaOH, 50% (for pH adjustment) | | | | | | | | | | |
| | Total | | | | | 100.00 | 100.00 | 100.00 | 100.00 | 100.00 | 100.00 |
| | % Active Surfactant | | | 34.00 | 29.9 | 31.73 | 26.50 | 27.00 | 28.00 | 21.00 | 27.00 |
| | % Active Amine Oxide | | | 1.68 | 13.71 | 0.90 | 6.90 | 6.90 | 6.90 | 0.90 | 6.90 |

| | POT AND PAN DEA REPLACEMENT | % active | Commercial Product 1 | Commercial Product 2 | Commercial Product 3 | DEA replacement #20 | DEA replacement #20-2 | DEA replacement #20-3 | DEA replacement #40 #20-AO Exp | DEA replacement #41 #20-AO Exp | DEA replacement #42 #20-AO Exp | DEA replacement #43 #20-AO Exp | DEA Replacement #29-7 |
|---|---|---|---|---|---|---|---|---|---|---|---|---|---|
| 100016 | Water Zeolite Softened TNK | | | | | 44.47 | 44.47 | 44.47 | 44.04 | 49.04 | 54.05 | 59.04 | 34.75 |
| | ES 8965, PEI ethoxylate | 1 | | | | 0.43 | 0.43 | 0.43 | 0.43 | 0.43 | 0.43 | 0.43 | 0.50 |
| 171405 | Sodium Lauryl Ether Ethoxylate Sulfate 60% | 0.6 | | | | 10.21 | 10.21 | 10.21 | 10.21 | 10.21 | 10.21 | 10.21 | 12.00 |
| 171318 | Sodium C14-16 Olefin Sulfonate TNK | 0.4 | | | | 25.32 | 25.32 | 25.32 | 25.32 | 25.32 | 25.32 | 25.32 | 29.75 |
| 172452 | LAURAMINE OXIDE 29-31% IBC | 0.3 | | | | 19.57 | 19.57 | 19.57 | 20.00 | 15.00 | 10.00 | 5.00 | 23.00 |
| | NaOH, 50% (for pH adjustment) | | | | | | | | | | | | |
| 830774 | CITRIC ACID, 50% TAN | | | | | | | | | | | | |
| | Total | | 34.00 | 29.9 | 31.73 | 100.00 | 100.00 | 100.00 | 100.00 | 100.00 | 100.01 | 100.00 | 100.00 |
| | % Active Surfactant | | | | | 22.55 | 22.55 | 22.55 | 22.68 | 21.18 | 19.68 | 18.18 | 26.50 |

| | POT AND PAN DEA REPLACEMENT | % active | Commercial Product 1 | Commercial Product 2 | Commercial Product 3 | DEA replacement #14 (#30) .5% ES 8965 only | DEA replacement #45 | DEA replacement #46 | DEA replacement #47 |
|---|---|---|---|---|---|---|---|---|---|
| % Active Amine Oxide | | | 1.68 | 13.71 | 0.90 | 5.87 | 5.87 | 5.87 | 5.87 | 6.00 | 4.50 | 3.00 | 1.50 | 6.90 |
| 100016 | Water Zeolite Softened TNK | | | | | 54.75 | 34.73 | 50.39 | 0.44 |
| | ES 8965, PEI ethoxylate | 1.00 | | | | 0.50 | 0.50 | 5.01 | 5.01 |
| 171405 | Sodium Lauryl Ether Ethoxylate Sulfate 60% | 0.60 | | | | 12.00 | 12.00 | 12.00 | 12.00 |
| 171318 | Sodium C14-16 Olefin Sulfonate TNK | 0.40 | | | | 29.75 | 29.75 | 29.75 | 29.75 |
| 172437 | LAURAMINE OXIDE 29-31% IBC | 0.30 | | | | 3.00 | 23.00 | 3.00 | 23.00 |
| Total | | | 100.00 | 100.00 | 31.73 | 100.00 | 99.98 | 100.14 | 100.18 |
| % Active Surfactant | | | 34.00 | 29.9 | 0.90 | 20.50 | 26.50 | 25.00 | 31.00 |
| % Active Amine Oxide | | | 1.68 | 13.71 | | 0.90 | 6.90 | 0.90 | 6.90 |

| POT AND PAN DEA REPLACEMENT | | % active | Commercial Product 1 | Commercial Product 2 | Commercial Product 3 | DEA replacement #48 increase actives | DEA replacement #49 increase actives | DEA Replacement #50 reduce gelling | DEA replacement #51 | DEA replacement #52 | DEA replacement #53 | DEA replacement #54 | DEA replacement #55 | DEA replacement #56 | DEA replacement #57 | DEA replacement #58 | DEA replacement #59 | DEA replacement #60 |
|---|---|---|---|---|---|---|---|---|---|---|---|---|---|---|---|---|---|---|
| 100016 | Water Zeolite Softened TNK | | | | | 29.16 | 22.34 | 22.34 | 24.50 | 29.50 | 37.50 | 44.50 | 36.50 | 41.50 | 32.50 | 29.50 | 46.50 | 31.50 |
| 230268 | Acusol 820 | 0.4 | | | | | | | | | | | | | | | | |
| | SL-42 | 1 | | | | | | | | | | | | | | | | |
| | ES 8965, PEI ethoxylate | 0.65 | | | | 0.50 | 0.50 | 5.00 | 20.00 | 22.50 | | | | | | 22.50 | | |
| 170274 | Lamesoft PO-65 | | | | | | | 0.50 | 0.50 | 0.50 | 0.50 | 0.50 | 0.50 | 0.50 | 0.50 | 0.50 | 0.50 | 0.50 |
| 164079 | Propylene Glycol Technical DRM | | | | | | | | | | 5.00 | 5.00 | | | | | | |
| 830699 | Ethanol, SDA-3C | | | | | | | | | | | | | | | | | 10.00 |
| 173856 | DEA COCO AMIDE (1/1) IBC | 0.96 | | | | 19.34 | 15.56 | 15.31 | 12.00 | 15.00 | 24.00 | 30.00 | 20.00 | 30.00 | 5.00 | 15.00 | 30.00 | |
| 171405 | Sodium Lauryl Ether Ethoxylate Sulfate 60% | 0.6 | | | | | | | | 12.00 | 10.00 | 5.00 | 20.00 | 5.00 | 39.00 | 12.00 | | |
| 171318 | Sodium C14-16 Olefin Sulfonate TNK | 0.4 | | | | 48.00 | 38.60 | 38.00 | 20.00 | | | | | | | | | 35.00 |

-continued

| Code | Component | %activity | Commercial Product 1 | Commercial Product 1 | Commercial Product 2 | Commercial Product 3 | DEA replacement #60 | DEA Replacement #48 | DEA replacement #61 | DEA replacement #62 | DEA Replacement #65 | DEA replacement #63 | DEA replacement #64 | DEA replacement #65 | DEA replacement #66 | DEA replacement #66 | DEA replacement #67 |
|---|---|---|---|---|---|---|---|---|---|---|---|---|---|---|---|---|---|
| 172437 | LAURAMINE OXIDE 29-31% IBC | 0.3 | | | | | | | | | | | | | | | |
| 171371 | SXS, 40% diamines | | | | | | | | | | | | | | | 5.00 | |
| 830774 | CITRIC ACID, 50% TAN / NaOH, 50% (for pH adjustment) | | | | | | 3.00 | | | | | | | | | | |
| | Total | | 34.00 | 29.9 | 31.73 | 31.73 | 100.00 | 100.00 | 100.00 | 102.50 | 100.00 | 108.00 | 100.00 | 100.00 | 107.50 | 100.00 | 100.00 |
| | % Active Surfactant | | 1.68 | 13.71 | 0.90 | 0.90 | 32.21 | 27.90 | 26.40 | 28.40 | 29.05 | 30.65 | 32.40 | 27.40 | 26.00 | 33.35 | 26.90 | 27.90 |
| | % Active Amine Oxide | | | | | | 6.9 | 6.9 | 6.9 | 6.9 | 6.9 | 6.9 | 6.9 | 6.9 | 6.9 | 6.9 | 6.9 |

| Code | POT AND PAN DEA REPLACEMENT | % activity | Commercial Product 1 | Commercial Product 2 | Commercial Product 3 | DEA replacement #60 | DEA replacement #61 | DEA Replacement #48 | DEA replacement #62 | DEA Replacement #65 | DEA replacement #63 | DEA replacement #64 | DEA replacement #65 | DEA replacement #66 | DEA replacement #67 |
|---|---|---|---|---|---|---|---|---|---|---|---|---|---|---|---|
| 100016 | Water Zeolite Softened TNK | | | | | | | | | | | | | | |
| 175075 | LAS | 0.96 | | | | 31.50 | 31.50 | 31.50 | 31.50 | 31.50 | 31.50 | 26.50 | 37.97 15.00 | 38.47 15.00 | 41.50 |
| 114132 | NaOH, 50% | 0.45 | | | | | | | | | | | 3.53 | 3.53 | |
| 177105 | Cocamidopropylbetaine SL-42 | 0.99 | | | | | 20.00 | | 10.00 | | | 5.00 | | | |
| 170274 | ES 8965, PEI ethoxylate | 1 | | | | 0.50 | 0.50 | | 0.50 | 0.50 | 0.50 | 0.50 | 0.50 | | 0.50 |
| 164079 | Lamesoft PO-65 | 0.65 | | | | 10.00 | | | 10.00 | | 20.00 | 15.00 | | | |
| 830699/164006 | Propylene Glycol Technical DRM Ethanol, SDA-3C | | | | | | | | | | | | | | |
| 173856 | DEA COCO AMIDE (1/1) IBC | 0.96 | | | | | | | | | | | | | |
| 171405 | Sodium Lauryl Ether Ethoxylate Sulfate 60% | 0.6 | | | | | | | | | | | | | |
| 171318 | Sodium C14-16 Olefin Sulfonate TNK | 0.4 | | | | 35.00 | | | | | 25.00 | 30.00 | 20.00 | 20.00 | 35.00 |
| 172437 | LAURAMINE OXIDE 29-31% IBC | 0.3 | | | | | | | | | | | | | |
| 171371 | Sodium Xylene Sulfonate 40% TNK | | | | | | | | | | | | | | |
| 830774 | CITRIC ACID, 50% TAN / NaOH, 50% (for pH adjustment) | | | | | 23.00 | 23.00 | | 23.00 | 23.00 | 23.00 | 23.00 | 23.00 | 23.00 | 23.00 |
| | Total | | 34.00 | 29.9 | 31.73 | 100.00 | 100.00 | 100.00 | 100.00 | 100.00 | 100.00 | 100.00 | 100.00 | 100.00 | 100.00 |
| | % Active Surfactant | | 1.68 | 13.71 | 0.90 | 27.90 | 26.40 | 31.50 | 28.40 | 37.97 | 30.40 | 34.10 | 33.80 | 33.30 | 28.40 |
| | % Active Amine Oxide | | | | | 6.9 | 6.9 | | 6.9 | | 6.9 | 6.9 | 6.9 | 6.9 | 6.9 |

| Code | POT AND PAN DEA REPLACEMENT | % activity | Commercial Product 1 | DEA replacement #66 | DEA Replacement #65 | DEA replacement #48 | DEA replacement #68 | DEA replacement #69 |
|---|---|---|---|---|---|---|---|---|
| 100016 | Water Zeolite Softened TNK | | | | | | | |
| 143040 | MgSO₄·7H₂O | | | 38.47 | 37.97 | 31.50 | 37.00 | 36.50 |
| 175075 | LAS | 0.96 | | 15.00 | 15.00 | | | |
| | KOH, 45% | | | | | | | |

-continued

| Code | Ingredient | | | | | | | | |
|---|---|---|---|---|---|---|---|---|---|
| 114132 | NaOH, 50% | 1 | | | | | 3.53 | 10.00 | 10.00 |
| | Novel II C12-14 21EO SL-42 | 0.99 | | | | | | | |
| 164079 | ES 8965, PEI ethoxylate Propylene Glycol Technical DRM | 1 | | | 0.50 | | | 0.50 | 0.50 |
| 830699/164006 173856 | Ethanol, SDA-3C DEA COCO AMIDE (1/1) IBC | 0.96 | | | | | | | |
| 171405 | Sodium Lauryl Ether Ethoxylate Sulfate 60% | 0.6 | | | 19.34 | | 20.00 | | |
| 171318 | Sodium C14-16 Olefin Sulfonate TNK | 0.4 | | | 48.00 | | | 30.00 | 30.00 |
| 172437 | LAURAMINE OXIDE 29-31% IBC | 0.3 | | | 3.00 | | 23.00 | 23.00 | 23.00 |
| 171371 | Sodium Xylene Sulfonate 40% TNK | | | | | | | | |
| 830242/142010 | Sodium Chloride; FCC Gran | | | | | | | | |
| 830774 | CITRIC ACID, 50% TAN NaOH, 50% (for pH adjustment) | | | | | | | | |
| Total | | 34.00 | 29.9 | 31.73 | 102.34 | 100.00 | 100.00 | 100.00 | 100.00 |
| % Active Surfactant | | 1.68 | 13.71 | 0.90 | 32.21 | 33.80 | 33.30 | 28.90 | 29.40 |
| % Active Amine Oxide | | | | | 0.9 | 6.90 | 6.90 | 6.90 | 6.90 |

| Code | POT AND PAN DEA REPLACEMENT | DEA replacement #70 | DEA replacement #71 | DEA replacement #72 | DEA replacement #73 | DEA replacement #74 | DEA replacement #75 | DEA replacement #76 | DEA replacement #77 | DEA replacement #78 |
|---|---|---|---|---|---|---|---|---|---|---|
| 100016 | Water Zeolite Softened TNK | 31.50 | 26.50 | 23.00 | 38.03 | 36.96 | 31.00 | 42.65 | 39.78 | 32.97 |
| 143040 | MgSO$_4$·7H$_2$O | | | | | 6.60 | 2.00 | | | |
| 175075 | LAS | | 15.00 | 15.00 | 22.03 | 26.00 | 26.00 | 22.00 | 22.00 | 15.00 |
| | KOH, 45% | | | | | | | | 8.06 | |
| 114132 | NaOH, 50% | | | | | | | | | |
| | Novel II C12-14 21EO SL-42 | 5.00 | 5.00 | 3.53 / 5.00 | 5.19 | 6.12 | 6.12 | 5.19 | | 3.53 / 5.00 |
| 164079 | ES 8965, PEI ethoxylate Propylene Glycol Technical DRM | 0.50 | 0.50 | 0.50 | | | | 0.50 | 0.50 | 0.50 |
| 830699/164006 173856 | Ethanol, SDA-3C DEA COCO AMIDE (1/1) IBC | 10.00 | | | 10.17 | 12.60 | 12.00 | 10.00 | 10.00 | 22.00 |
| 171405 | Sodium Lauryl Ether Ethoxylate Sulfate 60% | | | | | | | | | |
| 171318 | Sodium C14-16 Olefin Sulfonate TNK | 30.00 | 30.00 | 30.00 | | | | | | |

| | | | | | | | | | | |
|---|---|---|---|---|---|---|---|---|---|---|
| 172437 | LAURAMINE OXIDE 29-31% IBC | | 23.00 | | 23.00 | | 19.49 | 5.00 | 23.00 | |
| 171371 | Sodium Xylene Sulfonate 40% TNK | | | | | | 5.08 | 6.70 | 6.00 | |
| 830242/142010 | Sodium Chloride; FCC Gran | | | | | | | | | |
| 830774 | CITRIC ACID, 50% TAN NaOH, 50% (for pH adjustment) | | | | | | | | | |
| | Total | | 100.00 | 100.00 | 100.03 | | 100.00 | 99.98 | 106.12 | |
| | % Active Surfactant | | 30.40 | 38.80 | 38.80 | | 33.10 | 34.02 | 39.06 | |
| | % Active Amine Oxide | | 6.90 | 6.90 | 6.90 | | 5.85 | 1.50 | 6.90 | |

| | | % activity | Commercial Product 1 | Commercial Product 2 | Commercial Product 3 | DEA replacement #70 | DEA Replacement #78 | DEA Replacement #79 | DEA Replacement #80 | DEA Replacement #81 | DEA Replacement #82 | DEA Replacement #83 | DEA replacement #84 |
|---|---|---|---|---|---|---|---|---|---|---|---|---|---|
| | POT AND PAN DEA REPLACEMENT | | | | | | | | | | | | |
| 100016 | Water Zeolite Softened TNK | | | | | 31.50 | 32.97 | 27.50 | 27.50 | 26.50 | 27.50 | 26.50 | 36.50 |
| 175075 | LAS | 0.96 | | | | | 15.00 | | 1.50 | 2.50 | 4.00 | | |
| 114132 | NaOH, 50% | 0.8 | | | | | 3.53 | | 2.50 | 3.50 | | | |
| | Antil SPA 80 | 0.47 | | | | | | 4.00 | 5.00 | 0.50 | | 10.00 | 0.50 |
| | Tego Betaine C60 | 1 | | | | 5.00 | 5.00 | 5.00 | | | 10.00 | 0.50 | 10.00 |
| | Novel II C12-14 21EO | 1 | | | | 0.50 | 0.50 | | | | | | |
| | ES 8965, PEI ethoxylate | 0.6 | | | | 10.00 | 22.00 | 10.00 | 10.00 | 12.00 | 10.00 | 10.00 | |
| 171405 | Sodium Lauryl Ether Ethoxylate Sulfate 60% | | | | | | | | | | | | |
| 171318 | Sodium C14-16 Olefin Sulfonate TNK | 0.4 | | | | 30.00 | | 30.00 | 30.00 | 30.00 | 30.00 | 30.00 | 30.00 |
| 172437 | LAURAMINE OXIDE 29-31% IBC | 0.3 | | | | 23.00 | 23.00 | 23.00 | 23.00 | 23.00 | 23.00 | 23.00 | 23.00 |
| 830774 | CITRIC ACID, 50% TAN NaOH, 50% (for pH adjustment) | | | | | | | | | | | | |
| | Total | | 34.00 | 29.9 | 31.73 | 100.00 | 102.00 | 99.98 | 106.12 | 100.34 | 101.84 | 100.00 | 102.00 |
| | % Active Surfactant | | 1.68 | 13.71 | 0.90 | 30.40 | 40.00 | 34.02 | 39.06 | 33.62 | 34.07 | 35.40 | 40.00 |
| | % Active Amine Oxide | | | | | 6.9 | 6.9 | 1.50 | 6.9 | 6.00 | 6.45 | 6.9 | 6.9 |

| | | % activity | Commercial Product 1 | Commercial Product 2 | Commercial Product 3 | DEA Replacement #85 | DEA Replacement #86 | DEA Replacement #87 | DEA Replacement #88 | DEA Replacement #89 | DEA Replacement #70-2 | DEA Replacement #72-2 | DEA Replacement #90 |
|---|---|---|---|---|---|---|---|---|---|---|---|---|---|
| | POT AND PAN DEA REPLACEMENT | | | | | | | | | | | | |
| 100016 | Water Zeolite Softened TNK | 0.32 | | | | 35.50 | 34.15 | 49.15 | 35.50 | 35.50 | 31.50 | 22.97 | 31.50 |
| | Pluraflo AT-301 | 0.45 | | | | 1.00 | | | | | | | 1.00 |
| 171314 | Dehyton DC | 0.3 | | | | | | | 1.00 | | | | |
| 179002 | Dowfax 3B2 | 0.4 | | | | | | | | 1.00 | | | |
| | EsiTerge LHS | 0.96 | | | | | | | | | | | |
| 175075 | LAS | 1 | | | | | 10.00 | 10.00 | | | | 15.00 | |
| | NaOH, 50% | 1 | | | | | 2.35 | 2.35 | | | | 3.53 | |
| | Novel II C12-14 21EO | | | | | | 5.00 | 5.00 | | | 5.00 | 5.00 | 5.00 |
| | ES 8965, PEI ethoxylate | 0.6 | | | | 0.50 | 0.50 | 0.50 | 0.50 | 0.50 | 0.50 | 0.50 | 0.50 |
| 171405 | Sodium Lauryl Ether Ethoxylate Sulfate 60% | | | | | 10.00 | | 10.00 | 10.00 | 10.00 | 10.00 | 10.00 | 10.00 |

-continued

| | | | | | | | | | |
|---|---|---|---|---|---|---|---|---|---|
| 171318 Sodium C14-16 Olefin Sulfonate TNK | 0.4 | | | | | | | | |
| Sodium C14-16 Olefin Sulfonate (PILOT) | 0.4 | | | | 30.00 | 30.00 | 30.00 | 30.00 | 30.00 |
| 172437 LAURAMINE OXIDE 29-31% IBC | 0.3 | | | | 25.00 | | | | |
| 830774 CITRIC ACID, 50% TAN | | | | | | | | | |
| NaOH, 50% (for pH adjustment) | | | | | 23.00 | 23.00 | 23.00 | 23.00 | 23.00 |
| Total | | 34.00 | 29.9 | 31.73 | 100.00 | 100.00 | 100.00 | 100.00 | 100.00 |
| % Active Surfactant | | 1.68 | 13.71 | 0.90 | 32.00 | 28.00 | 25.80 | 25.70 | 30.40 | 38.80 | 18.72 |
| % Active Amine Oxide | | | | | 6.9 | 6.9 | 6.9 | 6.9 | 6.9 | 6.9 | 6.9 |

| POT AND PAN DEA REPLACEMENT | % active | Commercial Product 1 | Commercial Product 2 | Commercial Product 3 | DEA Replacement #20 | DEA Replacement #91 | DEA Replacement #92 | DEA Replacement #92 normalized | DEA Replacement #93 | DEA Replacement #93-2 | DEA Replacement #94 #41 w/ SXS | DEA Replacement #95 | DEA Replacement #96 | DEA Replacement #97 |
|---|---|---|---|---|---|---|---|---|---|---|---|---|---|---|
| 100016 Water Zeolite Softened TNK | | | | | 44.48 | 26.13 | 35.00 | 31.30 | 20.17 | 20.17 | 43.04 | 22.50 | 42.25 | 28.50 |
| 171371 Sodium Xylene Sulfonate 40% TNK | 1 | | | | 0.43 | 0.57 | | 0.51 | 0.57 | 0.57 | 0.43 | 0.50 | | 0.50 |
| 171405 Sodium Lauryl Ether Ethoxylate Sulfate 60% | 0.6 | | | | 10.21 | 13.58 | 13.58 | 12.14 | 13.58 | 13.58 | 10.21 | 13.00 | 12 | 13.00 |
| 171318 Sodium C14-16 Olefin Sulfonate TNK | 0.4 | | | | 25.32 | 33.68 | 33.68 | 30.12 | 33.68 | 33.68 | 25.32 | 34.00 | 29.75 | 34.00 |
| 171371 Sodium Xylene Sulfonate 40% TNK | 1 | | | | | | 6.00 | 5.37 | 6.00 | 6.00 | 6 | 6.00 | | |
| 172452 LAURAMINE OXIDE 29-31% IBC, | 0.3 | | | | 19.57 | 26.04 | 23.00 | 20.57 | 26.00 | 26.00 | 15 | 24.00 | 15 | 24.00 |
| Barlox 12 | | | | | | | | | | | | | | |
| 230268 Acusol 820 | | | | | | | | | | | | | 1 | |
| Total | | 34.00 | 29.9 | 31.73 | 100.01 | 100.00 | 111.83 | 100.00 | 100.00 | 100.00 | 100.00 | 100.00 | 100.00 | 100.00 |
| % Active Surfactant | | 1.68 | 13.71 | 0.90 | 22.55 | 30.00 | 29.09 | 26.01 | 22.19 | 29.99 | 21.18 | 29.10 | 23.60 | 29.10 |
| % Active Amine Oxide | | | | | 5.87 | 7.81 | 6.90 | 6.17 | 7.80 | 7.80 | 4.50 | 7.20 | 4.50 | 7.20 |

| POT AND PAN DEA REPLACEMENT | % active | DEA replacement #20 | DEA replacement #98 | DEA replacement #95 | DEA Replacement #99 | DEA Replacement #100 | DEA Replacement #101 | DEA Replacement #102 | DEA Replacement #103 | DEA replacement #104 | DEA Replacement #105 | DEA Replacement #106 | DEA Replacement #107 | DEA Replacement #108 | DEA Replacement #109 |
|---|---|---|---|---|---|---|---|---|---|---|---|---|---|---|---|
| 100016 Water Zeolite Softened TNK | | 44.21 | 19.86 | 22.24 | 22.19 | 22.14 | 22.09 | 22.04 | 21.99 | 21.94 | 21.89 | 21.84 | 21.79 | 21.74 | 41.74 |
| 171371 Sodium Xylene Sulfonate 40% TNK | | | 6.00 | 6.00 | 6.00 | 6.00 | 6.00 | 6.00 | 6.00 | 6.00 | 6.00 | 6.00 | 6.00 | 6.00 | |
| 175075 LAS | 0.96 | | | | | | | | | | | | | | 2.00 |
| 171318 Sodium C14-16 Olefin Sulfonate TNK | 0.4 | 25.32 | 33.68 | 34.00 | 34.00 | 34.00 | 34.00 | 34.00 | 34.00 | 34.00 | 34.00 | 34.00 | 34.00 | 34.00 | 25.32 |
| 171405 Sodium Lauryl Ether Ethoxylate Sulfate 60% | 0.6 | 10.21 | 13.58 | 13.00 | 13.00 | 13.00 | 13.00 | 13.00 | 13.00 | 13.00 | 13.00 | 13.00 | 13.00 | 13.00 | 10.21 |
| ES 8965, PEI ethoxylate | 1 | 0.43 | 0.57 | 0.50 | 0.55 | 0.60 | 0.65 | 0.70 | 0.75 | 0.80 | 0.85 | 0.90 | 0.95 | 1.00 | 0.43 |
| 172452 LAURAMINE OXIDE 29-31% IBC, Barlox 12 | 0.3 | 19.57 | 26.04 | 24.00 | 24.00 | 24.00 | 24.00 | 24.00 | 24.00 | 24.00 | 24.00 | 24.00 | 24.00 | 24.00 | 19.57 |
| 230268 Acusol 820 | | | | | | | | | | | | | | | |
| 114132 NaOH | | | | | | | | | | | | | | | 0.47 |
| Total | | 100.00 | 100.00 | 100.00 | 100.00 | 100.00 | 100.00 | 100.00 | 100.00 | 100.00 | 100.00 | 100.00 | 100.00 | 100.00 | 100.00 |
| % Active Surfactant | | 22.55 | 30.00 | 29.10 | 29.15 | 29.20 | 29.25 | 29.30 | 29.35 | 29.40 | 29.45 | 29.50 | 29.55 | 29.60 | 24.47 |
| % Active Amine Oxide | | 5.87 | 7.81 | 7.20 | 7.20 | 7.20 | 7.20 | 7.20 | 7.20 | 7.20 | 7.20 | 7.20 | 7.20 | 7.20 | 5.87 |

-continued

| | POT AND PAN DEA REPLACEMENT | % active | DEA replacement #110 | DEA replacement #111 | DEA replacement #112 | DEA replacement #113 | DEA replacement #114 | DEA replacement #115 | DEA replacement #116 | DEA replacement #117 | DEA replacement #118 | DEA replacement #119 | DEA replacement #120 |
|---|---|---|---|---|---|---|---|---|---|---|---|---|---|
| 100016 | Water Zeolite Softened | | 23.50 | 23.50 | 23.50 | 23.50 | 23.50 | 23.50 | 23.50 | 22.50 | 26.50 | 26.50 | 54.25 |
| 230268 | Acusol 820 | | | | | | | | | | | | 1.00 |
| 171371 | SXS, 40% | 0.4 | | | | | | | | | | | |
| 171318 | AOS, 40% | 0.6 | 34.00 | 34.00 | 34.00 | 34.00 | 34.00 | 34.00 | 34.00 | 34.00 | 34.00 | 34.00 | 24.75 |
| 171405 | SLES, 60% | 1 | 13.00 | 13.00 | 13.00 | 13.00 | 13.00 | 13.00 | 13.00 | 13.00 | 13.00 | 13.00 | 12.00 |
| | ES 8965, PEI ethoxylate | 0.3 | 0.50 | 0.50 | 0.50 | 0.50 | 0.50 | 0.50 | 0.50 | 0.50 | 0.50 | 0.50 | |
| 172452 | BARLOX12, 30% | | 24.00 | 24.00 | 24.00 | 24.00 | 24.00 | 24.00 | 24.00 | 24.00 | 24.00 | 24.00 | 3.00 |
| 230268 | Acusol 820 | 1 | | | | | | | | | | | |
| 172063 | SL-62 | 0.99 | | | 5.00 | | | | | | | | |
| | EH-9 | 0.9 | | | | | | | | | | | |
| | MARLOWET 4539 | 1 | | 5.00 | | | | | | | | | |
| 170322 | PLURONIC N-3 | 0.5 | 5.00 | | | | | | | | | | |
| | Naxan DIL | 0.97 | | | | 5 | | | | | | | |
| 170175 | Tween 20 | 1 | | | | | 5 | | | | | | |
| 178251 | ethylan HB-4 | 0.4 | | | | | | 5 | | | | | |
| 175422 | Naxonate, 40% | 0.5 | | | | | | | 5 | | | | |
| 170030 | Petro LULF | | | | | | | | | 6 | | | |
| 171314 | Dowfax 3B2 | 1 | | | | | | | | | 2 | | |
| | T-MAZ 80 | | | | | | | | | | | 2 | 5 |
| | Total | | 100.00 | 100.00 | 100.00 | 100.00 | 100.00 | 100.00 | 100.00 | 100.00 | 100.00 | 100.00 | 100.00 |
| | % Active Surfactant | | 34.10 | 33.60 | 34.10 | 31.60 | 33.95 | 31.60 | 31.10 | 35.04 | 31.08 | 29.10 | 23.00 |
| | % Active Amine Oxide | | 7.20 | 7.20 | 7.20 | 7.20 | 7.20 | 7.20 | 7.20 | 7.20 | 7.20 | 7.20 | 0.90 |

| | POT AND PAN DEA REPLACEMENT | % active | DEA replacement #120 | DEA replacement #121 | DEA replacement #122 | DEA replacement #123 | DEA replacement #124 | DEA replacement #128 | DEA replacement #129 | DEA replacement #130 | DEA replacement #131 | DEA replacement #132 |
|---|---|---|---|---|---|---|---|---|---|---|---|---|
| 100016 | Soft Water | | 54.25 | 54.29 | 49.25 | 49.25 | 49.25 | 26.00 | 26.00 | 26.00 | 26.00 | 27.00 |
| 230268 | Acusol 820 | 0.6 | 1.00 | 1.00 | 1.00 | 1.00 | 1.00 | 1.00 | 1.00 | 1.00 | 1.00 | |
| 171405 | SLES, 60% | 0.4 | 12 | 12 | 12 | 12 | 12 | 12 | 12 | 12 | 12 | 12 |
| 171318 | AOS, 40% | 0.3 | 24.75 | 24.75 | 24.75 | 24.75 | 24.75 | 30 | 30 | 30 | 30 | 30 |
| 172452 | Barlox 12, 30% | 1 | 3 | 3 | 3 | 3 | 3 | 20 | 20 | 20 | 20 | 20 |
| | T-maz 80 | 1 | 5 | 5 | | | | 5 | | | | |
| | TX14574 (Nalco 5790-82-16H PG) | 1 | | | 5 | | | | 5 | | | |
| | TX14574 (Nalco 6017-192 CLPG) | 1 | | | | 5 | | | | 5 | | |
| | TX14574 (Nalco 6379-058 CPG) | 0.4 | | | | | 5 | | | | 5 | |
| 171371 | SXS, 40% | | | | | | | 6 | 6 | 6 | 6 | 6 |
| | Total | | 100.00 | 105.04 | 100.00 | 100.00 | 100.00 | 100.00 | 100.00 | 100.00 | 100.00 | 100.00 |
| | % Active Surfactant | | 23.00 | 23.00 | 23.00 | 23.00 | 23.00 | 30.20 | 30.20 | 30.20 | 30.20 | 30.20 |
| | % Active Amine Oxide | | 0.90 | 0.90 | 0.90 | 0.90 | 0.90 | 6.00 | 6.00 | 6.00 | 6.00 | 6.00 |

-continued

| POT AND PAN DEA REPLACEMENT | | % active | DEA replacement #9 | DEA replacement #120 | DEA replacement #128 | DEA replacement #133 | DEA replacement #134 | DEA replacement #135 | DEA replacement #136 (#9 w/o PEI) |
|---|---|---|---|---|---|---|---|---|---|
| 100016 | Soft Water | | 54.25 | 54.25 | 26.00 | 55.25 | 55.25 | 27.00 | 55.25 |
| 230268 | Acusol 820 | | 1.00 | 1.00 | 1.00 | | | | |
| 171318 | AOS, 40% | 0.4 | 29.75 | 24.75 | 30 | 29.75 | 24.75 | 30 | 29.75 |
| 171405 | SLES, 60% | 0.6 | 12 | 12 | 12 | 12 | 12 | 12 | 12 |
| 172452 | Barlox 12, 30% | 0.3 | 3 | 3 | 20 | 3 | 3 | 23 | 3 |
| | T-maz 80 | 1 | | 5 | | | 5 | 5 | |
| 171371 | SXS, 40% | 0.4 | | | 6 | | | 6 | |
| Total | | | 100.00 | 100.00 | 100.00 | 100.00 | 100.00 | 103.00 | 100.00 |
| % Active Surfactant | | | 20.00 | 23.00 | 30.20 | 20.00 | 23.00 | 31.10 | 20.00 |
| % Active Amine Oxide | | | 0.90 | 0.90 | 6.00 | 0.90 | 0.90 | 6.90 | 0.90 |

| POT AND PAN DEA REPLACEMENT | | % active | DEA replacement #137 | DEA replacement #138 | DEA replacement #139 | DEA replacement #140 | DEA replacement #141 |
|---|---|---|---|---|---|---|---|
| 100016 | Water Zeolite Softened TNK | | 54.25 | 54.25 | 54.25 | 31.25 | 31.25 |
| 171371 | SXS (Sodium Xylene Sulfonate 40% TNK) | 1 | 0 | 1 | 1 | 6.00 | 6.00 |
| 230268 | Acusol 820 | | 1 | | | 1 | 1 |
| | Sokalan HP 25 | | | | | | |
| | Nalco TX-14980SQ, 6379-063 | 0.52 | | | | | |
| | Nalco TX-14980SQ, 6379-064 | 0.48 | | 5 | 5 | 5 | 5 |
| 171318 | AOS (Sodium C14-16 Olefin Sulfonate 40% TNK) | 0.4 | 24.75 | 24.75 | 24.75 | 24.75 | 24.75 |
| 170654 | Tween 80K | 1 | 5 | | | | |
| 171405 | SLES (Sodium Lauryl Ether Ethoxylate Sulfate 60%) | 0.6 | 12.00 | 12.00 | 12.00 | 12.00 | 12.00 |
| 172452 | Barlox 12 (LAURAMINE OXIDE 29-31% IBC) | 0.3 | 3.00 | 3.00 | 3.00 | 20.00 | 20.00 |
| Total | | | 100.00 | 100.00 | 100.00 | 100.00 | 100.00 |
| % Active Surfactant | | | 23.00 | 20.60 | 20.40 | 25.70 | 25.50 |
| % Active Amine Oxide | | | 0.90 | 0.90 | 0.90 | 6.00 | 6.00 |

| POT AND PAN DEA REPLACEMENT | | % active | Commercial Product 3 | DEA replacement #142 | DEA replacement #143 | DEA replacement #144 | DEA replacement #95 | DEA replacement #145 |
|---|---|---|---|---|---|---|---|---|
| 100016 | Water Zeolite Softened TNK | | | 22.50 | 22.50 | 22.50 | 22.50 | 30.50 |
| | ES 8965, PEI ethoxylate | 1 | | 0.50 | | | 0.50 | 0.50 |
| | VX9945 (Nalco PEI) | 1 | | | 0.50 | | | |
| | VX9946 (Nalco PEI) | 1 | | | | 0.50 | | |
| | VX10035 (Nalco PEI) | 1 | | | | | | |
| 171405 | Sodium Lauryl Ether Ethoxylate Sulfate 60% | 0.6 | | 13.00 | 13.00 | 13.00 | 13.00 | 13.00 |

-continued

| | | | | | | | |
|---|---|---|---|---|---|---|---|
| 171318 | Sodium C14-16 Olefin Sulfonate TNK | 0.4 | 34.00 | 34.00 | 34.00 | 34.00 | 34.00 | 34.00 |
| 171371 | Sodium Xylene Sulfonate 40% TNK | 0.3 | 6.00 | 6.00 | 6.00 | 6.00 | 6.00 | 6.00 |
| 172452 | LAURAMINE OXIDE 29-31% IBC, Barlox 12 | | 24.00 | 24.00 | 24.00 | 24.00 | 24.00 | 0.00 |
| 230268 | Acusol 820 | 0.45 | | | | | | |
| 177105 | Cocamidopropylbetaine | | | | | | | 16 |
| Total | | | 100.00 | 100.00 | 100.00 | 100.00 | 100.00 | 100.00 |
| % Active Surfactant | | 31.73 | 29.10 | 29.10 | 29.10 | 29.10 | 29.10 | 29.10 |
| % Active Amine Oxide | | 0.90 | 7.20 | 7.20 | 7.20 | 7.20 | 7.20 | 0.00 |

(I) Foam Results with Fixed Weight Dosing:

The foregoing tests and FIGS. 1-10 shows that those compositions with and without a low level Sokalan HP-20 (~0.5%) or Acusol 820 (~1%) quite often show the benefit of the incorporation of even such a low level of these two types of polymer.

| ACTIVE SURFACTANT VS FOAM HEIGHT | | | | | | |
|---|---|---|---|---|---|---|
| ID | % Active surfactant | Foam ht (mls) 0 gr soft water 80° F. | Foam ht (mls) 0 gr soft water, 110° F. | Foam ht (mls) 5 gr city water, 80° F. | Foam ht (mls) 5 gr city water, 110° F. | ppm active surfactant in foam test |
| Control - Commercial Product #3 | 31.73 | | 255, 267 | | | 247 |
| Control - Commercial Product #3 | 31.73 | 611 | | 413*, 396, 175 | 292, 272 | 500 |
| Commercial Product #2 | 29.90 | | 196 | | | 233 |
| Commercial Product #2 | 29.90 | | | 417, 355 | 259 | 500 |
| Commercial Product #1 | 34.00 | | 289 | | | 270 |
| Commercial Product #1 | 34.00 | | | 413, 487, 512 | 320, 303 | 500 |
| DEA replacement #6 | 20.00 | | 76 | | | 156 |
| DEA replacement #9 | 20.00 | | 211, 161 | | | 156 |
| DEA replacement #10 | 20.00 | | 198 | | | 156 |
| DEA replacement #11 | 20.00 | | 175 | | | 156 |
| DEA replacement #12 | 20.00 | | 104 | | | 156 |
| DEA replacement #13 | 20.00 | | 157 | | | 156 |
| DEA replacement #14 | 20.50 | | 195, 231 | | | 160 |
| DEA replacement #15 | 20.00 | | 151 | | | 156 |
| DEA replacement #19 | 20.00 | | 183 | | | 156 |
| DEA replacement #20 | 22.55 | | 243 | | | 176 |
| DEA replacement #21 | 20.50 | | 193 | | | 160 |
| DEA replacement #25 | 20.50 | | 178 | | | 160 |
| DEA replacement #26 | 26.50 | | 243 | | | 207 |
| DEA replacement #27 | 20.00 | | 180 | | | 156 |
| DEA replacement #29 | 26.50 | | 263 | | | 207 |
| DEA replacement #32 | 18.80 | | 200 | | | 147 |
| DEA replacement #34 | 20.50 | | 137 | | | 160 |
| DEA replacement #38 | 20.50 | | 132 | | | 160 |
| DEA replacement #40 | 22.68 | | 219 | | | 177 |
| DEA replacement #41 | 21.18 | | 225 | | | 165 |
| DEA replacement #42 | 19.68 | | 201 | | | 153 |
| DEA replacement #43 | 18.18 | | 170 | | | 142 |
| DEA replacement #45 | 26.50 | | 262 | | | 207 |
| DEA replacement #46 | 25.00 | | 162 | | | 195 |
| DEA replacement #47 | 31.00 | | 255 | | | 242 |
| DEA replacement #48 | 32.21 | | 275 | | | 251 |
| DEA replacement #55 | 32.40 | | 243 | | | 253 |
| DEA replacement #59 | 26.90 | | 187 | | | 210 |
| DEA replacement #60 | 27.90 | | 230 | | | 218 |
| DEA replacement #62 | 28.40 | | 217 | | | 222 |
| DEA replacement #63 | 30.40 | | 202 | | | 237 |
| DEA replacement #64 | 34.10 | | 206 | | | 266 |
| DEA replacement #65 | 33.80 | | 318 | | | 264 |
| DEA replacement #66 | 33.30 | | 286 | | | 260 |
| DEA replacement #68 | 28.90 | | 249 | | | 225 |
| DEA replacement #69 | 29.40 | | 239 | | | 229 |
| DEA replacement #70 | 30.40 | | 291, 247 | | | 237 |
| DEA replacement #71 | 38.80 | | 277 | | | 303 |
| DEA replacement #72 | 38.80 | | 301 | | | 303 |
| DEA replacement #73 | 33.10 | | 287 | | | 258 |
| DEA replacement #83 | 35.40 | | 274 | | | 276 |
| DEA replacement #84 | 25.40 | | 257 | | | 198 |
| DEA replacement #85 | 25.72 | | 220 | | | 201 |
| DEA replacement #87 | 28.00 | | 247 | | | 218 |
| DEA replacement #88 | 25.80 | | 271 | | | 201 |
| DEA replacement #89 | 25.70 | | 267 | | | 200 |
| DEA replacement #9 | 20.00 | | | 480*, 275 | 347, 258 | 500 |
| DEA replacement #14 | 20.50 | | | 645* | 357 | 500 |
| DEA replacement #20 | 22.55 | 697 | | 746*, 370, 485 | 363 | 500 |
| DEA replacement #26 | 26.50 | | | 532* | 347 | 500 |
| DEA replacement #41 | 21.18 | | | 728* | 343 | 500 |
| DEA replacement #45 | 26.50 | | | 714* | 340 | 500 |
| DEA replacement #65 | 33.80 | | | 267, 390 | 366 | 500 |

-continued

| ACTIVE SURFACTANT VS FOAM HEIGHT | | | | | | |
|---|---|---|---|---|---|---|
| ID | % Active surfactant | Foam ht (mls) 0 gr soft water 80° F. | Foam ht (mls) 0 gr soft water, 110° F. | Foam ht (mls) 5 gr city water, 80° F. | Foam ht (mls) 5 gr city water, 110° F. | ppm active surfactant in foam test |
| DEA replacement #65 without PEI | 33.30 | | | 365 | | 500 |
| DEA replacement #72 | 38.80 | | | 456 | 343 | 500 |
| DEA replacement #95 | 29.10 | 570 | | 423, 426, 463, 437, 357 | 313, 293, 303, 317 | 500 |
| DEA replacement #95 without PEI | 28.60 | 530 | | 513, 405 | 305 | 500 |
| DEA replacement #96 | 23.60 | | | 387 | 297 | 500 |
| DEA replacement #97 | 29.10 | | | 427 | 323 | 500 |
| DEA replacement #98 | 30.00 | | | 343 | | 500 |
| DEA replacement #95 | 29.10 | | | | | 500 |
| DEA replacement #99 | 29.15 | | 721 | 469 | | 500 |
| DEA replacement #100 | 29.20 | | 634 | 395 | | 500 |
| DEA replacement #101 | 29.25 | | | 413 | | 500 |
| DEA replacement #102 | 29.30 | | 454 | 393 | | 500 |
| DEA replacement #103 | 29.35 | | 499 | 401 | | 500 |
| DEA replacement #104 | 29.40 | | 551 | 374 | | 500 |
| DEA replacement #105 | 29.45 | | 562 | 407 | | 500 |
| DEA replacement #106 | 29.50 | | 554 | 421 | | 500 |
| DEA replacement #107 | 29.55 | | 556 | 427 | | 500 |
| DEA replacement #108 | 29.60 | | 585 | 403 | | 500 |
| DEA replacement #109 | 24.47 | | | 342 | | 500 |
| DEA replacement #120 | 23.00 | | | 412 | 282 | 500 |
| DEA replacement #122 | 23.00 | | | | 291 | 500 |
| DEA replacement #123 | 23.00 | | | | 193 | 500 |
| DEA replacement #124 | 23.00 | | | | 180 | 500 |
| DEA replacement #128 | 30.20 | | | 283 | 200 | 500 |
| DEA replacement #129 | 30.20 | | | 307 | 269 | 500 |
| DEA replacement #130 | 30.20 | | | 315 | 292 | 500 |
| DEA replacement #131 | 30.20 | | | 299 | 245 | 500 |
| DEA replacement #132 | 30.20 | | | | 242 | 500 |
| DEA replacement #142 | 29.10 | | | 361 | 306 | 500 |
| DEA replacement #143 | 29.10 | | | 396 | 283 | 500 |
| DEA replacement #144 | 29.10 | | | 429 | 291 | 500 |
| DEA replacement #145 | 29.10 | | | 268 | 312 | 500 |

Example 2

Foam Results with Fixed Active Surfactant Concentration Dosing

The following foam results were obtained with fixed active surfactant concentration dosing, so the effectiveness of each surfactant/polymer system can be more easily compared.

FIGS. 11, 12, 13, and 14 clearly show the benefit of enhanced foam when using the PEI ethoxylate. Specifically comparing the Commercial Product 3 control formula to formula #14, they are identical except the 11.7% active cocamide DEA in the control is replaced with the 0.5% (as is) Sokalan HP-20.

Figure 11:
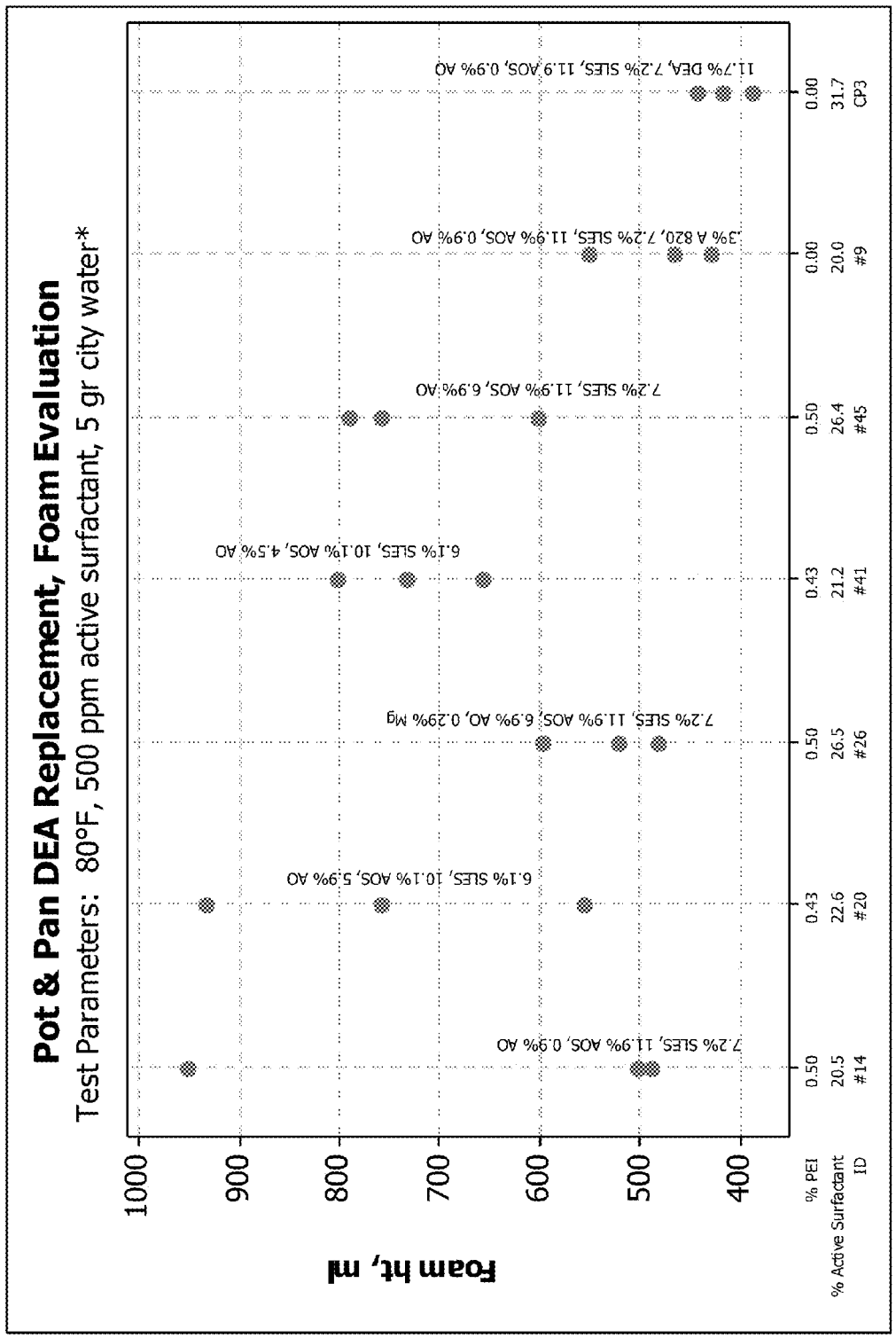
FIG. 11 is a graph showing foam height for formulas 9, 14, 20, 26, 41, and 45 with Commercial Product 3.

Additionally, by increasing the amine oxide when using the PEI ethoxylate serves to increase the total foam even more as can be seen in FIG. 11 with formulas #20, #26, #41, and #45.

Figure 12:
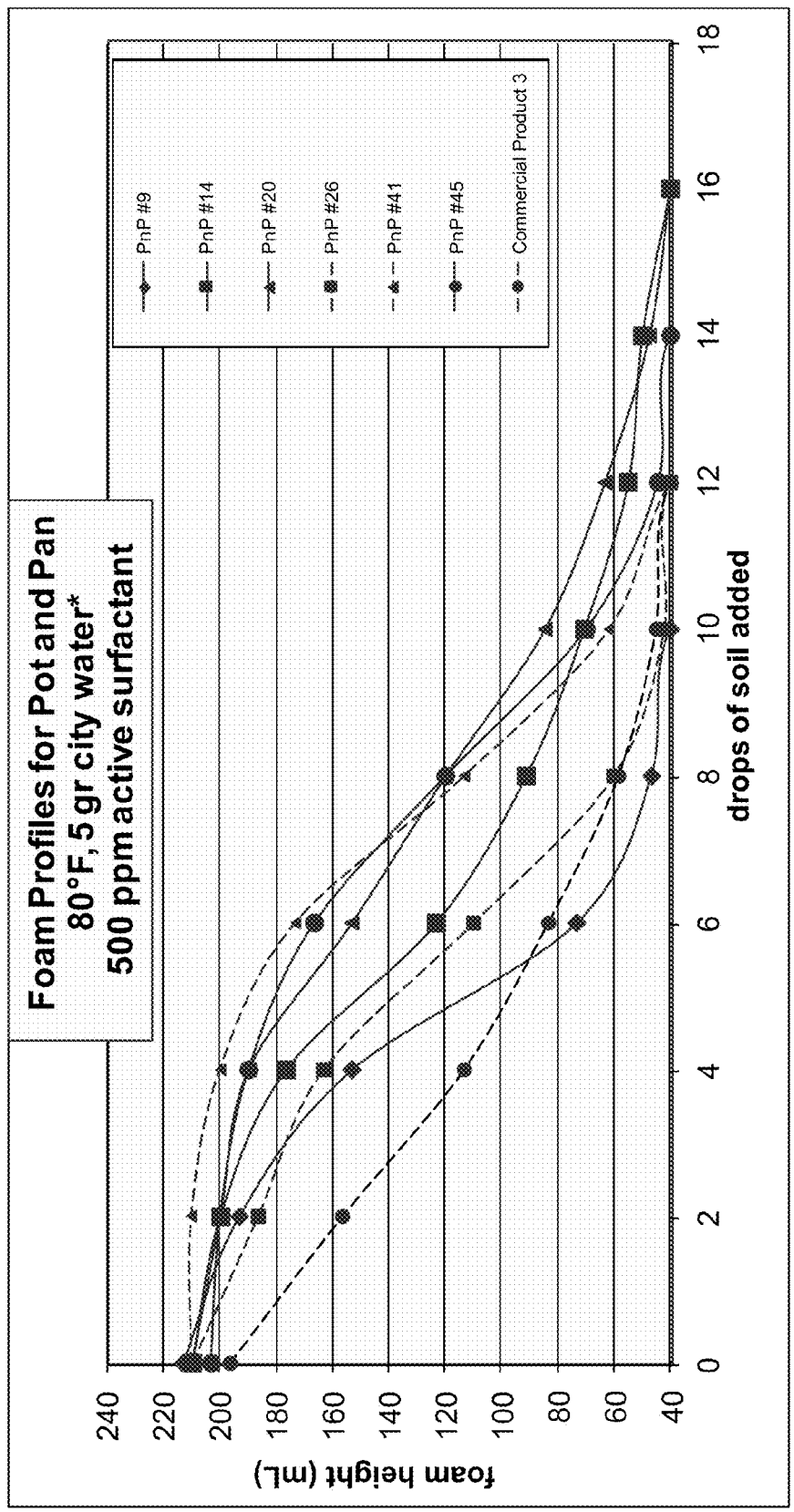
FIG. 12 is a graph depicting foam height as drops of soil are added for formulas 9, 14, 20, 26, 41, 45, and Commercial Product 3.
Figure 13:
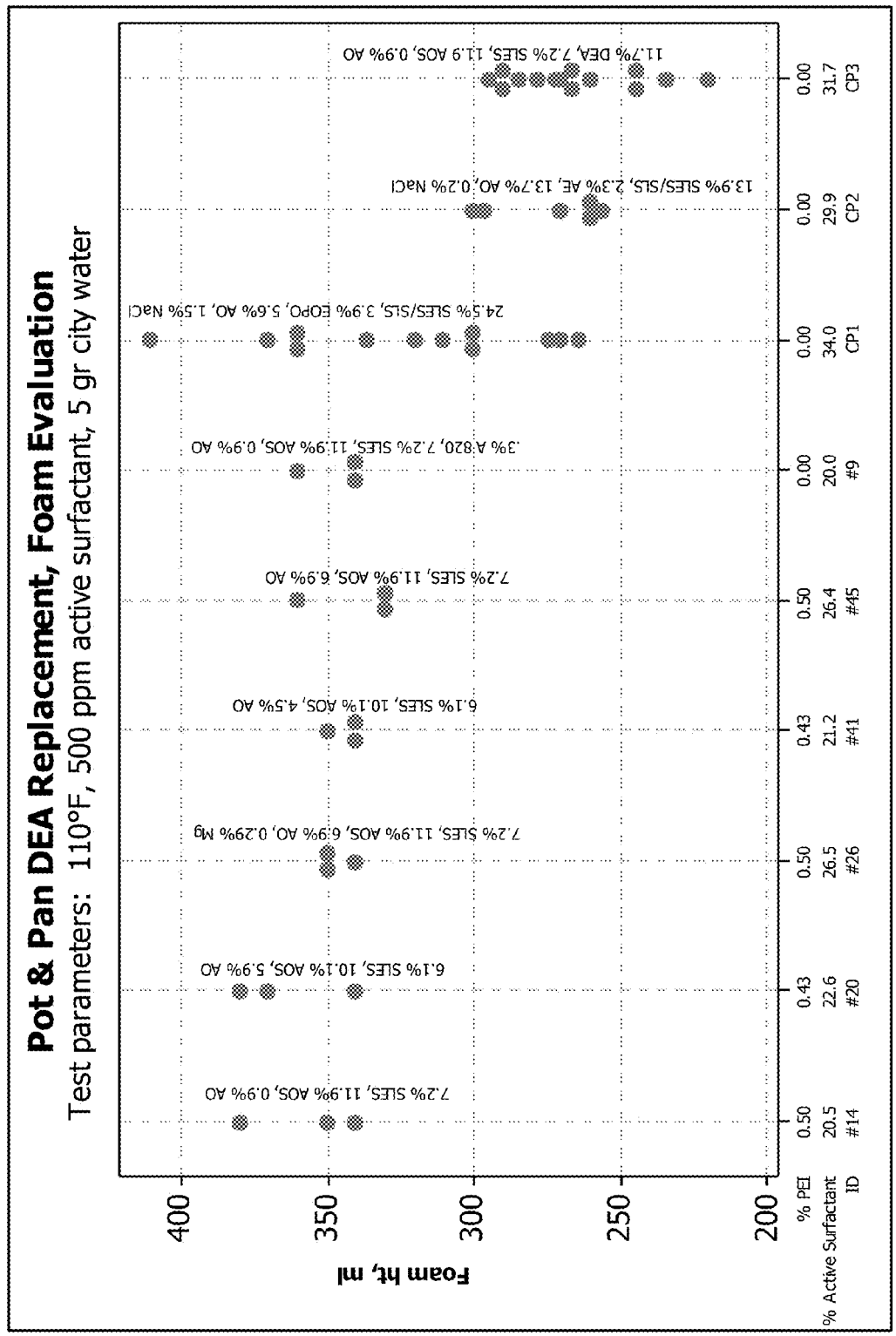
FIG. 13 is a graph showing foam height for formulas 9, 14, 20, 26, 41, and 45 with commercially available foaming pot and pan cleaning products Commercial Product 1 and Commercial Product 2 (which include PEI-14 PEG-10/PPG-7) and Commercial Product 3.
Figure 14:
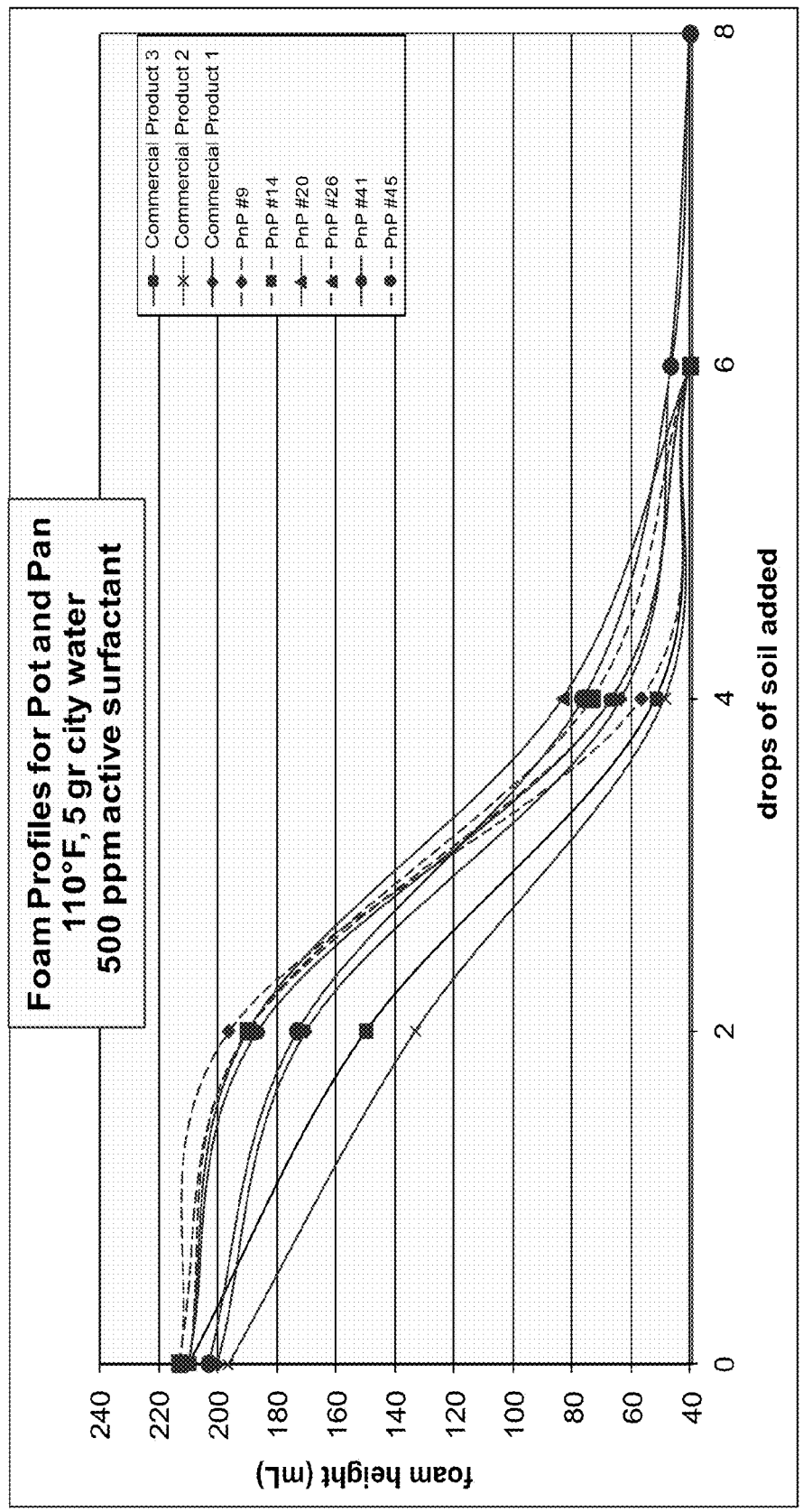
FIG. 14 is a graph depicting foam height as drops of soil are added for Commercial Product 1 and Commercial Product 2 (which include PEI-14 PEG-10/PPG-7) and Commercial Product 3, and formulas 9, 14, 20, 26, 41, and 45.

FIGS. 13 and 14 show the same results as FIGS. 11 and 12 but at 110° F. instead of 80° F., that the PEI ethoxylate as a foam enhancement replacement for DEA is feasible and in fact is actually superior to cocamide DEA.

Figure 15:
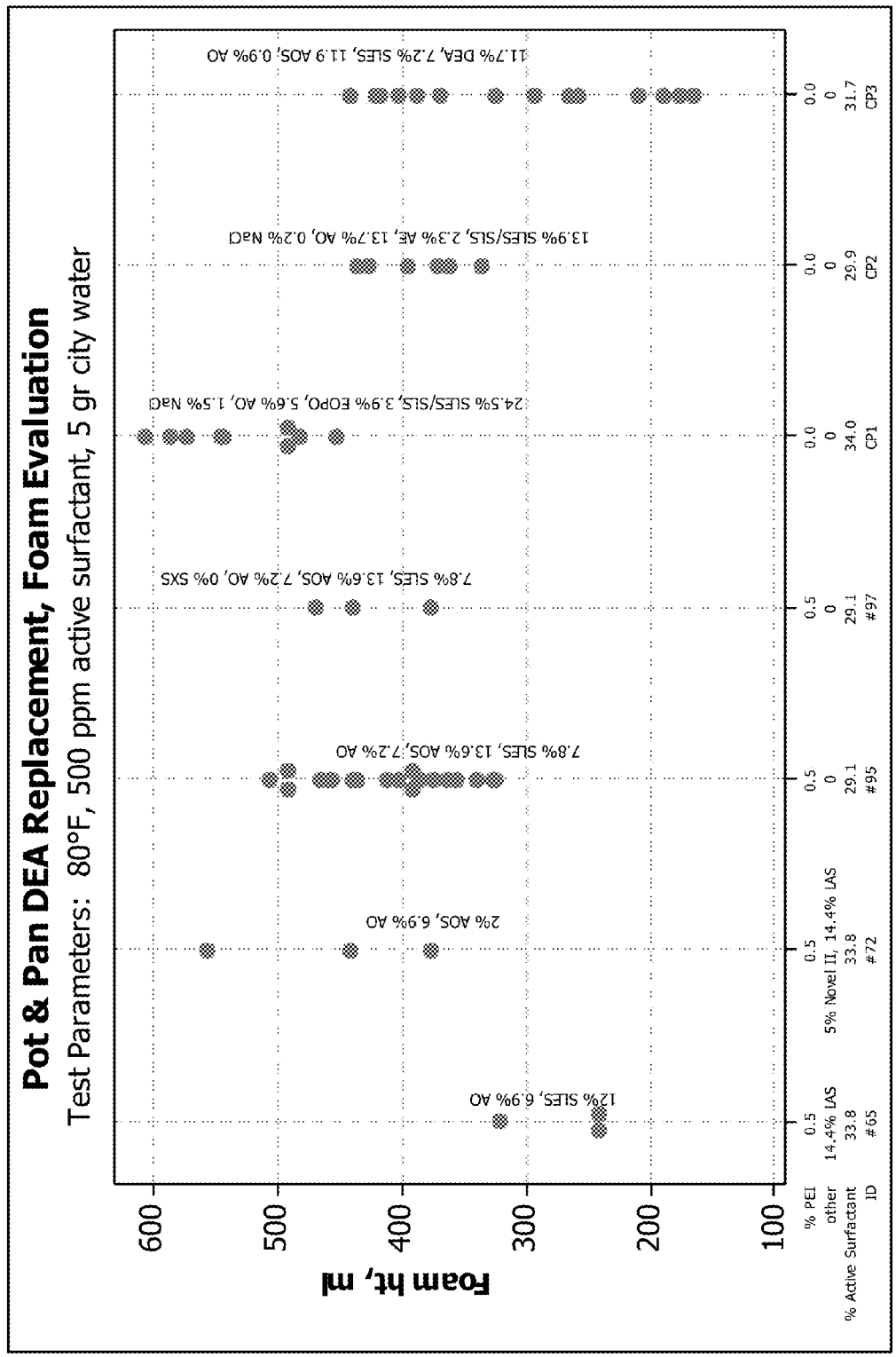
FIG. 15 is a graph showing foam height for formulas 65, 72, 95 and 97 with commercially available foaming pot and pan cleaning products Commercial Product 1 and Commercial Product 2 (which include PEI-14 PEG-10/PPG-7) and Commercial Product 3 at 80 Degrees F.
Figure 16:
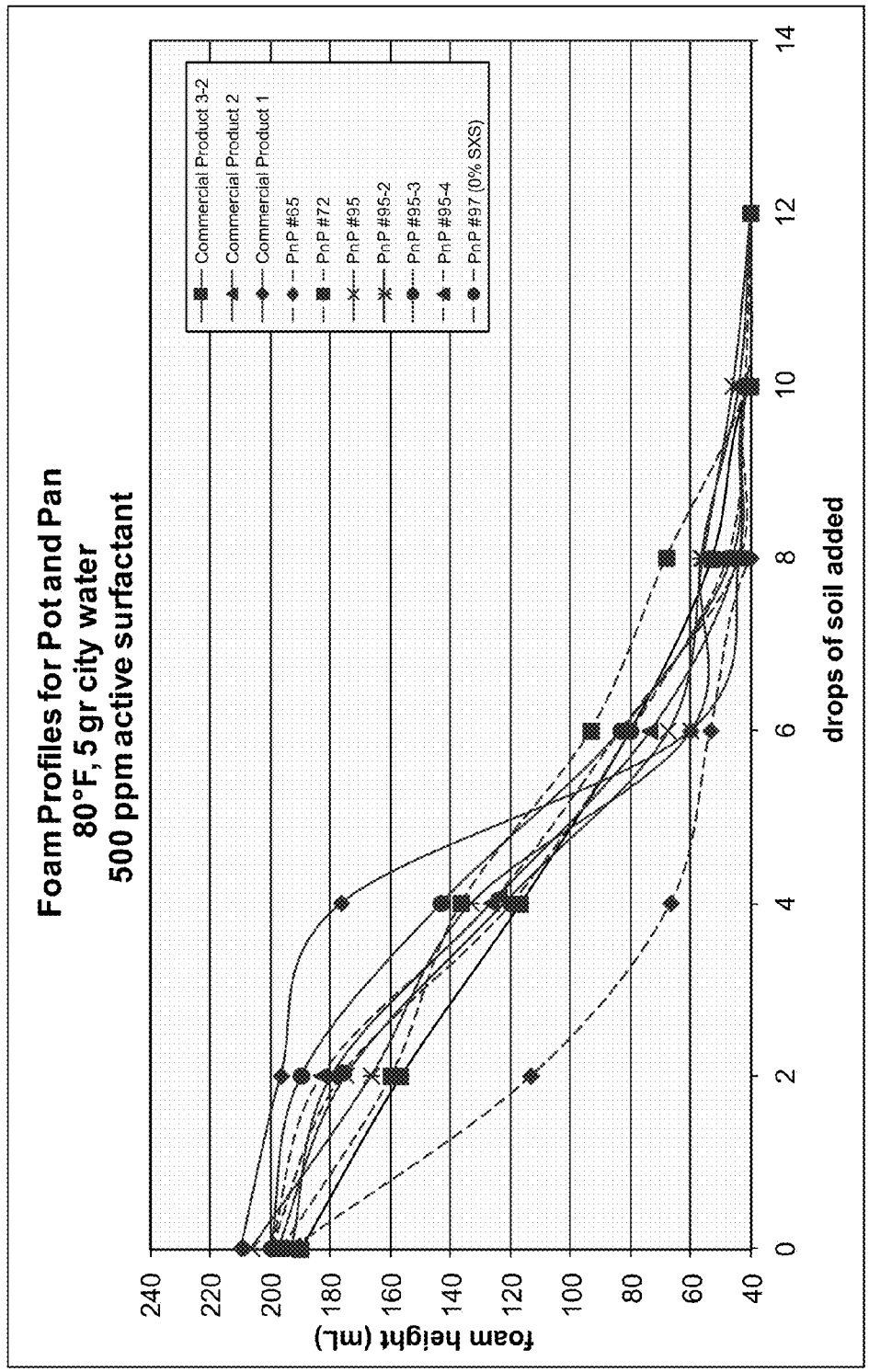
FIG. 16 is a graph depicting foam height as drops of soil are added for Commercial Product 1 and Commercial Product 2 (which include PEI-14 PEG-10/PPG-7) and Commercial Product 3, and formulas 65, 72, 95, 95-2, 95-3, 95-4, and 97 at 80 degrees F.

FIGS. 15 and 16 shows that the foam test is very reproducible and the PEI ethoxylate containing formulas show enhanced foam at 80° F.

Figure 17:
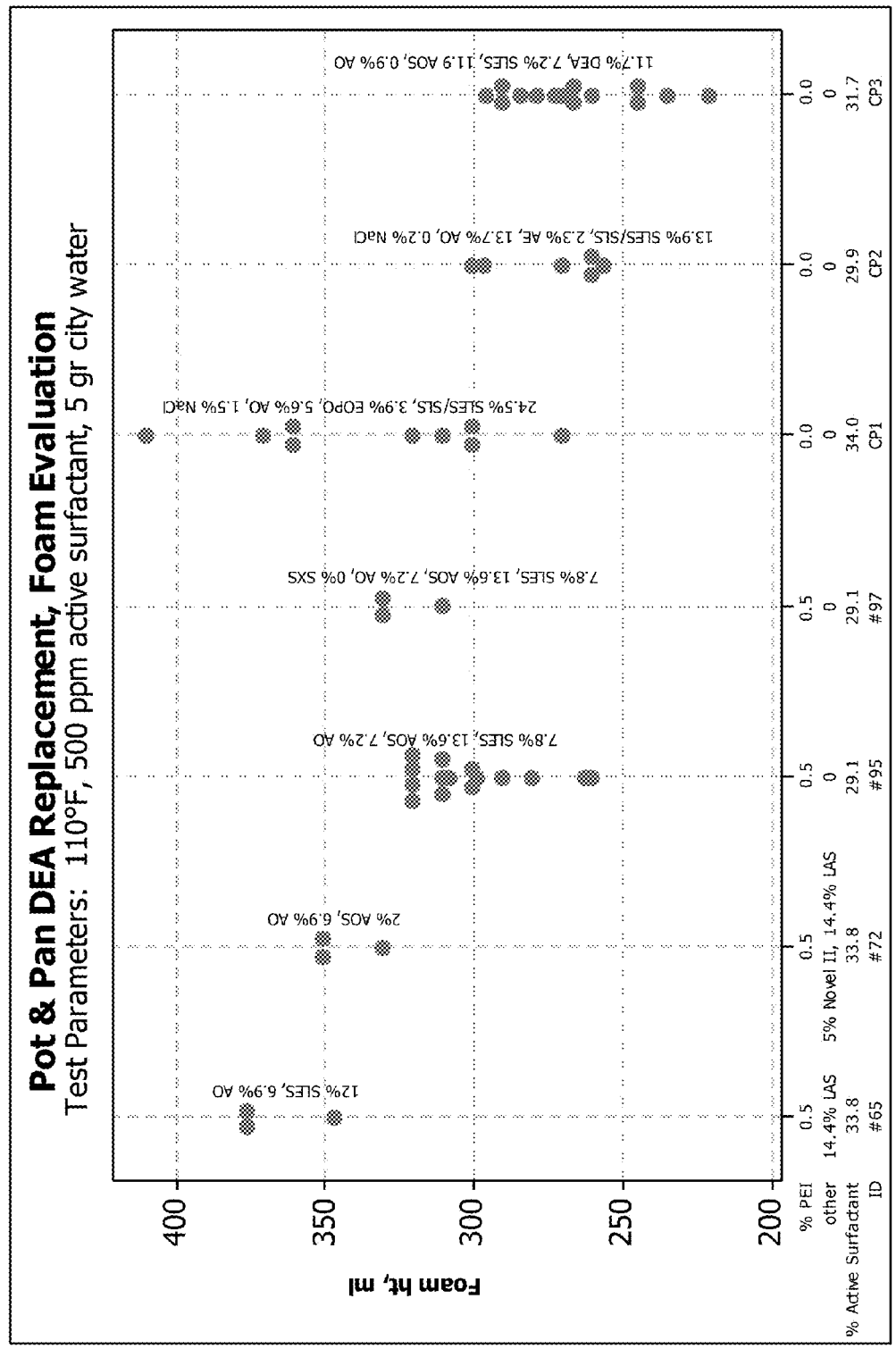
FIG. 17 is a graph showing foam height for formulas 65, 72, 95, and 97 with commercially available foaming pot and pan cleaning products Commercial Product 1 and Commercial Product 2 (which include PEI-14 PEG-10/PPG-7) and Commercial Product 3 at 110 degrees F.
Figure 18:
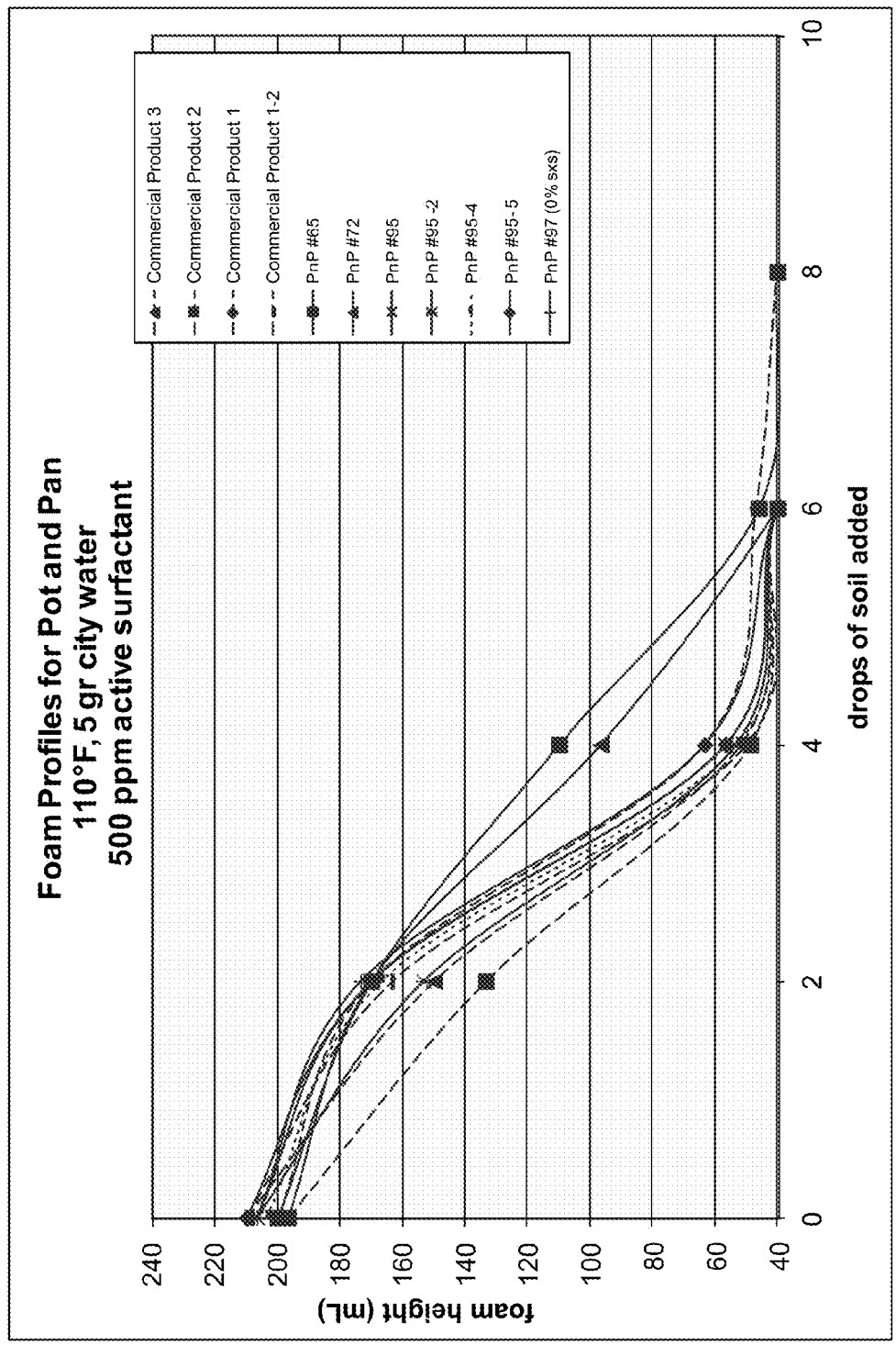
FIG. 18 is a graph depicting foam height as drops of soil are added for Commercial Product 1 and Commercial Product 2 (which include PEI-14 PEG-10/PPG-7) and Commercial Product 3, and formulas 65, 72, 95, 95-2, 95-3, 95-4, and 97 at 110 degrees F.

FIGS. 17 and 18 again show the same results that our foam test is reproducible and that the PEI ethoxylate containing formulas have enhanced foam but at 110° F.

Figure 19:
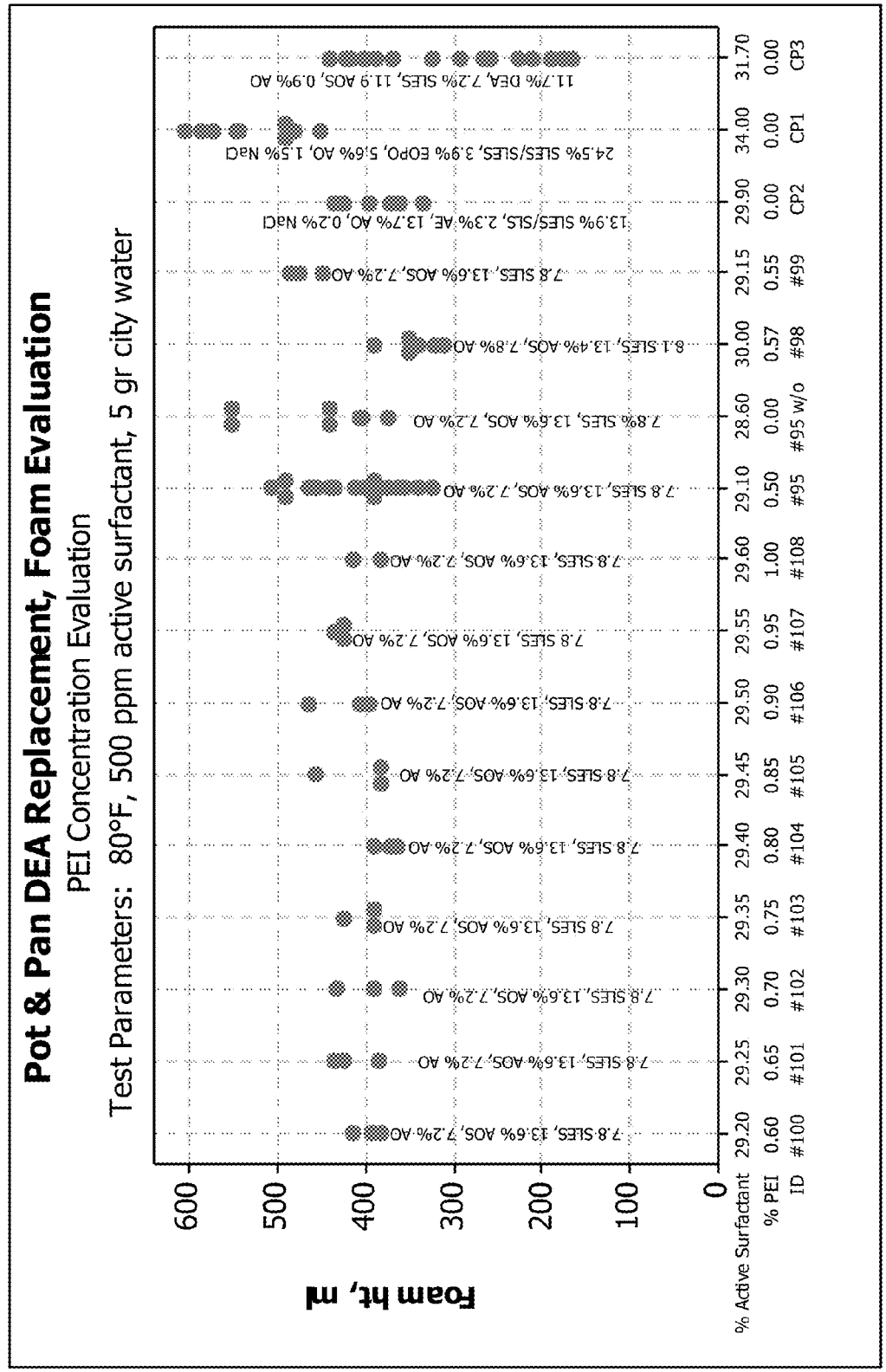
FIG. 19 is a graph showing foam height for formula 95 with and without PEI, 99, 98, 100, 101, 102, 103, 104, 105, 106, 107, and 108 with commercially available foaming pot and pan cleaning products Commercial Product 1 and Commercial Product 2 (which include PEI-14 PEG-10/PPG-7) and Commercial Product 3.
Figure 20:
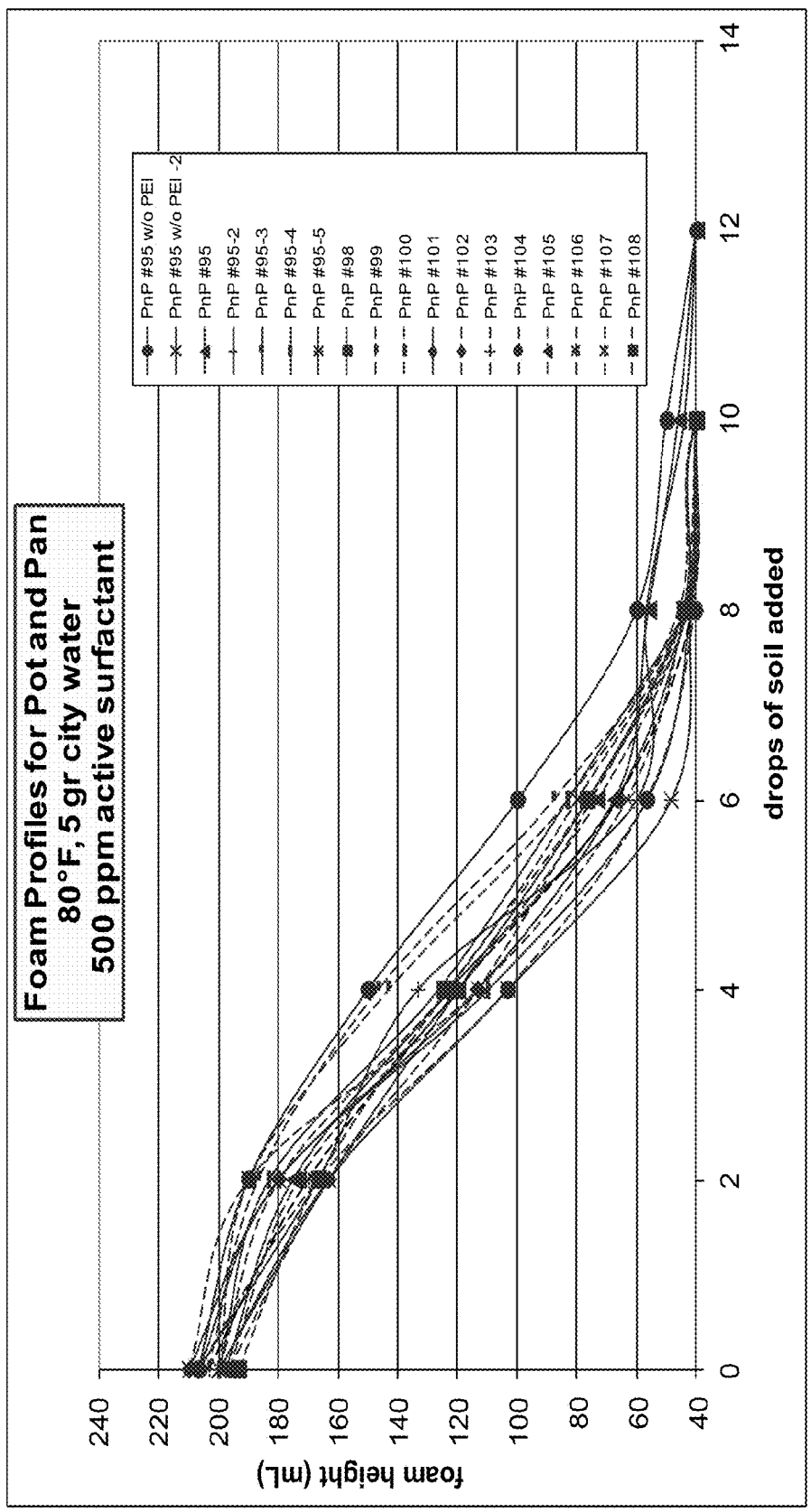
FIG. 20 is a graph depicting foam height as drops of soil are added for Commercial Product 1 and Commercial Product 2 (which include PEI-14 PEG-10/PPG-7) and Commercial Product 3, and formulas 95 with and without PEI, 95-2, 95-3, 95-4, 95-5, 99, 98, 100, 101, 102, 103, 104, 105, 106, 107, and 108.
Figure 21:
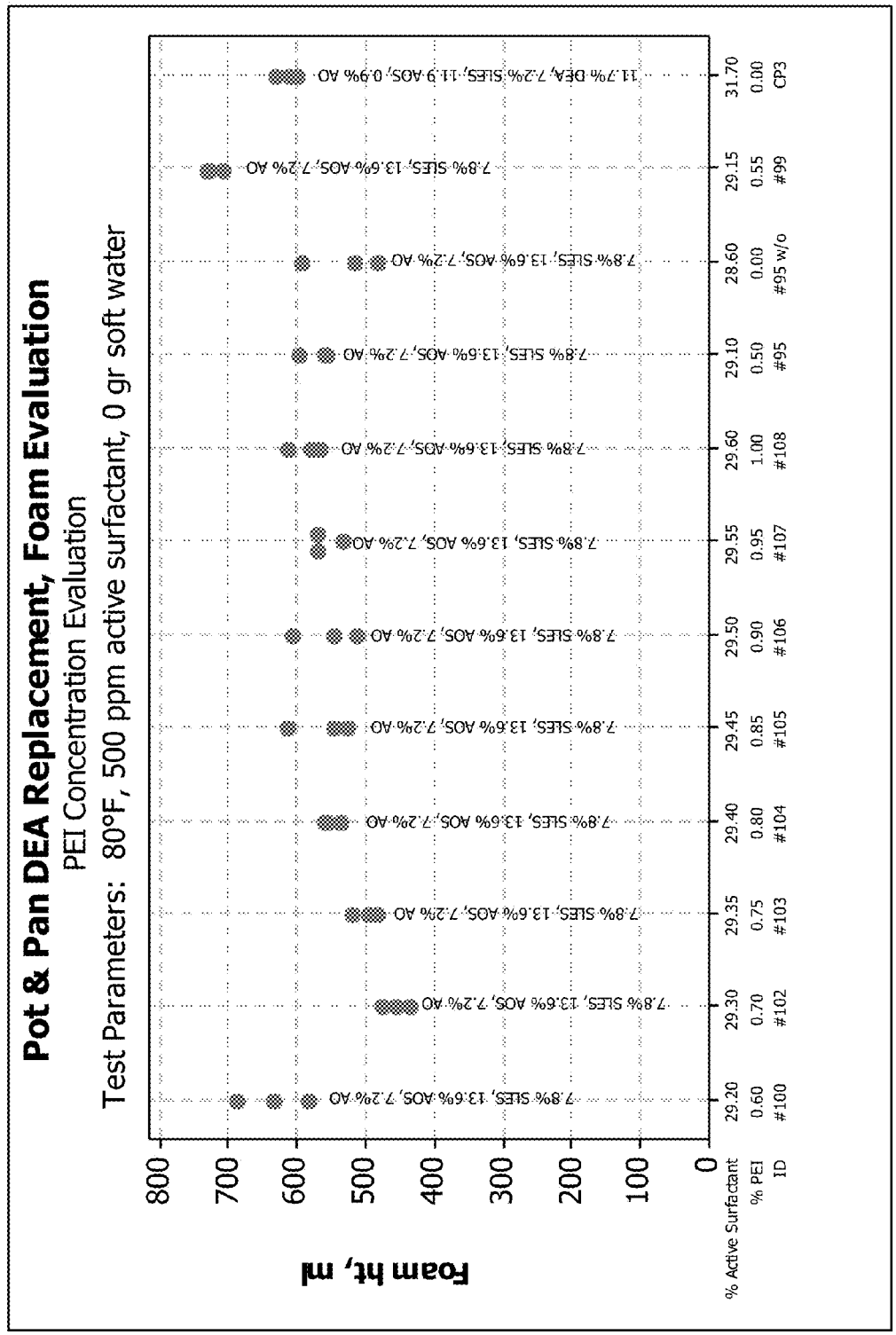
FIG. 21 is a graph showing foam height for formulas 95 with and without PEI, 99, 100, 102, 103, 104, 105, 106, 107, and 108 and with commercially available foaming pot and pan cleaning Commercial Product 3.
Figure 22:
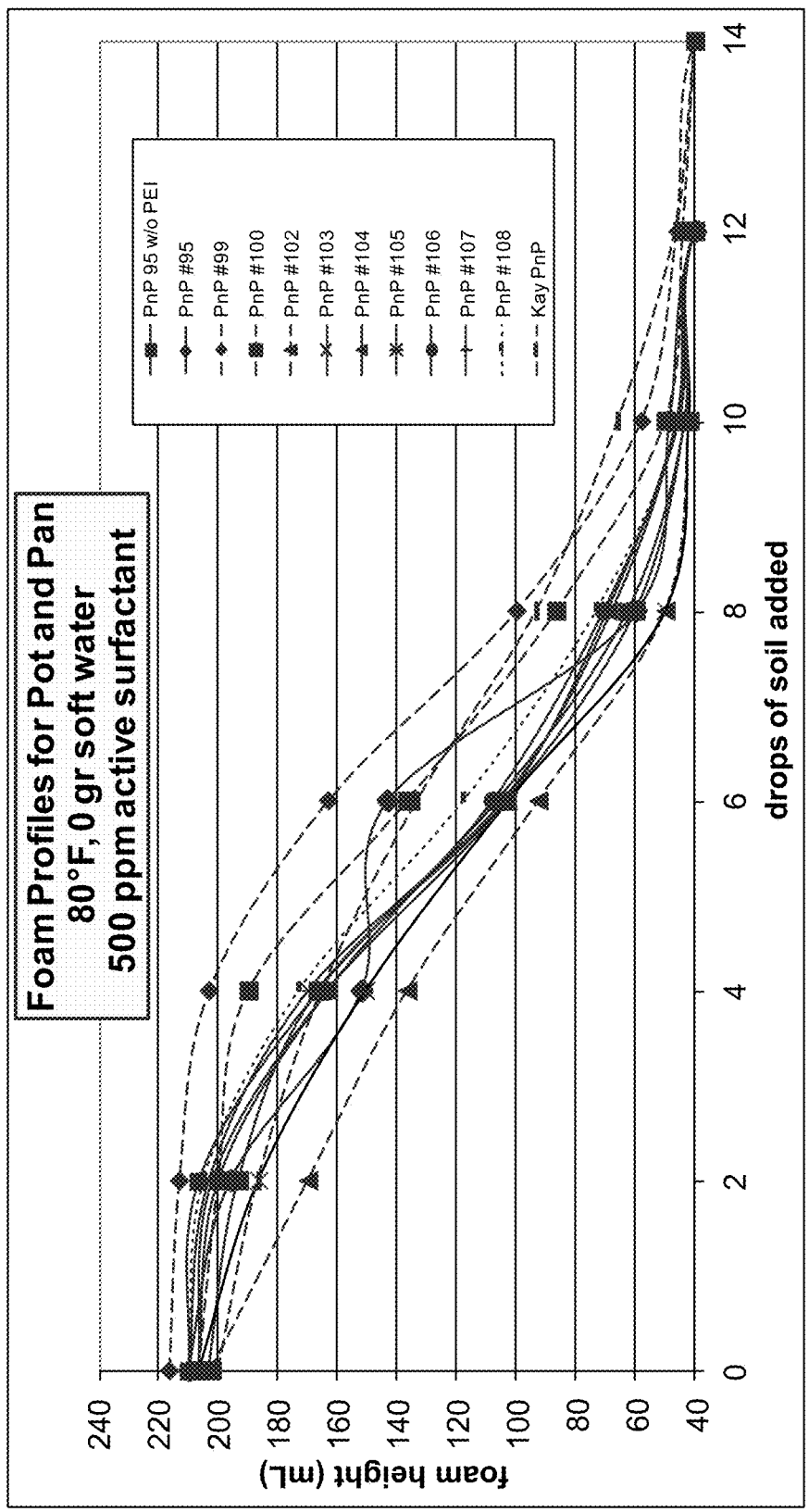
FIG. 22 is a graph depicting foam height as drops of soil are added for Commercial Product 3, and formula 95 with and without PEI, 99, 100, 102, 103, 104, 105, 106, 107, and 108.
Figure 23:
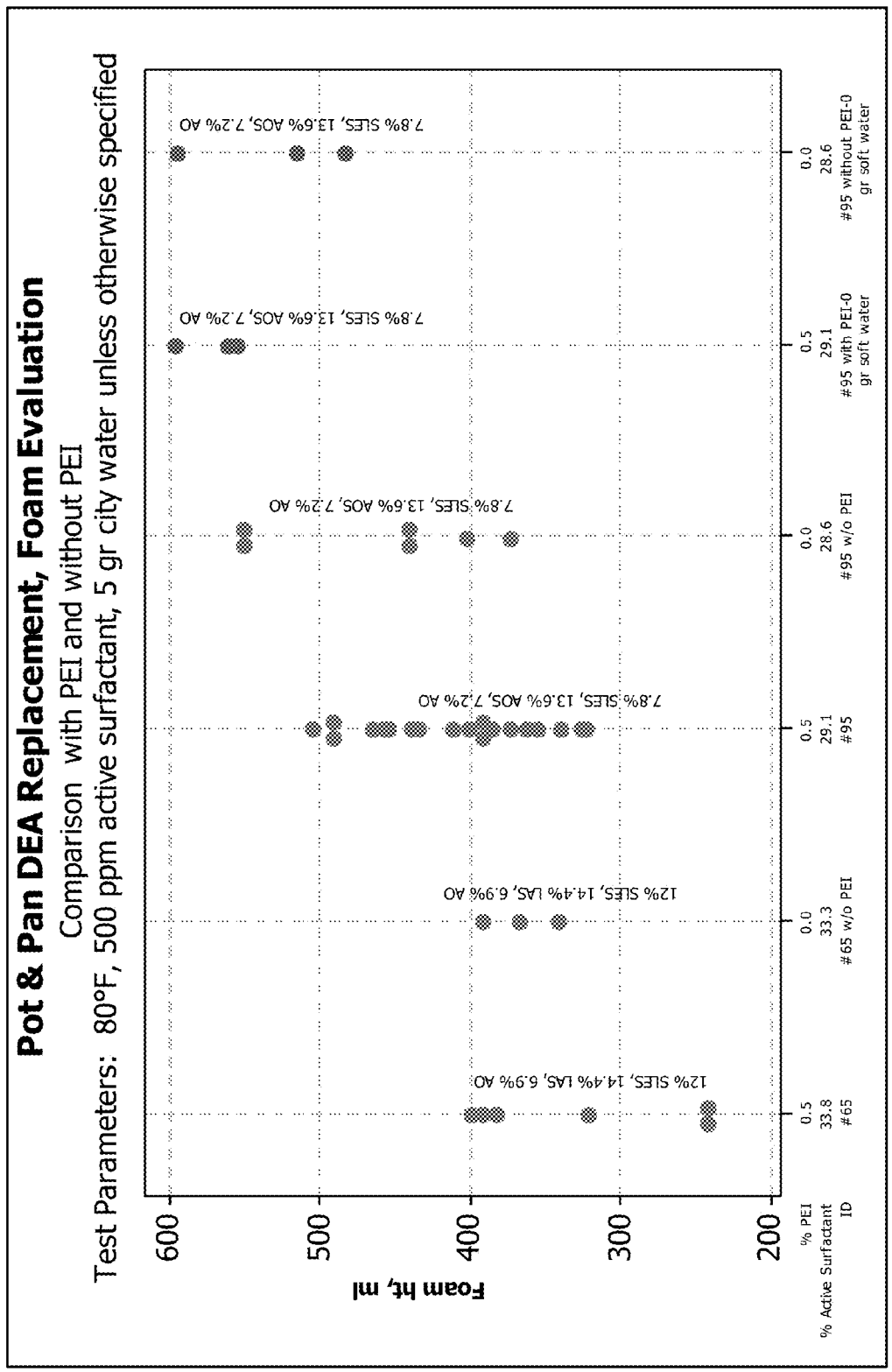
FIG. 23 is a graph showing foam height for formulas 95 with and without PEI, 65 with and without PEI and 95 with and without PEI
Figure 24:
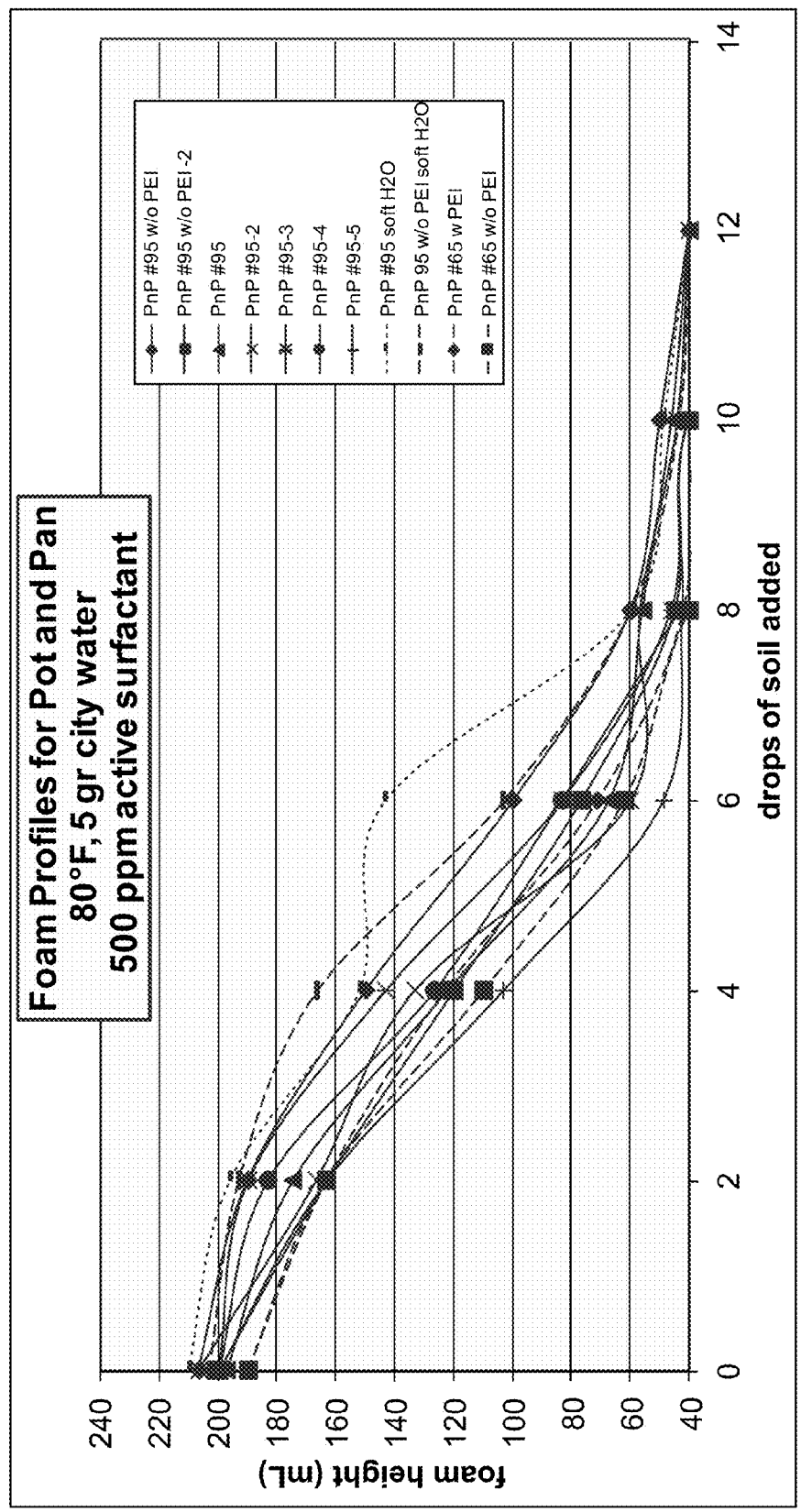
FIG. 24 is a graph depicting foam height as drops of soil are added for formula 65 with and without PEI, and several samples of formula 95 with PEI and formula 95 without PEI, and 95 with and without PEI.

FIG. 19 was an experiment to determine the optimum Sokalan HP-20 concentration needed for enhanced foam. It shows that 0.5%-0.55% is the optimal concentration for the specific combination and levels of surfactants. In fact, composition #95 with 0.55% Sokalan HP-20 produces the highest foam we have ever measured in soft water (see FIGS. 21 and 22)

At 80 F, use solution of LAS containing composition #65 shows poor foam in 5 grains city water but excellent foam in soft water. But at 110 F, good foam is obtained. These suggest a Krafft Temperature issue (FIGS. 15, 16, 17, 18, 23, and 24). The incorporation of a nonionic surfactant, Novel II, overcomes this Krafft Temperature problem (compositions #72, see FIGS. 15, 16, 17, and 18).

Our data show that foam-wise, our formulas with PEI ethoxylate are superior to those containing PEI-14 PEG-10/PPG-7, especially at 110 F.

Example 3

Emulsification of Soil, and Long Term Foam Stability (Stability of Foam at Certain Time after Agitation Stops)

Figure 34:
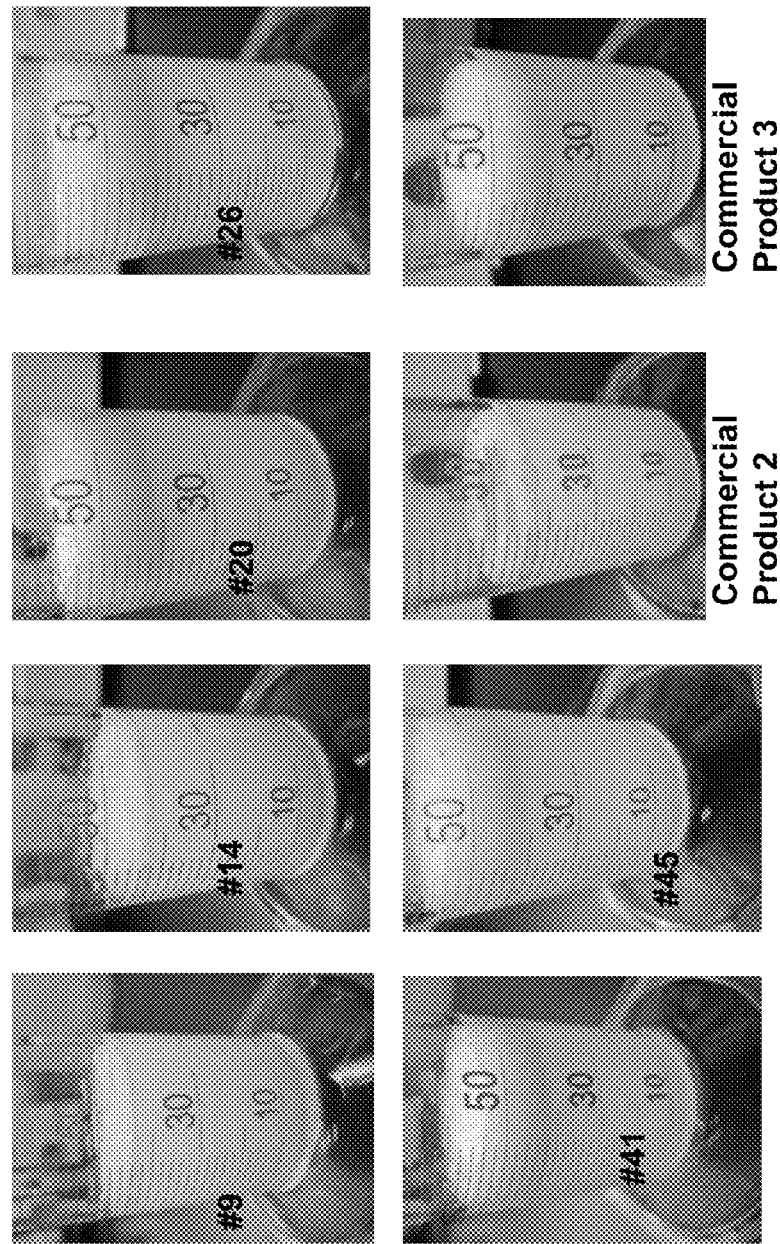
FIG. 34 are pictures showing the long term emulsification of soil and Long Term Foam Stability for compositions 9, 14, 20, 26, 41, 45 and controls Commercial Product 1 and Commercial Product 2 (which include PEI-14 PEG-10/PPG-7) and Commercial Product 3. (110° F., 5 gr city water, 6 drops of soil, 500 ppm surfactant, 20 minutes after mixing.

This testing results suggest that Cocamide DEA appears to help long term foam stability (Commercial Product 3) (20 minutes after agitation stops), while AO does not (#9). However, PEI ethoxylate+4-6% AO provides even better long term foam stability. Also, compositions with about 13.7% AO, and PEI-14 PEG-10/PPG-7 (Commercial Product 1) demonstrated poor long term foam stability. This yet again contrasts the difference between PEI ethoxylate and PEI-14 PEG-10/PPG-7 used by the commercial products. See FIG. 34.

Figure 25:
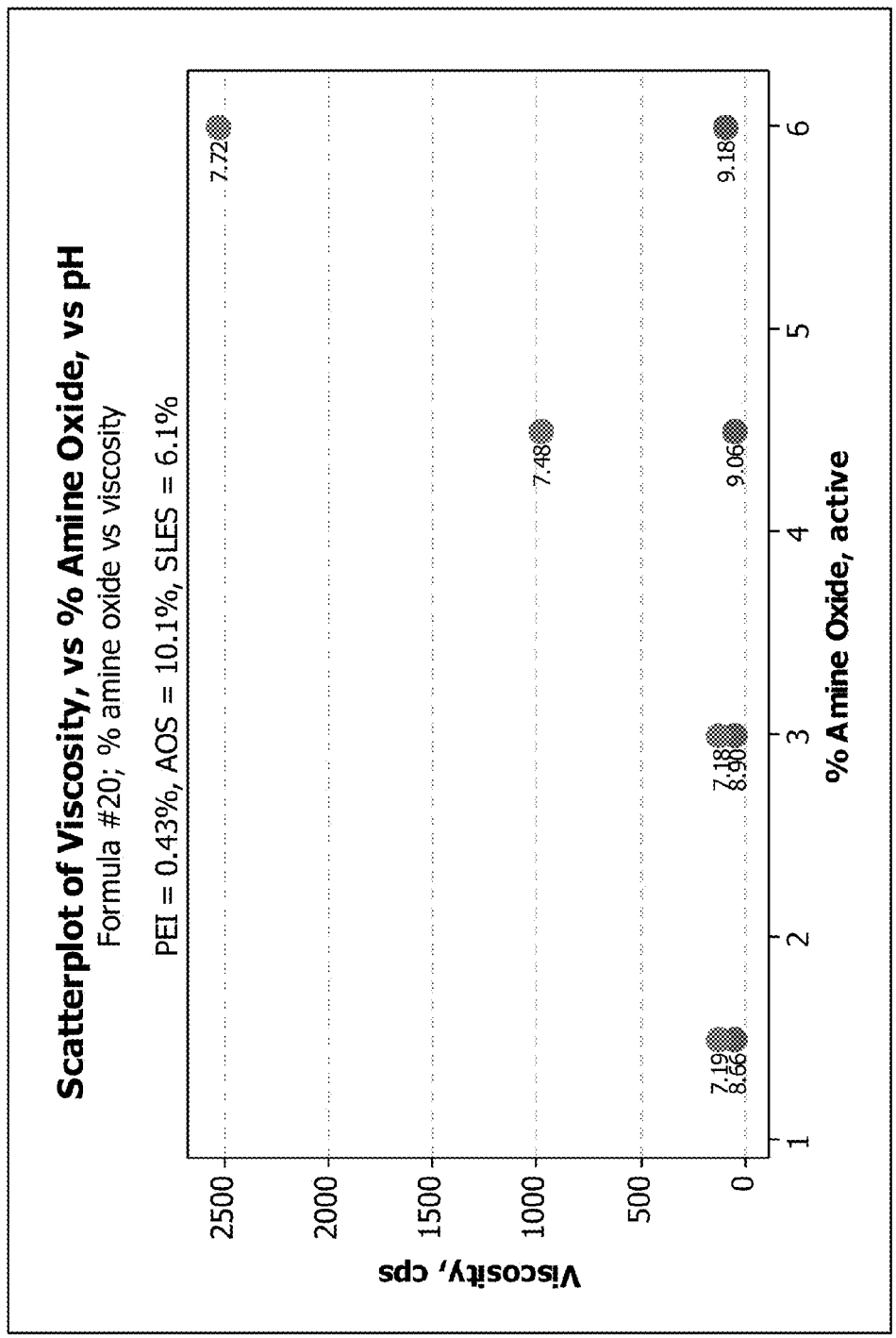
FIG. 25 is a scatter plot of the viscosity of the cleaning compositions as percent amine oxide.

(I) Processing Issues Associated with High Percent Amine Oxide:

The results shown in FIG. 25 indicate that at higher amounts of amine oxide (above 8%) the viscosity of the product becomes too high.

(II) Oily Soil Emulsification/Incorporation in the Foam Phase:

We have run foaming experiments with Sudan red dyed corn oil (for visual identification of where the oil is located) and use solutions of compositions that are identical except one has 0.5% of Sokalan HP-20, and the other one does not. The one with PEI ethoxylate (left graduated cylinder) visually incorporate more of the corn oil in the stable foam phase than the one without the PEI ethoxylate (right graduated cylinder). This is important as this suggest better soil management (removal from substrate and less chance of re-deposition back onto the substrate surfaces.

Figure 35:
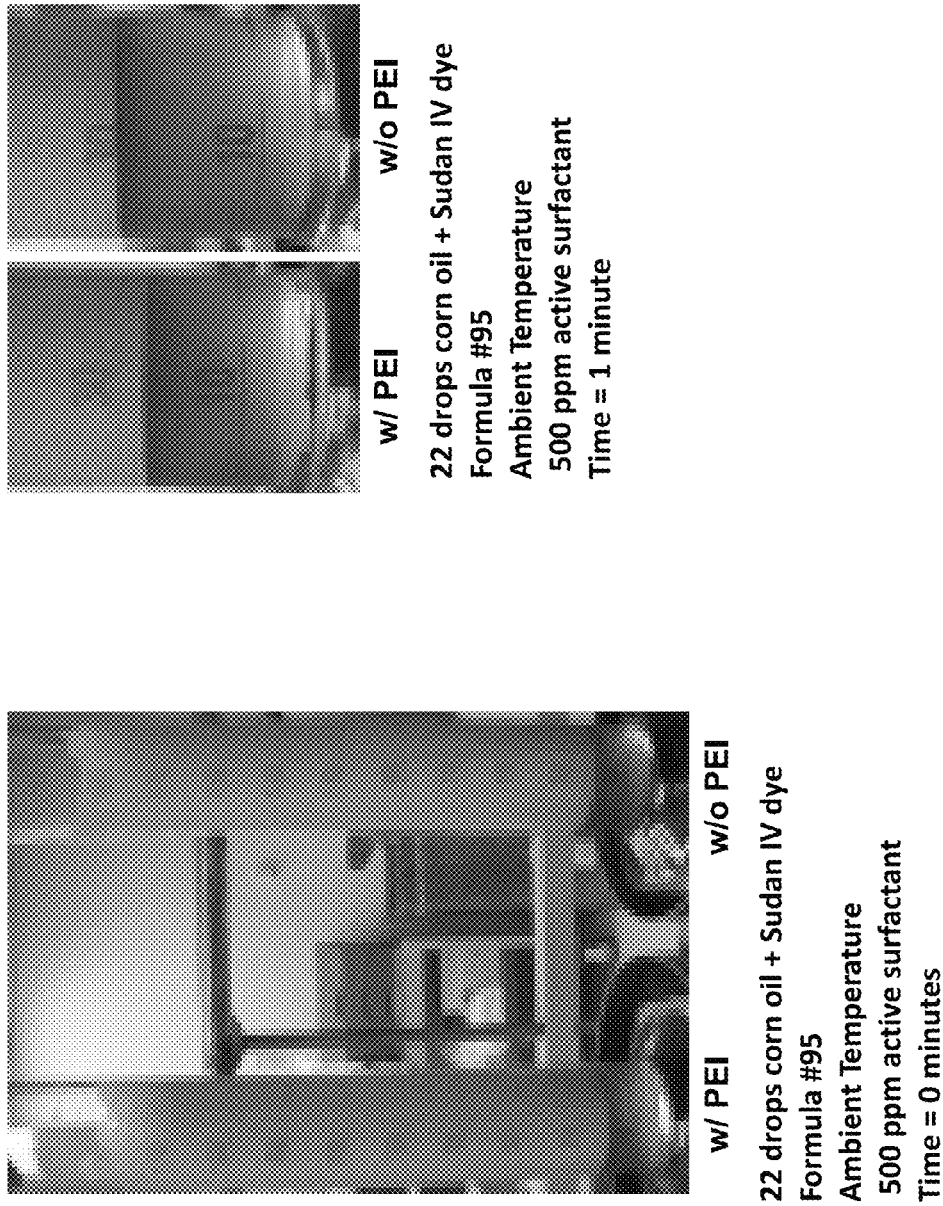
FIG. 35 includes photographs of foam with and without PEI, at time 0 minutes and 1 minute (22 drops corn oil plus Sudan IV dye, formula 95 at ambient temperature, 500 ppm active surfactant).
Figure 36:
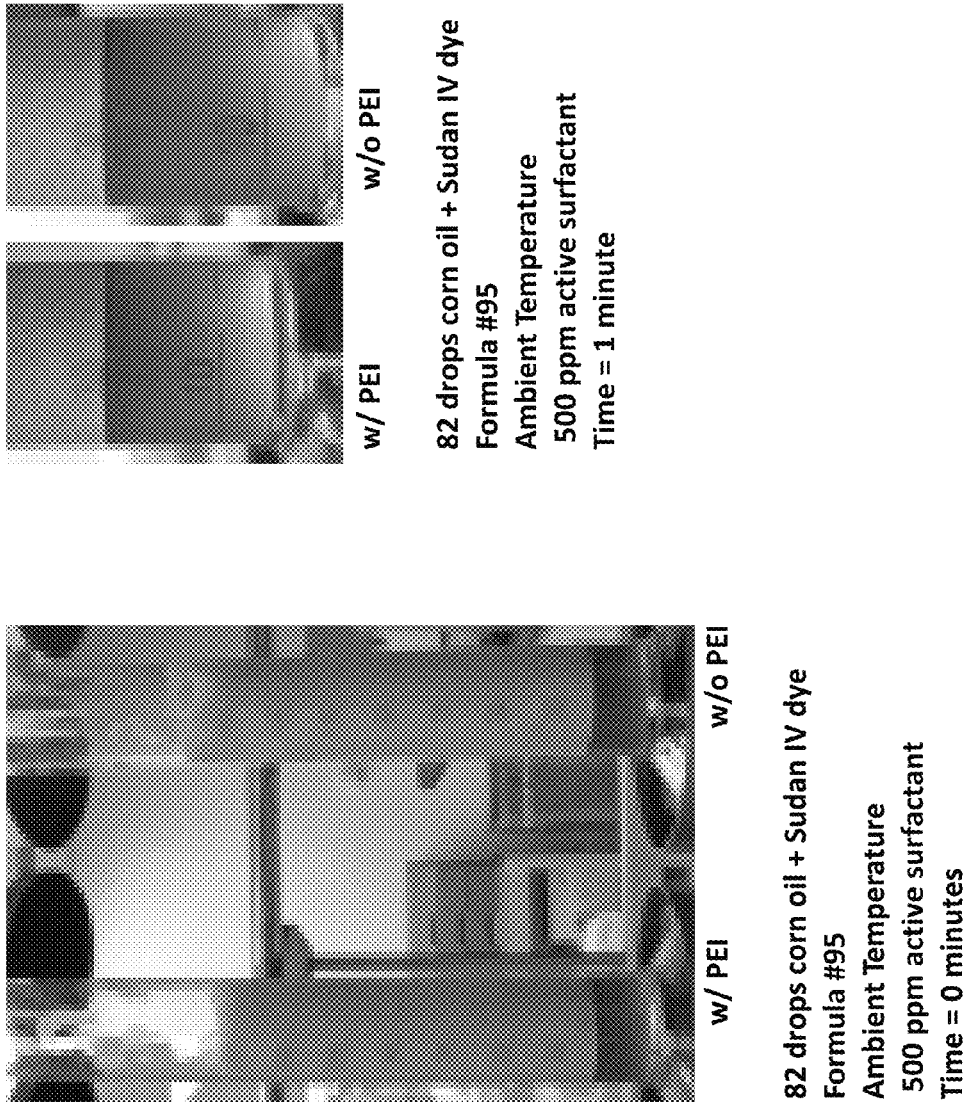
FIG. 36 includes photographs of foam with and without PEI, at time 0 minutes and 1 minute (82 drops corn oil plus Sudan IV dye, formula 95 at ambient temperature, 500 ppm active surfactant).

The PEI cylinder has a greater foam layer and less liquid layer at both 22 drops and 82 drops soil added indicating that more soil and more water is caught in the foam phase with PEI. See FIG. 35. The fact that more water is also captured indicates that this process may also useful for water removal in processes such as dewatering in gas exploration. See also FIG. 36.

The test method is described below:
Effectiveness of Oily Soil Emulsification and Incorporation in the Foam Phase
Test Method to Determine the Effectiveness of Oily Soil Emulsification and Incorporation in the Foam Phase
Purpose:
  To screen manual dish washing detergents for determination of the effectiveness of the foam to hold onto soil.
Scope:
  This procedure applies to any manual dish washing product
Apparatus and Materials:
1. Corn Oil or any other oil as preferred dyed with an oil soluble dye.
2. Disposable pipets
3. Guwina-Hoffmann rotation device
4. Ground glass stoppered graduated cylinders (250 ml)
5. Rubber stoppers
6. Water bath/heat chamber
Soil Formula:
1. 100% Corn Oil
2. 0.1% Oil Soluble Dye
Equipment Setup:
  Calibrate the Guwina-Hofmann rotation devise to 30 rpm.
Procedure:
1. Prepare solutions. Test solution is 500 ppm active surfactant (not to include SXS).
2. To a 250 ml graduated cylinder, add 40 mls of test solution. Repeat this step for each product. Label all cylinders.
3. Loosen stoppers and heat cylinders containing solutions to ambient temperature and a second set to 110° F.
4. Stopper cylinders, place in apparatus, and secure tightly.
5. Rotate for 120 sec (2 minutes). Record initial foam height and interface level between liquid and foam phase. Let graduated cylinder sit undisturbed for one minute and observe and record the interface between the liquid and foam phase. Add X drops soil with disposable pipettes.
6. Repeat step 5 as desired.

(III) Summary of Results:
  Both the PEI ethoxylate and associative thickener approach work very well. Very low level of these materials significantly outperforms high level of Cocamide DEA.
  Cocamide DEA appears to help long term foam stability (20 minutes after agitation stops), while AO does not. However, PEI ethoxylate+4-6% active AO provides even better long term foam stability.
  With PEI ethoxylate, the foam results show an optimal point with ~6% active AO. Above this level, processing will also be problematic.
  Addition of $Mg^{2+}$ negatively impacts foam at 80 F but not at 110 F. This could be a Krafft temperature issue.
  PEI ethoxylate is superior to the PEI-14 PEG-10/PPG-7 used by the Commercial products 1 and 2.
  It appears that increasing the level of PEI ethoxylate does not help. This could be a charge density issue.
  Potential to optimize the molecular weight and charge density of PEI ethoxylates.
  It should be emphasized that potentially other polymers with positive charges will also work, provided that they do not precipitate with the anionic surfactants in the composition. Other candidates include, but are not limited to, polyamines, polyquats, polyglycerol quats, VX10035 from Nalco (propoxylated mixture of PEI and glycol), and a similar Nalco product with PO-block-EO) units added to the PEI/glycol mixture.

Applications of our invention include, but are not limited to pot-n-pans, handsoaps, F&B facility foaming, VCD foaming, Nalco gas exploration water removal, foam fractionation, foaming environmental sanitizing, and hoof foaming sanitizing, etc.

Another potential use of PEI ethoxylate and the above mentioned polymers with positive charges is as pseudo-crosslinking agent for further interaction with Viscoelastic Surfactants.

Figure 26:
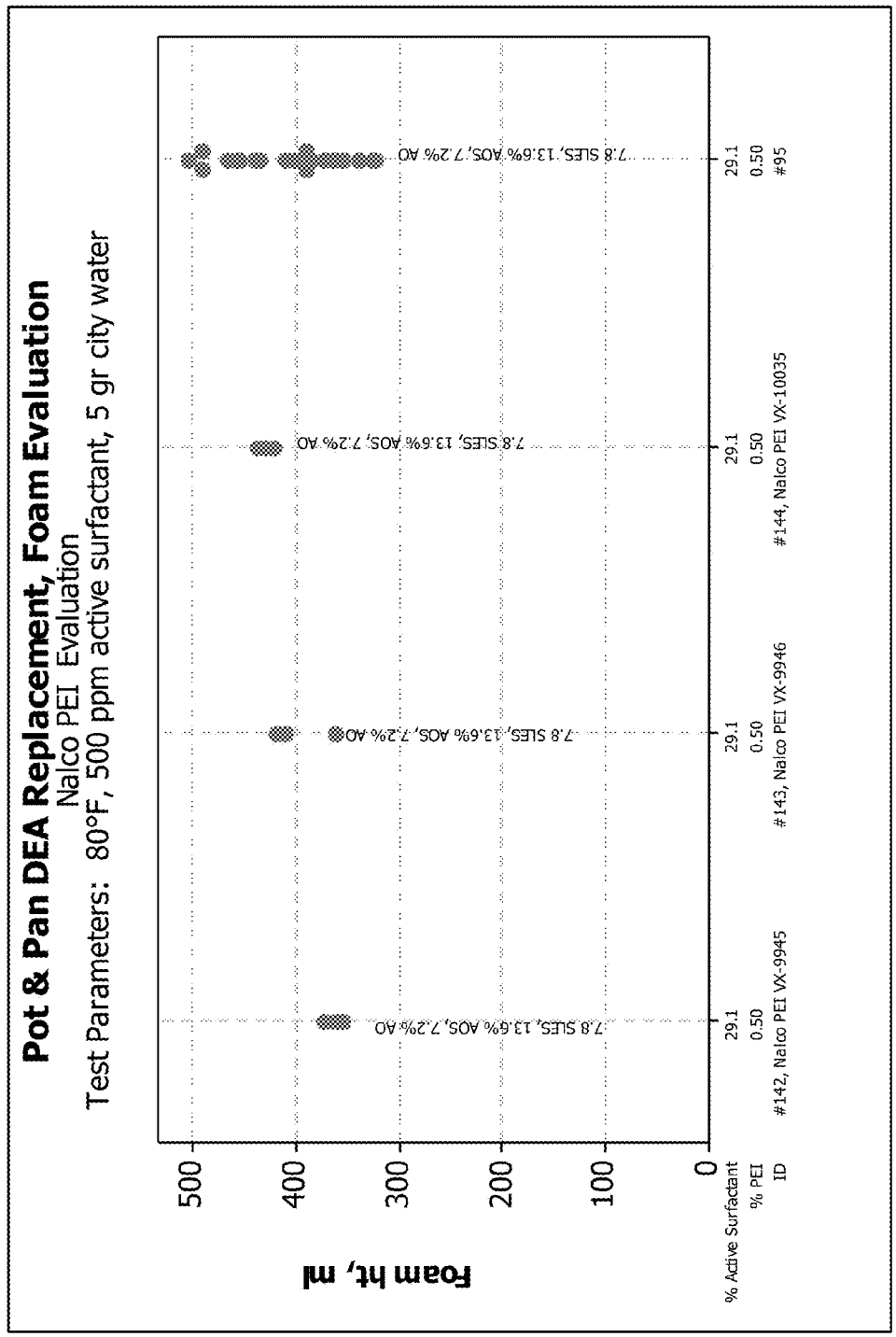
FIG. 26 is a graph showing foam height for formulas 95, 142, 143, and 144 at 80° F.
Figure 27:
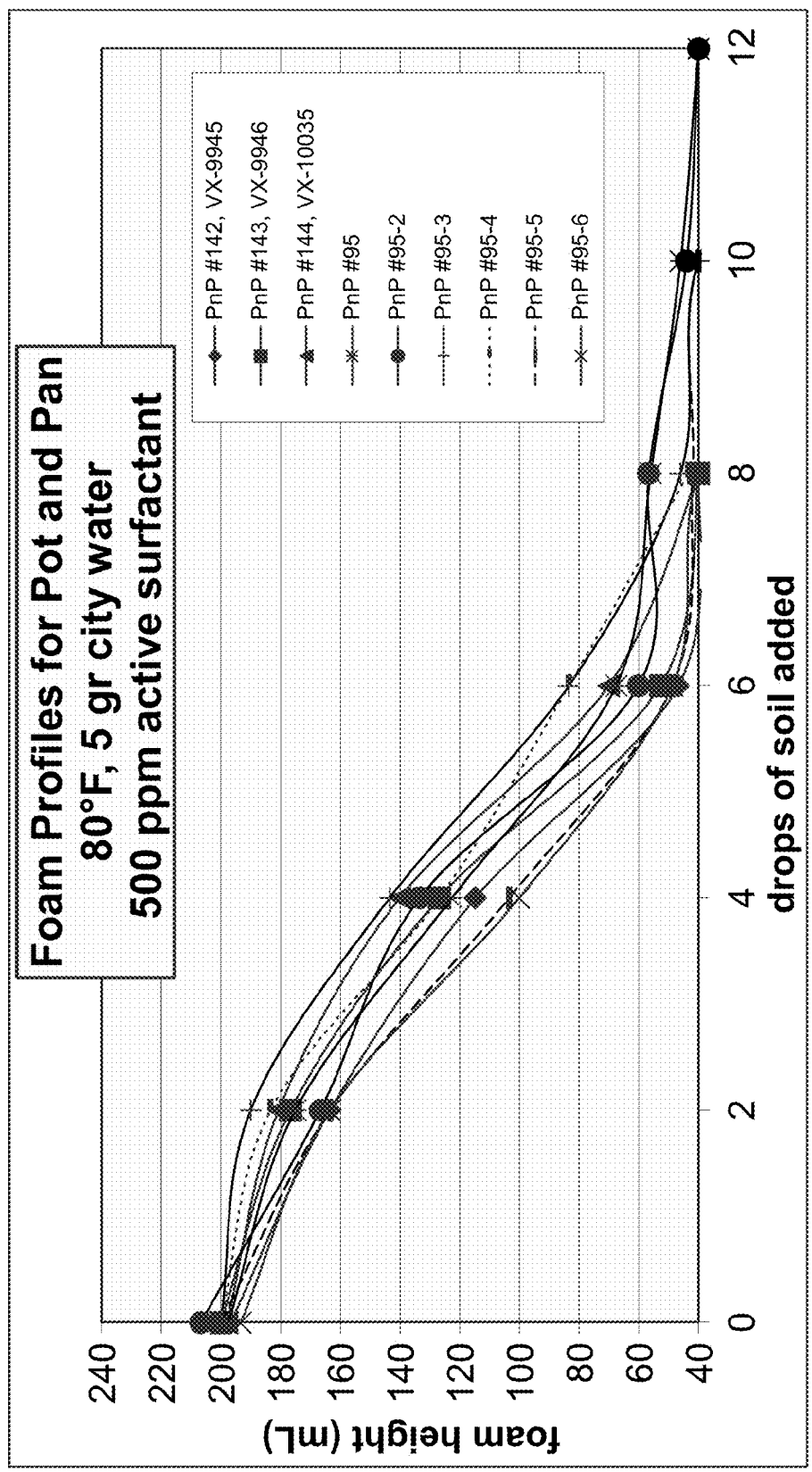
FIG. 27 is a graph depicting foam height as drops of soil are added for formulas 95, 142, 143, and 144 at 80° F.

FIGS. 26 and 27 are graphs showing additional formulations tested for foam stability using a PEI from another source. This second source shows no advantage over the primary PEI.

Figure 28:
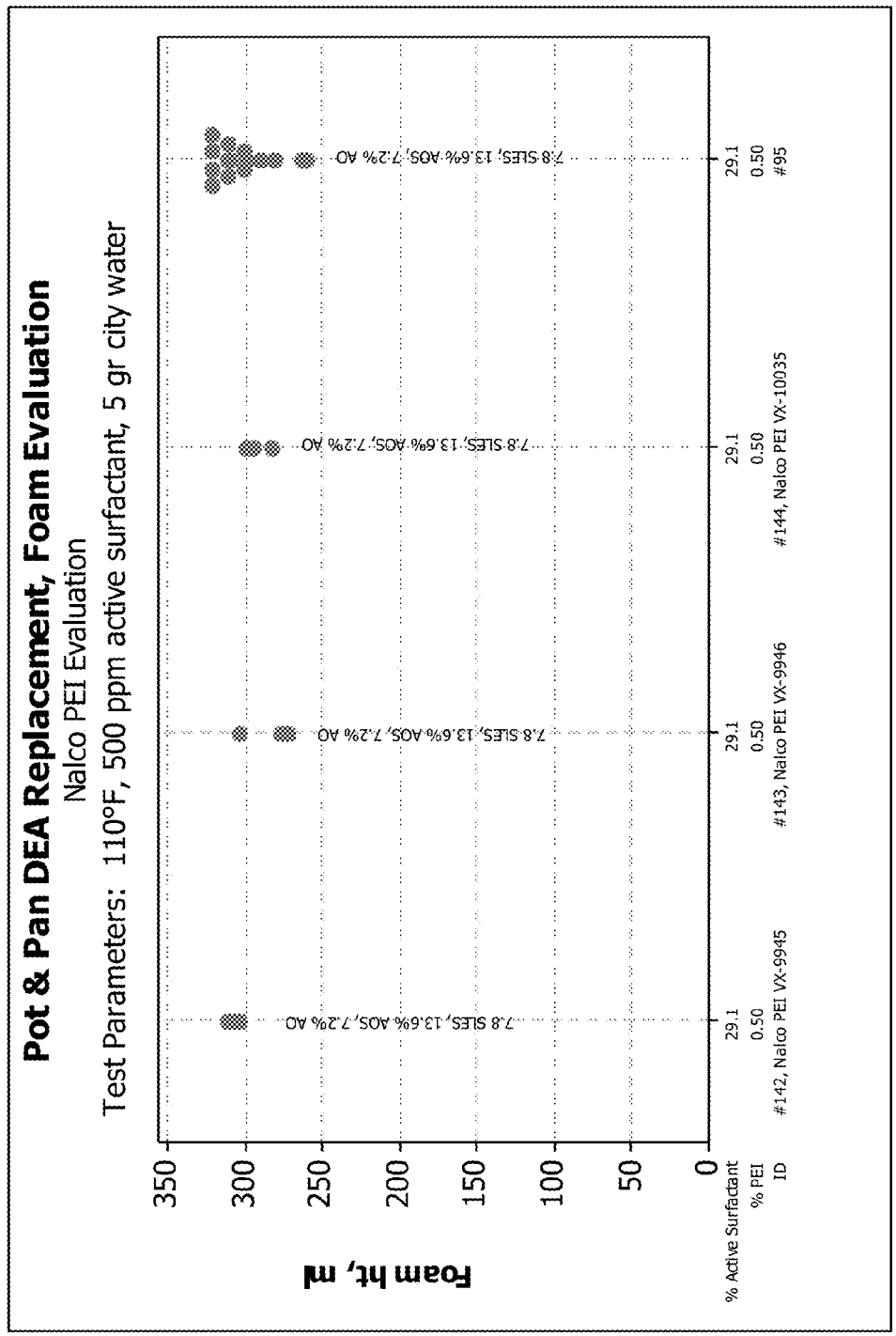
FIG. 28 is a graph showing foam height for formulas 95, 142, 143, and 144 at 110° F.
Figure 29:
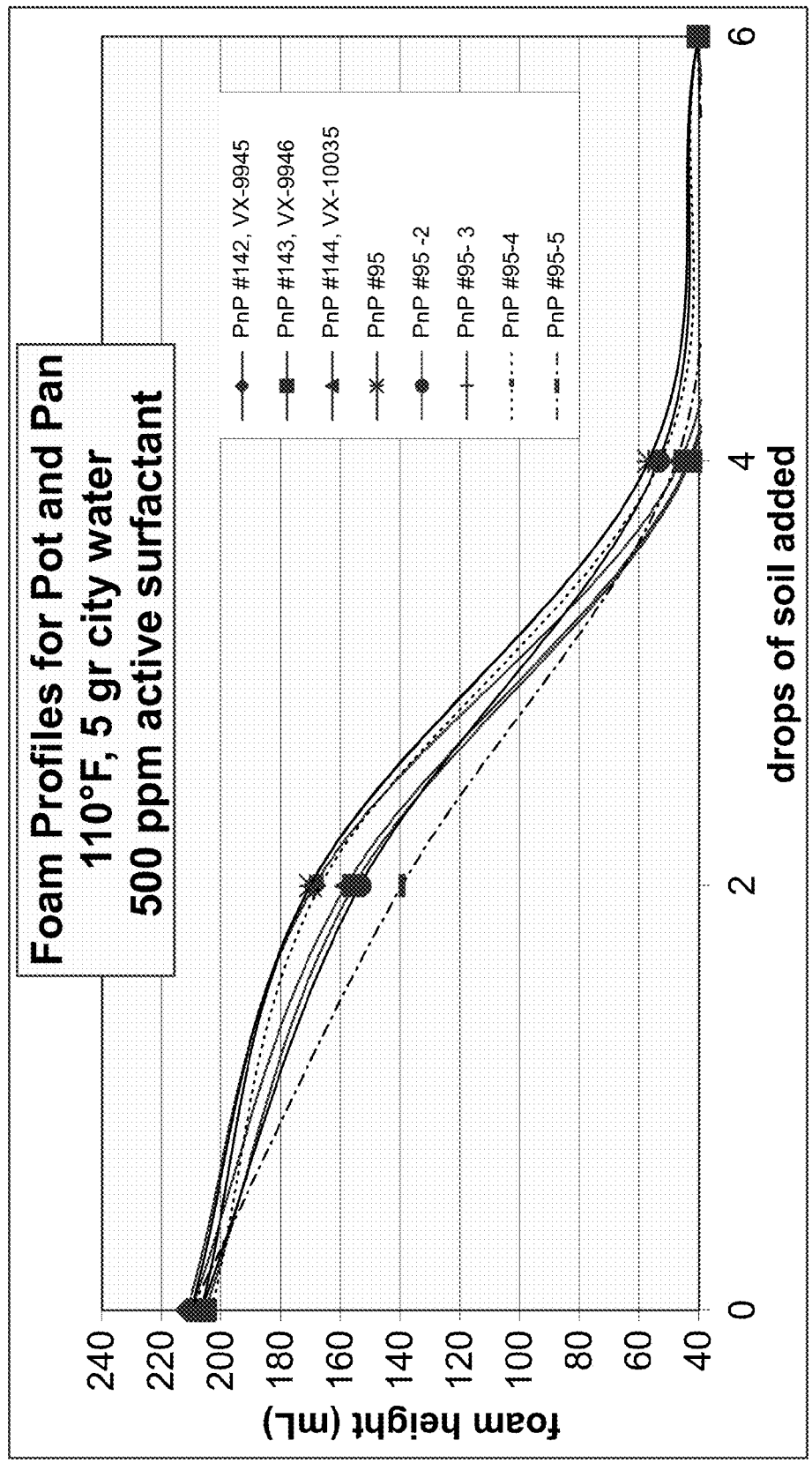
FIG. 29 is a graph depicting foam height as drops of soil are added for formulas 95, 142, 143, and 144 at 110° F.

FIGS. 28 and 29 are graphs showing additional formulations tested for foam stability using a PEI from another source. This second source shows no advantage over the primary PEI.

Figure 30:
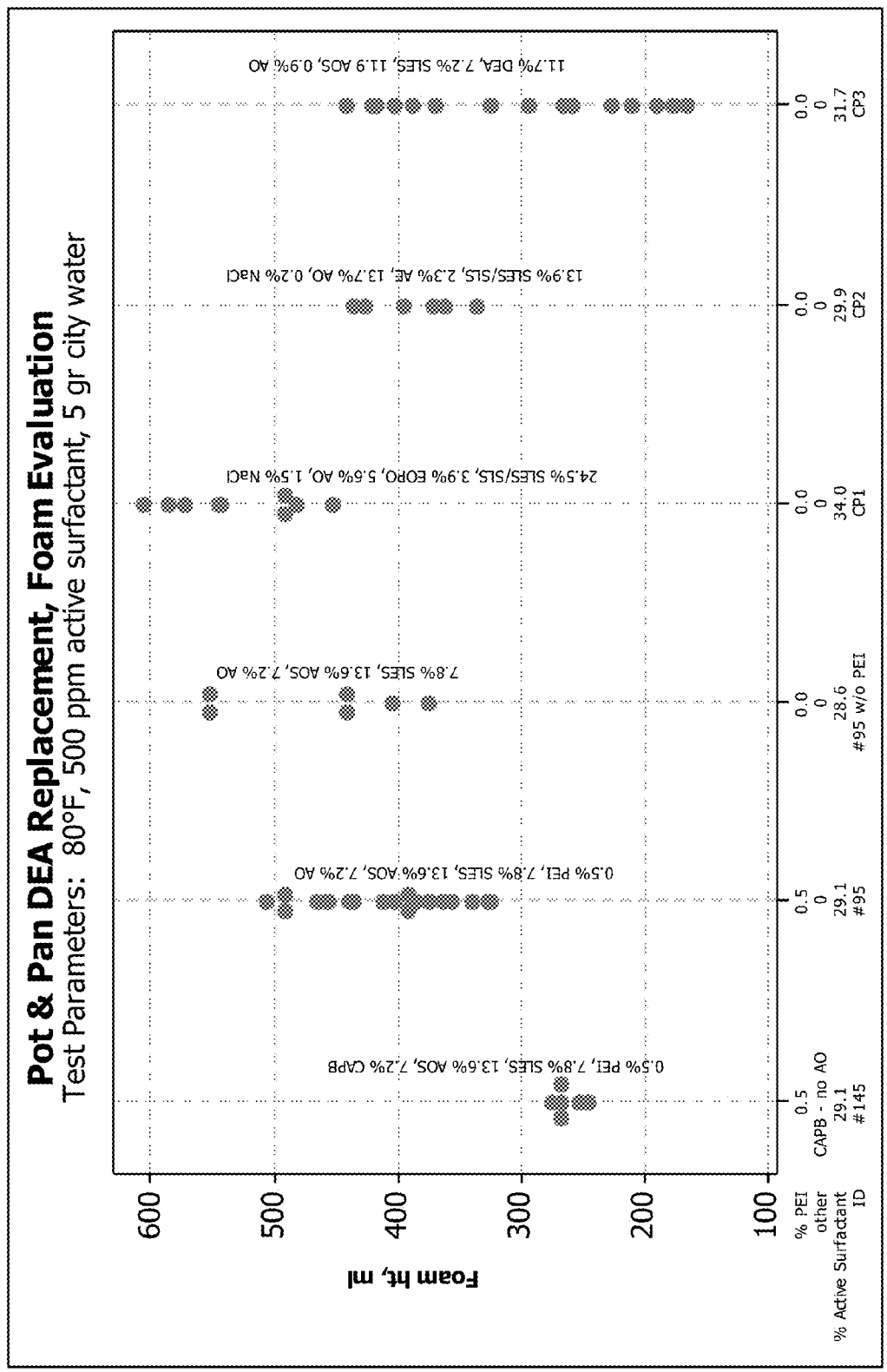
FIG. 30 is a graph showing foam height for formulas 145 and 95 at 80° F.
Figure 31:
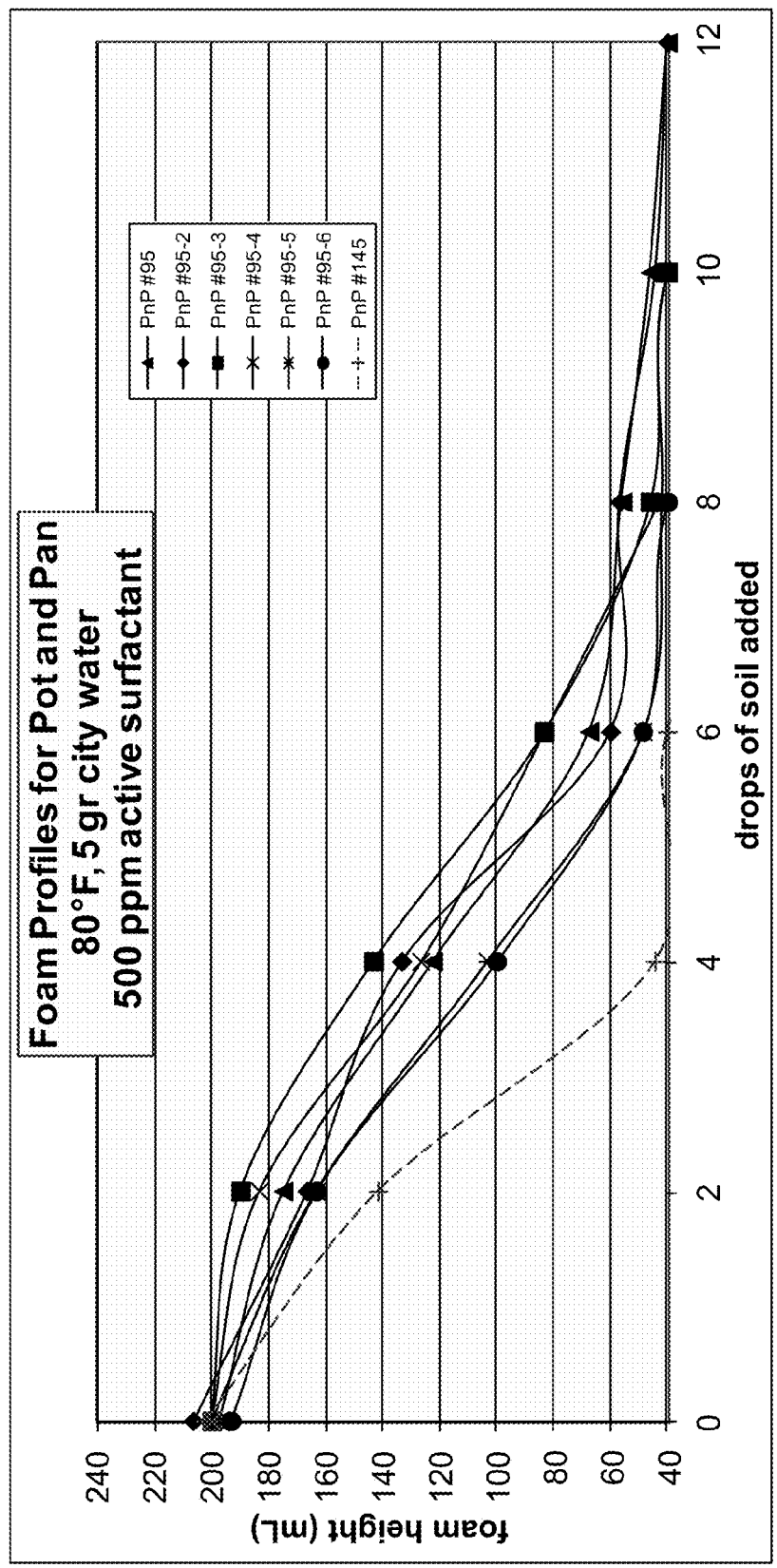
FIG. 31 is a graph depicting foam height as drops of soil are added for formulas 145 and 95.

FIGS. 30 and 31 are graphs at 80° F. showing that the benefit of PEI and an amphoteric surfactant is not limited to an amine oxide as the aphoteric surfactant. In this case cocamidopropyl betaine was used.

Figure 32:
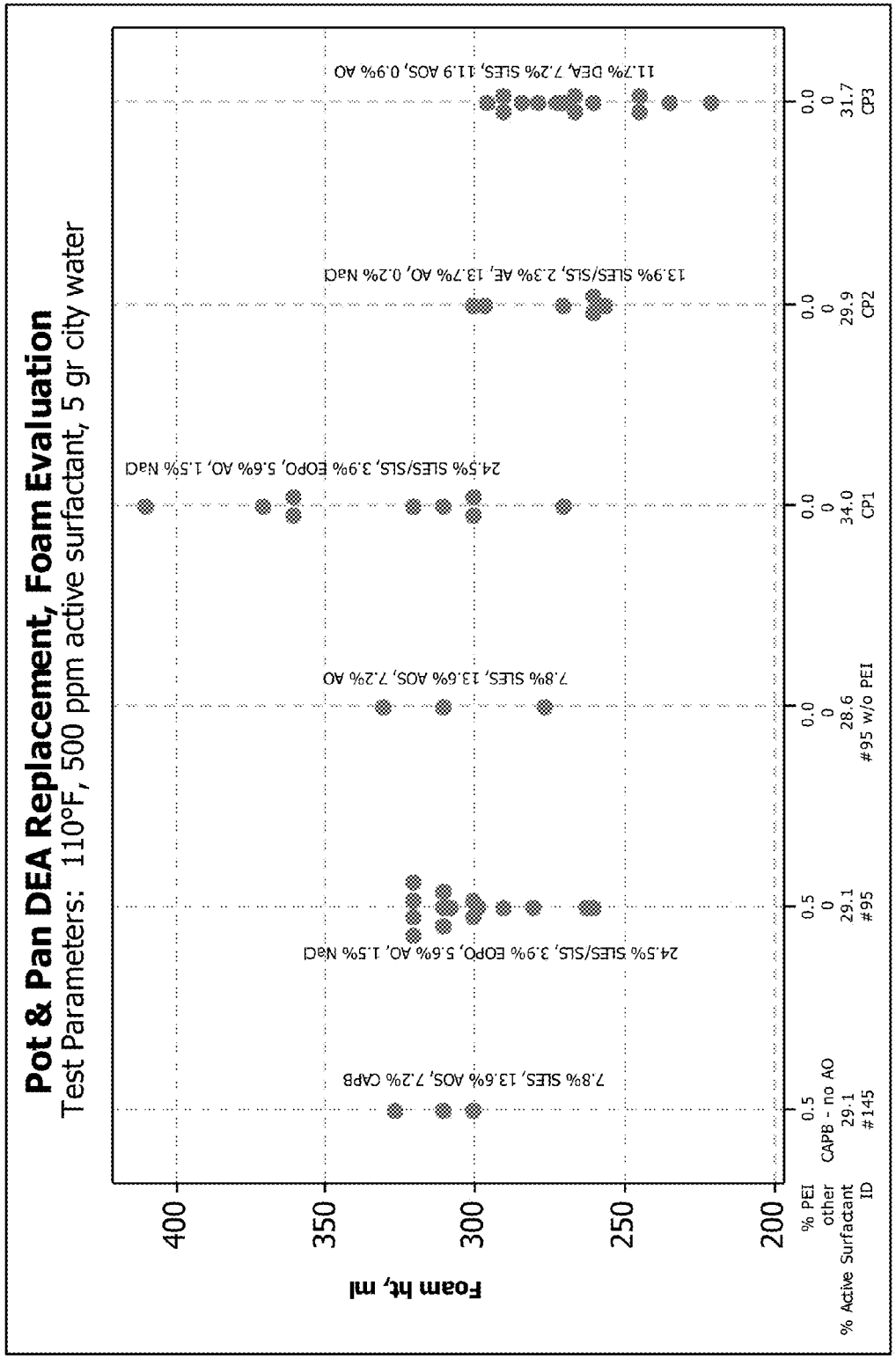
FIG. 32 is a graph showing foam height for formulas 145 and 95 at 110° F.
Figure 33:
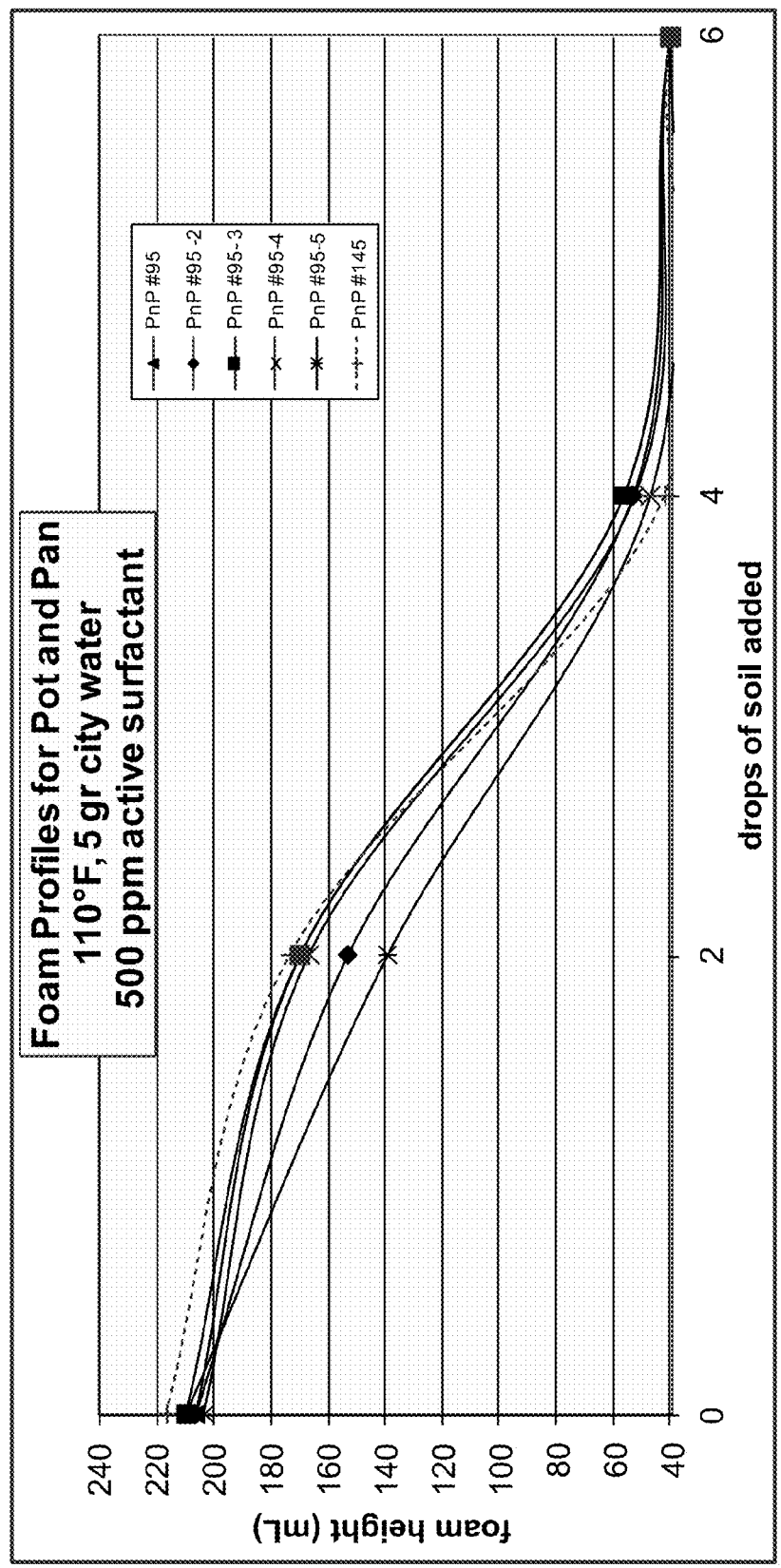
FIG. 33 is a graph depicting foam height as drops of soil are added for formulas 145 and 95.

FIGS. 32 and 33 clearly show the benefit of enhanced foam when using the PEI ethoxylate and an amphoteric surfactant other than an amine oxide at 110° F.

What is claimed is:

1. A foaming cleaning composition comprising:
   from about 0.5 wt. % to about 5 wt. % of a positively charged PEI polymer;
   between about 1 wt. % to about 75 wt. % of an anionic surfactant; and
   an amphoteric surfactant, wherein said amphoteric surfactant comprises amine oxide in an amount between about 2 wt. % and about 6 wt. % actives;
   said composition having less than 0.5 wt. % of cocamide DEA.

2. The foaming cleaning composition of claim 1 wherein said PEI is an ethoxylated PEI polymer.

3. The foaming cleaning composition of claim 1 wherein said PEI is present in an amount of from about 0.5 wt. % to about 3.5 wt. %.

4. The foaming cleaning composition of claim 1 wherein said anionic surfactant is present in an amount of from about 5 wt. % to about 65 wt. %.

5. The foaming cleaning composition of claim 1 said composition having less than 0.05 wt. % of cocamide DEA.

6. The foaming cleaning composition of claim 1 wherein said anionic surfactant comprises sodium laurel ether sulfate and alpha olefin sulfonate or alkylbenzene sulfonic acid.

7. The foaming cleaning composition of claim 1 wherein said PEI polymer is present in an amount between about 0.1 wt. % and about 2 wt. %.

8. A foaming cleaning composition comprising:
   (a) from about 0.5 wt. % to about 5 wt. % of a positively charged polymer selected from the group consisting of: polyamines, polyquats, polyglycerol quats, ethoxylated PEI, propoxylated PEI, or a mixture of PEI and glycol, or PEI with PO-blocked EO units added to the PEI/glycol mixture;
   (b) from about 5 wt. % to about 65 wt. % of an anionic surfactant; and
   (c) from about 2 wt. % to about 6 wt. % active of an amphoteric surfactant, wherein said amphoteric surfactant is an amine oxide; and
   (d) said composition having less than 0.5 wt. % of cocamide DEA.

9. The foaming cleaning composition of claim 8 wherein said PEI is an ethoxylated PEI polymer.

10. The foaming cleaning composition of claim 8 said composition having less than 0.05 wt. % of cocamide DEA.

11. The foaming cleaning composition of claim 8 said composition having less than 0.01 wt. % of cocamide DEA.

12. The foaming cleaning composition of claim 8 further comprising a non ionic surfactant.

13. The foaming cleaning composition of claim 8 wherein said anionic surfactant comprises sodium laurel ether sulfate and alpha olefin sulfonate or alkylbenzene sulfonic acid.

14. A method of stabilizing foam and the water component thereof in a foam cleaning or water removal method comprising:
   providing a positively charged PEI polymer which will electrostatically interact with an anionic surfactant and amphoteric surfactant but which does not precipitate out so that foam height and time before dissipation is increased from that of a foaming cleaning composition without such polymer; and
   admixing said polymer with the anionic surfactant and the amphoteric surfactant; wherein said PEI polymer is in an amount between about 0.5 wt. % and about 5 wt. %, said anionic surfactant is in an amount between about 1 wt. % and about 75 wt. %, and said amphoteric surfactant comprises an amine oxide and is present in an amount between about 2 wt. % and about 6 wt. % actives.

15. The method of claim 14 wherein said polymer is PEI or a derivative thereof.

16. The method of claim 14 wherein said anionic surfactant is selected from the group consisting of:
   sulfonic acids, sulfuric acid esters, and salts thereof.

17. The method of claim 14 wherein said foam stabilization also includes water removal in a gas dewatering process.

18. The method of claim 16 wherein said sulfonic acids are selected from the group consisting of isethionates, alkylaryl sulfonates, alkyl sulfonates, sulfosuccinates, and salts thereof; and wherein said sulfuric acid esters are selected from the group consisting of alkyl ether sulfates, alkyl sulfates, and salts thereof.

* * * * *